United States Patent
Xu et al.

(10) Patent No.: US 10,246,504 B2
(45) Date of Patent: Apr. 2, 2019

(54) ENGINEERED RECEPTOR AND THEIR USE

(71) Applicant: University of Pittsburgh—Of the Commonwealth System of Higher Education, Pittsburgh, PA (US)

(72) Inventors: Yan Xu, Wexford, PA (US); Pei Tang, Wexford, PA (US); Tommy S. Tillman, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/455,047

(22) Filed: Mar. 9, 2017

(65) Prior Publication Data

US 2017/0190758 A1   Jul. 6, 2017

Related U.S. Application Data

(63) Continuation of application No. 14/650,859, filed as application No. PCT/US2013/073934 on Dec. 9, 2013, now Pat. No. 9,624,288.

(60) Provisional application No. 61/735,503, filed on Dec. 10, 2012.

(51) Int. Cl.
| | |
|---|---|
| C07K 14/705 | (2006.01) |
| C12N 15/12 | (2006.01) |
| C12N 15/31 | (2006.01) |
| C12N 15/63 | (2006.01) |
| A61K 38/16 | (2006.01) |
| A61P 25/04 | (2006.01) |
| A61P 11/00 | (2006.01) |
| B82Y 5/00 | (2011.01) |
| C07K 14/195 | (2006.01) |
| C07K 14/27 | (2006.01) |
| A61K 38/17 | (2006.01) |
| A61K 38/00 | (2006.01) |

(52) U.S. Cl.
CPC .......... *C07K 14/705* (2013.01); *A61K 38/164* (2013.01); *A61K 38/177* (2013.01); *C07K 14/195* (2013.01); *C07K 14/27* (2013.01); *A61K 38/00* (2013.01); *B82Y 5/00* (2013.01); *C07K 2319/00* (2013.01); *C07K 2319/03* (2013.01)

(58) Field of Classification Search
None
See application file for complete search history.

(56) References Cited

FOREIGN PATENT DOCUMENTS

EP   2390266 A1   11/2011

OTHER PUBLICATIONS

Bertaccini et al., "Modeling Anesthetic Binding Sites within the Glycine Alphas One Receptor based on Prokaryotic Ion Channel Templates: the Problem with TM4," *J. Chem. Inf. Model* 50(12):2248-2255 (Dec. 27, 2010).
Cetlin et al., *Nature* 4:23-30(2012)(in Russian w/English language translation).
Duret et al., "Functional prokaryotic-eukaryotic chimera from the pentameric ligand-gated ion channel family," *PNAS* 108(29): 12143-12148 (Jul. 19, 2011).
International Search Report from the parent PCT Application No. PCT/US2013/073934, 3 pages (dated Apr. 17, 2014).
Kinde et al., "Conformational changes underlying desensitization of the pentameric ligand-gated ion channel ELIC," *Structure* 23:995-1004 (Jun. 2, 2015).
Marabelli et al., "Mechanism of activation of the prokaryotic channel ELIC by propylamine: A single-channel study," *J. Gen. Physiol.* 145(1): 23-45 (Dec. 29, 2014).
Mowrey et al., "Open-channel structures of the human glycine receptor α1 full-length transmembrane domain," *Structure* 21(10): 1897-1904 (published online Aug. 29, 2013).
Pan et al., "Structure of the pentameric ligand-gated ion channel ELIC cocrystallized with its competitive antagonist acetylcholine," *Nature Communications* 3(714):1-8 (Mar. 6, 2012).
Schmandt et al., "A chimeric prokaryotic pentameric ligand-gated channel reveals distinct pathways of activation," *J. Gen. Physiol.* 146(4): 323-340 (Sep. 28, 2015).
Smart and Pierre Paoletti, "Synaptic neurotransmitter-gated receptors," *Cold Spring Harb. Perspect. Biol. Doi.* 1-26 (Jan. 12, 2012).
Tang et al., "NMR structures of the second transmembrane domain of the human glycine receptor alpha(1) subunit: model of pore architecture and channel gating," *Biophysical Journal* 83(1): 252-262 (Jul. 2002).
Tillman et al., "ELIC-α7 nicotinic acetylcholine receptor (α7nAChR) chimeras reveal a prominent role of the extracellular-transmembrane domain interface in allosteric modulation," *Journal of Biological Chemistry* 289(20): 13851-13857 (May 16, 2014).
Written Opinion from the parent PCT Application No. PCT/US2013/073934, 5 pages (dated Feb. 26, 2014).
Corringer et al., "Atomic structure and dynamics of pentameric ligand-gated ion channels: new insight from bacterial homologues," *Journal of Physiology* 588.4: 565-572 (2010).

(Continued)

*Primary Examiner* — Julie Ha
*Assistant Examiner* — Kristina M Hellman
(74) *Attorney, Agent, or Firm* — Klarquist Sparkman, LLP

(57) ABSTRACT

Engineered chloride channel receptors, nucleic acids encoding these receptors, expression vectors including these nucleic acids are disclosed herein. Nanoparticles and pharmaceutical compositions including these engineered chloride channel receptors, nucleic acids, and expression vectors are disclosed. The use of these compositions and nanoparticles, such as for the treatment of pain, cystic fibrosis and asthma, is also disclosed.

19 Claims, 13 Drawing Sheets
(2 of 13 Drawing Sheet(s) Filed in Color)
Specification includes a Sequence Listing.

(56) References Cited

OTHER PUBLICATIONS

Nys et al., "Structural insights into Cys-loop receptor function and ligand recognition," *Biochemical Pharmacology* 86: 1042-1053 (2013).

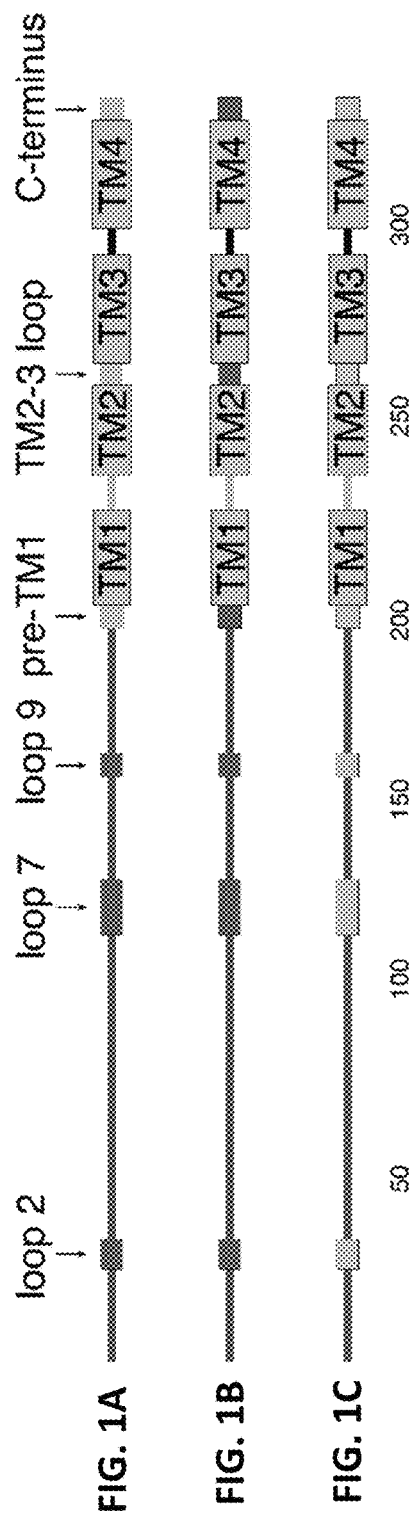

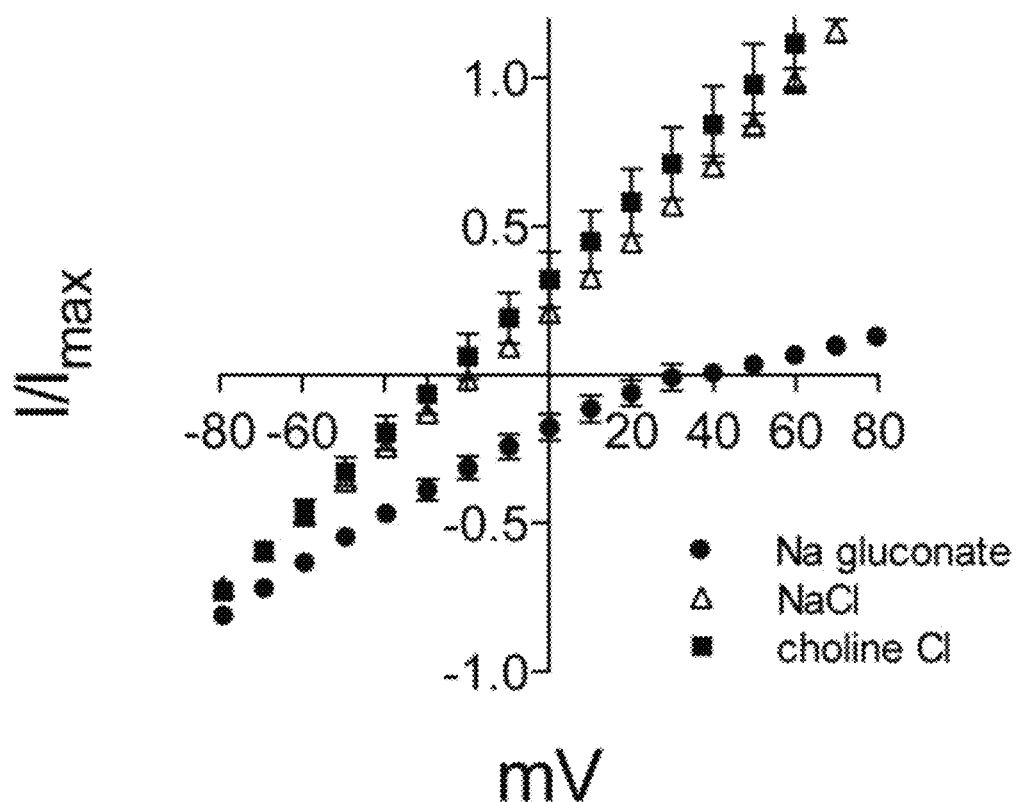

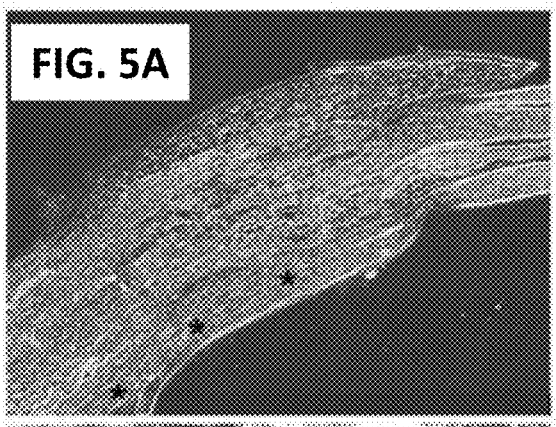
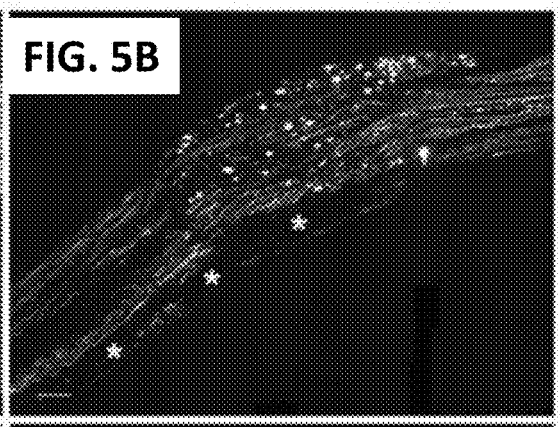
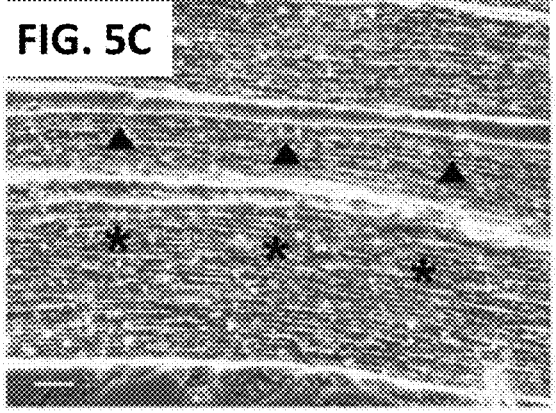
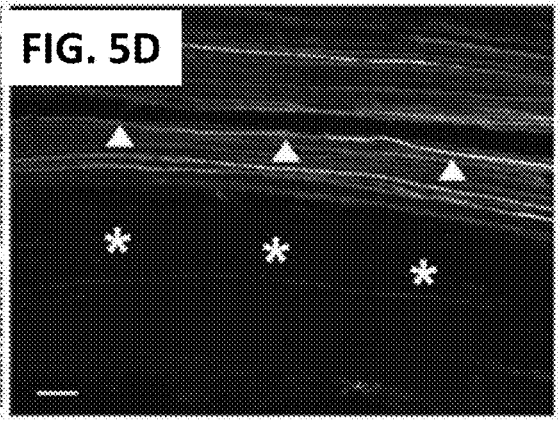

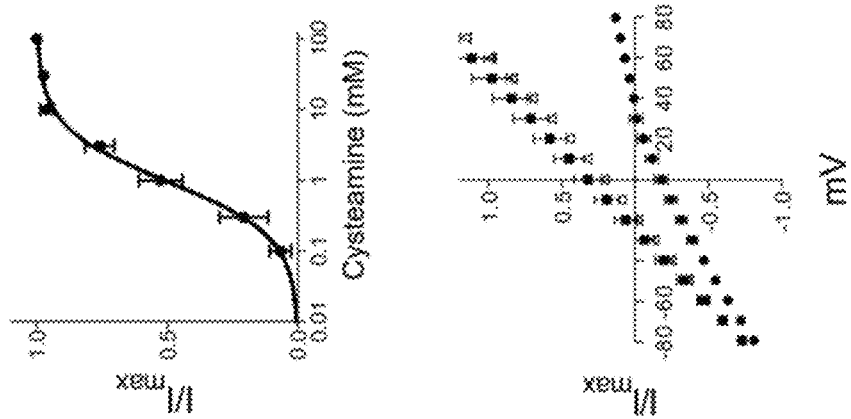
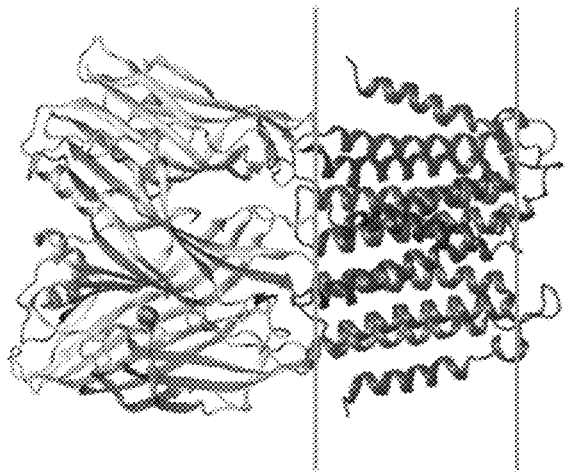
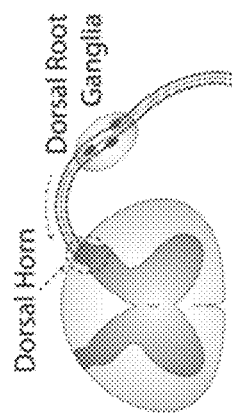
FIG. 8A
FIG. 8B
FIG. 8C
FIG. 8D

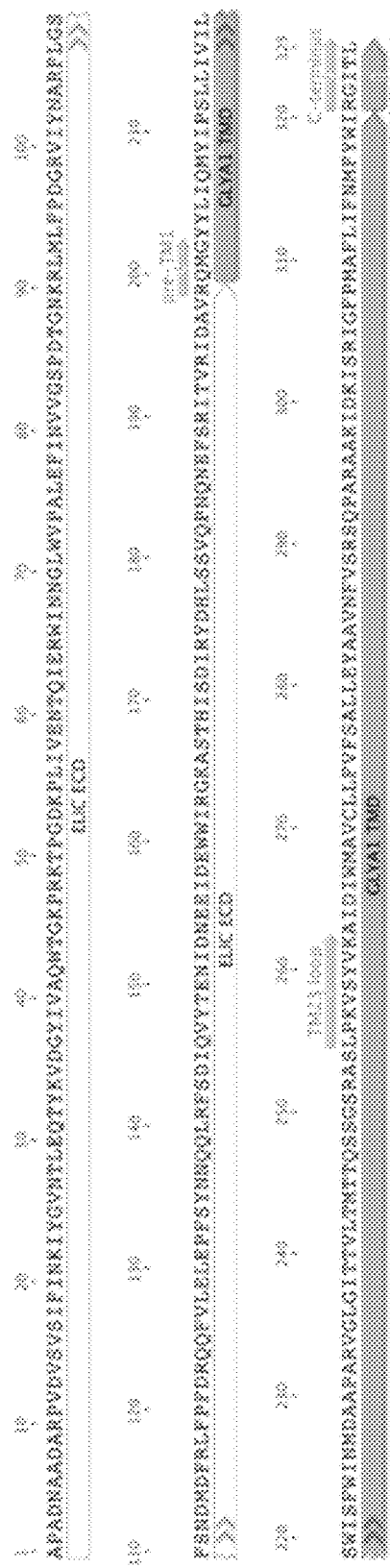
FIG. 11A
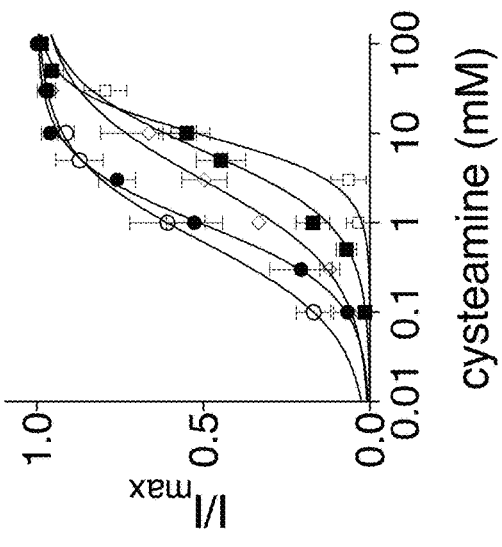
FIG. 11C
| construct | pre-TM1 | TM23 | Cterm | cysteamine EC50(mM) |
|---|---|---|---|---|
| ELIC | RNPS | LPRLPYTT | RGITL | 0.4 |
| GLRA1 | RQMG | LPKVSYVK | IYKIVRREDVHNQ | — |
| EG1 (ID NO 8) | RQMG | LPKVSYVK | IYKIVRREDVHNQ | 6 |
| EG2b (ID NO 11) | RNPS | LPRLPYTT | IYKIVRREDVHNQ | 10 |
| EG2 (ID NO 9) | RNPS | LPKVSYVK | RGITL | 3 |
| EG2a (ID NO 10) | RNPS | LPKVSYVK | RGITL | 0.7 |
| EG3 (ID NO 12) | RQMG | LPKVSYVK | RGITL | 0.9 |
FIG. 11B

                            SEQUENCE LISTING

<160> NUMBER OF SEQ ID NOS: 70

<210> SEQ ID NO 1
<211> LENGTH: 340
<212> TYPE: PRT
<213> ORGANISM: Artificial Sequence
<220> FEATURE:
<223> OTHER INFORMATION: Engineered Chloride Channel Receptor

<400> SEQUENCE: 1

Met Gly Leu Arg Ala Leu Met Leu Trp Leu Leu Ala Ala Ala Gly Leu
1               5                   10                  15

Val Arg Glu Ser Leu Gln Gly Gln Asp Met Val Ser Pro Pro Pro Pro
            20                  25                  30

Ile Ala Asp Glu Pro Leu Thr Val Asn Thr Gly Ile Tyr Leu Ile Glu
        35                  40                  45

Cys Tyr Ser Leu Asp Asp Lys Ala Glu Thr Phe Lys Val Asn Ala Phe
    50                  55                  60

Leu Ser Leu Ser Trp Lys Asp Arg Arg Leu Ala Phe Asp Pro Val Arg
65                  70                  75                  80

Ser Gly Val Arg Val Lys Thr Tyr Glu Pro Glu Ala Ile Trp Ile Pro
                85                  90                  95

Glu Ile Arg Phe Val Asn Val Glu Asn Ala Arg Asp Ala Asp Val Val
            100                 105                 110

Asp Ile Ser Val Ser Pro Asp Gly Thr Val Gln Tyr Leu Glu Arg Phe
        115                 120                 125

Ser Ala Arg Val Leu Ser Pro Leu Asp Phe Arg Arg Tyr Pro Phe Asp
    130                 135                 140

Ser Gln Thr Leu His Ile Tyr Leu Ile Val Arg Ser Val Asp Thr Arg
145                 150                 155                 160

Asn Ile Val Leu Ala Val Asp Leu Glu Lys Val Gly Lys Asn Asp Asp
                165                 170                 175

Val Phe Leu Thr Gly Trp Asp Ile Glu Ser Phe Thr Ala Val Val Lys
            180                 185                 190

Pro Ala Asn Phe Ala Leu Glu Asp Arg Leu Glu Ser Lys Leu Asp Tyr
        195                 200                 205

Gln Leu Arg Ile Ser Arg Gln Met Gly Tyr Tyr Leu Ile Gln Met Tyr
    210                 215                 220

Ile Pro Ser Leu Leu Ile Val Ile Leu Ser Trp Ile Ser Phe Trp Ile
225                 230                 235                 240

Asn Met Asp Ala Ala Pro Ala Arg Val Gly Leu Gly Ile Thr Thr Val
                245                 250                 255

Leu Thr Met Thr Thr Gln Ser Ser Gly Ser Arg Ala Ser Leu Pro Lys
            260                 265                 270

Val Ser Tyr Val Lys Ala Ile Asp Ile Trp Met Ala Val Cys Leu Leu
        275                 280                 285

Phe Val Phe Ser Ala Leu Leu Glu Tyr Ala Ala Val Asn Phe Val Ser
    290                 295                 300

Arg Ser Gln Pro Ala Arg Ala Ala Lys Ile Asp Lys Ile Ser Arg Ile
305                 310                 315                 320

Gly Phe Pro Met Ala Phe Leu Ile Phe Asn Met Phe Tyr Trp Ile Ile
                325                 330                 335
```

-continued

```
Tyr Phe Gly Phe
            340

<210> SEQ ID NO 2
<211> LENGTH: 340
<212> TYPE: PRT
<213> ORGANISM: Artificial Sequence
<220> FEATURE:
<223> OTHER INFORMATION: Engineered Chloride Channel Receptor

<400> SEQUENCE: 2

Met Gly Leu Arg Ala Leu Met Leu Trp Leu Leu Ala Ala Ala Gly Leu
1               5                   10                  15

Val Arg Glu Ser Leu Gln Gly Gln Asp Met Val Ser Pro Pro Pro Pro
            20                  25                  30

Ile Ala Asp Glu Pro Leu Thr Val Asn Thr Gly Ile Tyr Leu Ile Glu
        35                  40                  45

Cys Tyr Ser Leu Asp Asp Lys Ala Glu Thr Phe Lys Val Asn Ala Phe
    50                  55                  60

Leu Ser Leu Ser Trp Lys Asp Arg Arg Leu Ala Phe Asp Pro Val Arg
65                  70                  75                  80

Ser Gly Val Arg Val Lys Thr Tyr Glu Pro Glu Ala Ile Trp Ile Pro
                85                  90                  95

Glu Ile Arg Phe Val Asn Val Glu Asn Ala Arg Asp Ala Asp Val Val
            100                 105                 110

Asp Ile Ser Val Ser Pro Asp Gly Thr Val Gln Tyr Leu Glu Arg Phe
        115                 120                 125

Ser Ala Arg Val Leu Ser Pro Leu Asp Phe Arg Arg Tyr Pro Phe Asp
    130                 135                 140

Ser Gln Thr Leu His Ile Tyr Leu Ile Val Arg Ser Val Asp Thr Arg
145                 150                 155                 160

Asn Ile Val Leu Ala Val Asp Leu Glu Lys Val Gly Lys Asn Asp Asp
                165                 170                 175

Val Phe Leu Thr Gly Trp Asp Ile Glu Ser Phe Thr Ala Val Val Lys
            180                 185                 190

Pro Ala Asn Phe Ala Leu Glu Asp Arg Leu Glu Ser Lys Leu Asp Tyr
        195                 200                 205

Gln Leu Arg Ile Ser Arg Gln Met Gly Tyr Tyr Leu Ile Gln Met Tyr
    210                 215                 220

Ile Pro Ser Leu Leu Ile Val Ile Leu Ser Trp Ile Ser Phe Trp Ile
225                 230                 235                 240

Asn Met Asp Ala Ala Pro Ala Arg Val Gly Leu Gly Ile Thr Thr Val
                245                 250                 255

Leu Thr Met Thr Thr Gln Ser Ile Gly Ser Arg Ala Ser Leu Pro Lys
            260                 265                 270

Val Ser Tyr Val Lys Ala Ile Asp Ile Trp Met Ala Val Cys Leu Leu
        275                 280                 285

Phe Val Phe Ser Ala Leu Leu Glu Tyr Ala Ala Val Asn Phe Val Ser
    290                 295                 300

Arg Ser Gln Pro Ala Arg Ala Ala Lys Ile Asp Lys Ile Ser Arg Ile
305                 310                 315                 320

Gly Phe Pro Met Ala Phe Leu Ile Phe Asn Met Phe Tyr Trp Ile Ile
                325                 330                 335

Tyr Phe Gly Phe
            340
```

```
<210> SEQ ID NO 3
<211> LENGTH: 340
<212> TYPE: PRT
<213> ORGANISM: Artificial Sequence
<220> FEATURE:
<223> OTHER INFORMATION: Engineered Chloride Channel Receptor

<400> SEQUENCE: 3

Met Gly Leu Arg Ala Leu Met Leu Trp Leu Leu Ala Ala Ala Gly Leu
1               5                   10                  15

Val Arg Glu Ser Leu Gln Gly Gln Asp Met Val Ser Pro Pro Pro Pro
            20                  25                  30

Ile Ala Asp Glu Pro Leu Thr Val Asn Thr Gly Ile Tyr Leu Ile Glu
        35                  40                  45

Cys Tyr Ser Leu Asp Asp Lys Ala Glu Thr Phe Lys Val Asn Ala Phe
50                  55                  60

Leu Ser Leu Ser Trp Lys Asp Arg Arg Leu Ala Phe Asp Pro Val Arg
65                  70                  75                  80

Ser Gly Val Arg Val Lys Thr Tyr Glu Pro Glu Ala Ile Trp Ile Pro
                85                  90                  95

Glu Ile Arg Phe Val Asn Val Glu Asn Ala Arg Asp Ala Asp Val Val
            100                 105                 110

Asp Ile Ser Val Ser Pro Asp Gly Thr Val Gln Tyr Leu Glu Arg Phe
        115                 120                 125

Ser Ala Arg Val Leu Ser Pro Leu Asp Phe Arg Arg Tyr Pro Phe Asp
    130                 135                 140

Ser Gln Thr Leu His Ile Tyr Leu Ile Val Arg Ser Val Asp Thr Arg
145                 150                 155                 160

Asn Ile Val Leu Ala Val Asp Leu Glu Lys Val Gly Lys Asn Asp Asp
                165                 170                 175

Val Phe Leu Thr Gly Trp Asp Ile Glu Ser Phe Thr Ala Val Val Lys
            180                 185                 190

Pro Ala Asn Phe Ala Leu Glu Asp Arg Leu Glu Ser Lys Leu Asp Tyr
        195                 200                 205

Gln Leu Arg Ile Ser Arg Gln Met Gly Tyr Tyr Leu Ile Gln Met Tyr
    210                 215                 220

Ile Pro Ser Leu Leu Ile Val Ile Leu Ser Trp Ile Ser Phe Trp Ile
225                 230                 235                 240

Asn Met Asp Ala Ala Pro Ala Arg Val Gly Leu Gly Ile Thr Thr Val
                245                 250                 255

Leu Thr Met Thr Thr Gln Ser Val Gly Ser Arg Ala Ser Leu Pro Lys
            260                 265                 270

Val Ser Tyr Val Lys Ala Ile Asp Ile Trp Met Ala Val Cys Leu Leu
        275                 280                 285

Phe Val Phe Ser Ala Leu Leu Glu Tyr Ala Ala Val Asn Phe Val Ser
    290                 295                 300

Arg Ser Gln Pro Ala Arg Ala Ala Lys Ile Asp Lys Ile Ser Arg Ile
305                 310                 315                 320

Gly Phe Pro Met Ala Phe Leu Ile Phe Asn Met Phe Tyr Trp Ile Ile
                325                 330                 335

Tyr Phe Gly Phe
            340

<210> SEQ ID NO 4
```

```
<211> LENGTH: 340
<212> TYPE: PRT
<213> ORGANISM: Artificial Sequence
<220> FEATURE:
<223> OTHER INFORMATION: Engineered Chloride Channel Receptor

<400> SEQUENCE: 4
```

Met Gly Leu Arg Ala Leu Met Leu Trp Leu Leu Ala Ala Ala Gly Leu
1               5                   10                  15

Val Arg Glu Ser Leu Gln Gly Gln Asp Met Val Ser Pro Pro Pro Pro
            20                  25                  30

Ile Ala Asp Glu Pro Leu Thr Val Asn Thr Gly Ile Tyr Leu Ile Glu
        35                  40                  45

Cys Tyr Ser Leu Asp Asp Lys Ala Glu Thr Phe Lys Val Asn Ala Phe
    50                  55                  60

Leu Ser Leu Ser Trp Lys Asp Arg Arg Leu Ala Phe Asp Pro Val Arg
65                  70                  75                  80

Ser Gly Val Arg Val Lys Thr Tyr Glu Pro Glu Ala Ile Trp Ile Pro
                85                  90                  95

Glu Ile Arg Phe Val Asn Val Glu Asn Ala Arg Asp Ala Asp Val Val
            100                 105                 110

Asp Ile Ser Val Ser Pro Asp Gly Thr Val Gln Tyr Leu Glu Arg Phe
        115                 120                 125

Ser Ala Arg Val Leu Ser Pro Leu Asp Phe Arg Arg Tyr Pro Phe Asp
    130                 135                 140

Ser Gln Thr Leu His Ile Tyr Leu Ile Val Arg Ser Val Asp Thr Arg
145                 150                 155                 160

Asn Ile Val Leu Ala Val Asp Leu Glu Lys Val Gly Lys Asn Asp Asp
                165                 170                 175

Val Phe Leu Thr Gly Trp Asp Ile Glu Ser Phe Thr Ala Val Val Lys
            180                 185                 190

Pro Ala Asn Phe Ala Leu Glu Asp Arg Leu Glu Ser Lys Leu Asp Tyr
        195                 200                 205

Gln Leu Arg Ile Ser Arg Gln Met Gly Tyr Tyr Leu Ile Gln Met Tyr
    210                 215                 220

Ile Pro Ser Leu Leu Ile Val Ile Leu Ser Trp Ile Ser Phe Trp Ile
225                 230                 235                 240

Asn Met Asp Ala Ala Pro Ala Arg Val Gly Leu Gly Ile Thr Thr Val
                245                 250                 255

Leu Thr Met Thr Thr Gln Ser Ala Gly Ser Arg Ala Ser Leu Pro Lys
            260                 265                 270

Val Ser Tyr Val Lys Ala Ile Asp Ile Trp Met Ala Val Cys Leu Leu
        275                 280                 285

Phe Val Phe Ser Ala Leu Leu Glu Tyr Ala Ala Val Asn Phe Val Ser
    290                 295                 300

Arg Ser Gln Pro Ala Arg Ala Ala Lys Ile Asp Lys Ile Ser Arg Ile
305                 310                 315                 320

Gly Phe Pro Met Ala Phe Leu Ile Phe Asn Met Phe Tyr Trp Ile Ile
                325                 330                 335

Tyr Phe Gly Phe
            340

```
<210> SEQ ID NO 5
<211> LENGTH: 340
<212> TYPE: PRT
<213> ORGANISM: Artificial Sequence
```

<220> FEATURE:
<223> OTHER INFORMATION: Engineered Chloride Channel Receptor

<400> SEQUENCE: 5

```
Met Gly Leu Arg Ala Leu Met Leu Trp Leu Ala Ala Gly Leu
1               5                   10                  15

Val Arg Glu Ser Leu Gln Gly Gln Asp Met Val Ser Pro Pro Pro
            20                  25                  30

Ile Ala Asp Glu Pro Leu Thr Val Asn Thr Gly Ile Tyr Leu Ile Glu
        35                  40                  45

Cys Tyr Ser Ile Ala Glu Thr Thr Met Thr Phe Lys Val Asn Ala Phe
    50                  55                  60

Leu Ser Leu Ser Trp Lys Asp Arg Arg Leu Ala Phe Asp Pro Val Arg
65                  70                  75                  80

Ser Gly Val Arg Val Lys Thr Tyr Glu Pro Glu Ala Ile Trp Ile Pro
                85                  90                  95

Glu Ile Arg Phe Val Asn Val Glu Asn Ala Arg Asp Ala Asp Val Val
            100                 105                 110

Asp Ile Ser Val Ser Pro Asp Gly Thr Val Gln Tyr Leu Glu Arg Phe
        115                 120                 125

Ser Ala Arg Val Leu Ser Pro Leu Asp Leu Lys Asn Phe Pro Met Asp
130                 135                 140

Ser Gln Thr Leu His Ile Tyr Leu Ile Val Arg Ser Val Asp Thr Arg
145                 150                 155                 160

Asn Ile Val Leu Ala Val Asp Leu Glu Lys Val Gly Lys Asn Asp Asp
                165                 170                 175

Val Phe Leu Thr Gly Trp Asp Ile Glu Ser Phe Thr Asp Gly Leu Thr
            180                 185                 190

Leu Pro Gln Phe Ala Leu Glu Asp Arg Leu Glu Ser Lys Leu Asp Tyr
        195                 200                 205

Gln Leu Arg Ile Ser Arg Gln Met Gly Tyr Tyr Leu Ile Gln Met Tyr
210                 215                 220

Ile Pro Ser Leu Leu Ile Val Ile Leu Ser Trp Ile Ser Phe Trp Ile
225                 230                 235                 240

Asn Met Asp Ala Ala Pro Ala Arg Val Gly Leu Gly Ile Thr Thr Val
                245                 250                 255

Leu Thr Met Thr Thr Gln Ser Val Gly Ser Arg Ala Ser Leu Pro Lys
            260                 265                 270

Val Ser Tyr Val Lys Ala Ile Asp Ile Trp Met Ala Val Cys Leu Leu
        275                 280                 285

Phe Val Phe Ser Ala Leu Leu Glu Tyr Ala Ala Val Asn Phe Val Ser
290                 295                 300

Arg Ser Gln Pro Ala Arg Ala Ala Lys Ile Asp Lys Ile Ser Arg Ile
305                 310                 315                 320

Gly Phe Pro Met Ala Phe Leu Ile Phe Asn Met Phe Tyr Trp Ile Ile
                325                 330                 335

Tyr Phe Gly Phe
            340
```

<210> SEQ ID NO 6
<211> LENGTH: 348
<212> TYPE: PRT
<213> ORGANISM: Artificial Sequence
<220> FEATURE:
<223> OTHER INFORMATION: Engineered Chloride Channel Receptor

<400> SEQUENCE: 6

```
Met Gly Leu Arg Ala Leu Met Leu Trp Leu Leu Ala Ala Ala Gly Leu
1               5                   10                  15

Val Arg Glu Ser Leu Gln Gly Gln Asp Met Val Ser Pro Pro Pro Pro
            20                  25                  30

Ile Ala Asp Glu Pro Leu Thr Val Asn Thr Gly Ile Tyr Leu Ile Glu
        35                  40                  45

Cys Tyr Ser Ile Ala Glu Thr Thr Met Thr Phe Lys Val Asn Ala Phe
    50                  55                  60

Leu Ser Leu Ser Trp Lys Asp Arg Arg Leu Ala Phe Asp Pro Val Arg
65                  70                  75                  80

Ser Gly Val Arg Val Lys Thr Tyr Glu Pro Glu Ala Ile Trp Ile Pro
                85                  90                  95

Glu Ile Arg Phe Val Asn Val Glu Asn Ala Arg Asp Ala Asp Val Val
            100                 105                 110

Asp Ile Ser Val Ser Pro Asp Gly Thr Val Gln Tyr Leu Glu Arg Phe
        115                 120                 125

Ser Ala Arg Val Leu Ser Pro Leu Asp Leu Lys Asn Phe Pro Met Asp
    130                 135                 140

Ser Gln Thr Leu His Ile Tyr Leu Ile Val Arg Ser Val Asp Thr Arg
145                 150                 155                 160

Asn Ile Val Leu Ala Val Asp Leu Glu Lys Val Gly Lys Asn Asp Asp
                165                 170                 175

Val Phe Leu Thr Gly Trp Asp Ile Glu Ser Phe Thr Asp Gly Leu Thr
            180                 185                 190

Leu Pro Gln Phe Ala Leu Glu Asp Arg Leu Glu Ser Lys Leu Asp Tyr
        195                 200                 205

Gln Leu Arg Ile Ser Arg Gln Met Gly Tyr Tyr Leu Ile Gln Met Tyr
    210                 215                 220

Ile Pro Ser Leu Leu Ile Val Ile Leu Ser Trp Ile Ser Phe Trp Ile
225                 230                 235                 240

Asn Met Asp Ala Ala Pro Ala Arg Val Gly Leu Gly Ile Thr Thr Val
                245                 250                 255

Leu Thr Met Thr Thr Gln Ser Val Gly Ser Arg Ala Ser Leu Pro Lys
            260                 265                 270

Val Ser Tyr Val Lys Ala Ile Asp Ile Trp Met Ala Val Cys Leu Leu
        275                 280                 285

Phe Val Phe Ser Ala Leu Leu Glu Tyr Ala Ala Val Asn Phe Val Ser
    290                 295                 300

Arg Ser Gln Pro Ala Arg Ala Ala Lys Ile Asp Lys Ile Ser Arg Ile
305                 310                 315                 320

Gly Phe Pro Met Ala Phe Leu Ile Phe Asn Met Phe Tyr Trp Ile Ile
                325                 330                 335

Tyr Lys Ile Val Arg Arg Glu Asp Val His Asn Gln
            340                 345
```

<210> SEQ ID NO 7
<211> LENGTH: 340
<212> TYPE: PRT
<213> ORGANISM: Artificial Sequence
<220> FEATURE:
<223> OTHER INFORMATION: Engineered Chloride Channel Receptor

<400> SEQUENCE: 7

Met Gly Leu Arg Ala Leu Met Leu Trp Leu Leu Ala Ala Ala Gly Leu

```
            1               5                  10                 15
          Val Arg Glu Ser Leu Gln Gly Gln Asp Met Val Ser Pro Pro Pro
                          20                 25                 30
          Ile Ala Asp Glu Pro Leu Thr Val Asn Thr Gly Ile Tyr Leu Ile Glu
                          35                 40                 45
          Cys Tyr Ser Leu Asp Asp Lys Ala Glu Thr Phe Lys Val Asn Ala Phe
              50                  55                  60
          Leu Ser Leu Ser Trp Lys Asp Arg Arg Leu Ala Phe Asp Pro Val Arg
          65                  70                  75                  80
          Ser Gly Val Arg Val Lys Thr Tyr Glu Pro Glu Ala Ile Trp Ile Pro
                          85                  90                  95
          Glu Ile Arg Phe Val Asn Val Glu Asn Ala Arg Asp Ala Asp Val Val
                         100                 105                 110
          Asp Ile Ser Val Ser Pro Asp Gly Thr Val Gln Tyr Leu Glu Arg Phe
                         115                 120                 125
          Ser Ala Arg Val Leu Ser Pro Leu Asp Phe Arg Arg Tyr Pro Phe Asp
                         130                 135                 140
          Ser Gln Thr Leu His Ile Tyr Leu Ile Val Arg Ser Val Asp Thr Arg
          145                 150                 155                 160
          Asn Ile Val Leu Ala Val Asp Leu Glu Lys Val Gly Lys Asn Asp Asp
                         165                 170                 175
          Val Phe Leu Thr Gly Trp Asp Ile Glu Ser Phe Thr Ala Val Val Lys
                         180                 185                 190
          Pro Ala Asn Phe Ala Leu Glu Asp Arg Leu Glu Ser Lys Leu Asp Tyr
                         195                 200                 205
          Gln Leu Arg Ile Ser Arg Gln Met Gly Tyr Tyr Leu Ile Gln Met Tyr
                         210                 215                 220
          Ile Pro Ser Leu Leu Ile Val Ile Leu Ser Trp Ile Ser Phe Trp Ile
          225                 230                 235                 240
          Asn Met Asp Ala Ala Pro Ala Arg Val Gly Leu Gly Ile Thr Thr Val
                         245                 250                 255
          Leu Thr Met Thr Thr Gln Ser Val Gly Ser Arg Thr Asn Leu Pro Lys
                         260                 265                 270
          Thr Pro Tyr Val Lys Ala Ile Asp Ile Trp Met Ala Val Cys Leu Leu
                         275                 280                 285
          Phe Val Phe Ser Ala Leu Leu Glu Tyr Ala Ala Val Asn Phe Val Ser
                         290                 295                 300
          Arg Ser Gln Pro Ala Arg Ala Ala Lys Ile Asp Lys Ile Ser Arg Ile
          305                 310                 315                 320
          Gly Phe Pro Met Ala Phe Leu Ile Phe Asn Met Phe Tyr Trp Ile Ile
                         325                 330                 335
          Tyr Phe Gly Phe
                         340

<210> SEQ ID NO 8
<211> LENGTH: 355
<212> TYPE: PRT
<213> ORGANISM: Artificial Sequence
<220> FEATURE:
<223> OTHER INFORMATION: Engineered Chloride Channel Receptor

<400> SEQUENCE: 8

Met Gly Leu Arg Ala Leu Met Leu Trp Leu Leu Ala Ala Ala Gly Leu
1               5                  10                  15

Val Arg Glu Ser Leu Gln Ala Pro Ala Asp Asn Ala Ala Asp Ala Arg
```

```
            20                  25                  30
Pro Val Asp Val Ser Val Ser Ile Phe Ile Asn Lys Ile Tyr Gly Val
        35                  40                  45

Asn Thr Leu Glu Gln Thr Tyr Lys Val Asp Gly Tyr Ile Val Ala Gln
    50                  55                  60

Trp Thr Gly Lys Pro Arg Lys Thr Pro Gly Asp Lys Pro Leu Ile Val
65                  70                  75                  80

Glu Asn Thr Gln Ile Glu Arg Trp Ile Asn Asn Gly Leu Trp Val Pro
                85                  90                  95

Ala Leu Glu Phe Ile Asn Val Val Gly Ser Pro Asp Thr Gly Asn Lys
            100                 105                 110

Arg Leu Met Leu Phe Pro Asp Gly Arg Val Ile Tyr Asn Ala Arg Phe
        115                 120                 125

Leu Gly Ser Phe Ser Asn Asp Met Asp Phe Arg Leu Phe Pro Phe Asp
    130                 135                 140

Arg Gln Gln Phe Val Leu Glu Leu Glu Pro Phe Ser Tyr Asn Asn Gln
145                 150                 155                 160

Gln Leu Arg Phe Ser Asp Ile Gln Val Tyr Thr Glu Asn Ile Asp Asn
                165                 170                 175

Glu Glu Ile Asp Glu Trp Trp Ile Arg Gly Lys Ala Ser Thr His Ile
            180                 185                 190

Ser Asp Ile Arg Tyr Asp His Leu Ser Ser Val Gln Pro Asn Gln Asn
        195                 200                 205

Glu Phe Ser Arg Ile Thr Val Arg Ile Asp Ala Val Arg Gln Met Gly
    210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                245                 250                 255

Gly Leu Gly Ile Thr Thr Val Leu Thr Met Thr Thr Gln Ser Ser Gly
            260                 265                 270

Ser Arg Ala Ser Leu Pro Lys Val Ser Tyr Val Lys Ala Ile Asp Ile
        275                 280                 285

Trp Met Ala Val Cys Leu Leu Phe Val Phe Ser Ala Leu Leu Glu Tyr
    290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                325                 330                 335

Asn Met Phe Tyr Trp Ile Ile Tyr Lys Ile Val Arg Arg Glu Asp Val
            340                 345                 350

His Asn Gln
        355

<210> SEQ ID NO 9
<211> LENGTH: 347
<212> TYPE: PRT
<213> ORGANISM: Artificial Sequence
<220> FEATURE:
<223> OTHER INFORMATION: Engineered Chloride Channel Receptor

<400> SEQUENCE: 9

Met Gly Leu Arg Ala Leu Met Leu Trp Leu Leu Ala Ala Ala Gly Leu
1               5                   10                  15

Val Arg Glu Ser Leu Gln Ala Pro Ala Asp Asn Ala Ala Asp Ala Arg
```

```
            20                  25                  30
Pro Val Asp Val Ser Val Ser Ile Phe Ile Asn Lys Ile Tyr Gly Val
            35                  40                  45

Asn Thr Leu Glu Gln Thr Tyr Lys Val Asp Gly Tyr Ile Val Ala Gln
     50                  55                  60

Trp Thr Gly Lys Pro Arg Lys Thr Pro Gly Asp Lys Pro Leu Ile Val
 65                  70                  75                  80

Glu Asn Thr Gln Ile Glu Arg Trp Ile Asn Asn Gly Leu Trp Val Pro
                 85                  90                  95

Ala Leu Glu Phe Ile Asn Val Val Gly Ser Pro Asp Thr Gly Asn Lys
            100                 105                 110

Arg Leu Met Leu Phe Pro Asp Gly Arg Val Ile Tyr Asn Ala Arg Phe
            115                 120                 125

Leu Gly Ser Phe Ser Asn Asp Met Asp Phe Arg Leu Phe Pro Phe Asp
            130                 135                 140

Arg Gln Gln Phe Val Leu Glu Leu Glu Pro Phe Ser Tyr Asn Asn Gln
145                 150                 155                 160

Gln Leu Arg Phe Ser Asp Ile Gln Val Tyr Thr Glu Asn Ile Asp Asn
                165                 170                 175

Glu Glu Ile Asp Glu Trp Trp Ile Arg Gly Lys Ala Ser Thr His Ile
            180                 185                 190

Ser Asp Ile Arg Tyr Asp His Leu Ser Ser Val Gln Pro Asn Gln Asn
            195                 200                 205

Glu Phe Ser Arg Ile Thr Val Arg Ile Asp Ala Gly Arg Asn Pro Ser
            210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                245                 250                 255

Gly Leu Gly Ile Thr Thr Val Leu Thr Met Thr Thr Gln Ser Ser Gly
            260                 265                 270

Ser Arg Ala Ser Leu Pro Arg Leu Pro Tyr Thr Thr Val Ile Asp Ile
            275                 280                 285

Trp Met Ala Val Cys Leu Leu Phe Val Phe Ser Ala Leu Leu Glu Tyr
            290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                325                 330                 335

Asn Met Phe Tyr Trp Ile Arg Gly Ile Thr Leu
                340                 345

<210> SEQ ID NO 10
<211> LENGTH: 347
<212> TYPE: PRT
<213> ORGANISM: Artificial Sequence
<220> FEATURE:
<223> OTHER INFORMATION: Engineered Chloride Channel Receptor

<400> SEQUENCE: 10

Met Gly Leu Arg Ala Leu Met Leu Trp Leu Leu Ala Ala Ala Gly Leu
 1               5                  10                  15

Val Arg Glu Ser Leu Gln Ala Pro Ala Asp Asn Ala Ala Asp Ala Arg
             20                  25                  30

Pro Val Asp Val Ser Val Ser Ile Phe Ile Asn Lys Ile Tyr Gly Val
```

```
                35                  40                  45
Asn Thr Leu Glu Gln Thr Tyr Lys Val Asp Gly Tyr Ile Val Ala Gln
 50                  55                  60

Trp Thr Gly Lys Pro Arg Lys Thr Pro Gly Asp Lys Pro Leu Ile Val
 65                  70                  75                  80

Glu Asn Thr Gln Ile Glu Arg Trp Ile Asn Asn Gly Leu Trp Val Pro
                 85                  90                  95

Ala Leu Glu Phe Ile Asn Val Val Gly Ser Pro Asp Thr Gly Asn Lys
            100                 105                 110

Arg Leu Met Leu Phe Pro Asp Gly Arg Val Ile Tyr Asn Ala Arg Phe
        115                 120                 125

Leu Gly Ser Phe Ser Asn Asp Met Asp Phe Arg Leu Phe Pro Phe Asp
    130                 135                 140

Arg Gln Gln Phe Val Leu Glu Leu Glu Pro Phe Ser Tyr Asn Asn Gln
145                 150                 155                 160

Gln Leu Arg Phe Ser Asp Ile Gln Val Tyr Thr Glu Asn Ile Asp Asn
                165                 170                 175

Glu Glu Ile Asp Glu Trp Trp Ile Arg Gly Lys Ala Ser Thr His Ile
            180                 185                 190

Ser Asp Ile Arg Tyr Asp His Leu Ser Ser Val Gln Pro Asn Gln Asn
        195                 200                 205

Glu Phe Ser Arg Ile Thr Val Arg Ile Asp Ala Val Arg Gln Met Gly
    210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                245                 250                 255

Gly Leu Gly Ile Thr Thr Val Leu Thr Met Thr Thr Gln Ser Ser Gly
            260                 265                 270

Ser Arg Ala Ser Leu Pro Arg Leu Pro Tyr Thr Thr Val Ile Asp Ile
        275                 280                 285

Trp Met Ala Val Cys Leu Leu Phe Val Phe Ser Ala Leu Leu Glu Tyr
    290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                325                 330                 335

Asn Met Phe Tyr Trp Ile Arg Gly Ile Thr Leu
            340                 345

<210> SEQ ID NO 11
<211> LENGTH: 355
<212> TYPE: PRT
<213> ORGANISM: Artificial Sequence
<220> FEATURE:
<223> OTHER INFORMATION: Engineered Chloride Channel Receptor

<400> SEQUENCE: 11

Met Gly Leu Arg Ala Leu Met Leu Trp Leu Leu Ala Ala Ala Gly Leu
1               5                   10                  15

Val Arg Glu Ser Leu Gln Ala Pro Ala Asp Asn Ala Ala Asp Ala Arg
                20                  25                  30

Pro Val Asp Val Ser Val Ser Ile Phe Ile Asn Lys Ile Tyr Gly Val
            35                  40                  45

Asn Thr Leu Glu Gln Thr Tyr Lys Val Asp Gly Tyr Ile Val Ala Gln
```

```
                    50                  55                  60
Trp Thr Gly Lys Pro Arg Lys Thr Pro Gly Asp Lys Pro Leu Ile Val
 65                  70                  75                  80

Glu Asn Thr Gln Ile Glu Arg Trp Ile Asn Asn Gly Leu Trp Val Pro
                     85                  90                  95

Ala Leu Glu Phe Ile Asn Val Val Gly Ser Pro Asp Thr Gly Asn Lys
                    100                 105                 110

Arg Leu Met Leu Phe Pro Asp Gly Arg Val Ile Tyr Asn Ala Arg Phe
                115                 120                 125

Leu Gly Ser Phe Ser Asn Asp Met Asp Phe Arg Leu Phe Pro Phe Asp
            130                 135                 140

Arg Gln Gln Phe Val Leu Glu Leu Glu Pro Phe Ser Tyr Asn Asn Gln
145                 150                 155                 160

Gln Leu Arg Phe Ser Asp Ile Gln Val Tyr Thr Glu Asn Ile Asp Asn
                165                 170                 175

Glu Glu Ile Asp Glu Trp Trp Ile Arg Gly Lys Ala Ser Thr His Ile
            180                 185                 190

Ser Asp Ile Arg Tyr Asp His Leu Ser Ser Val Gln Pro Asn Gln Asn
        195                 200                 205

Glu Phe Ser Arg Ile Thr Val Arg Ile Asp Ala Val Arg Asn Pro Ser
    210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                245                 250                 255

Gly Leu Gly Ile Thr Thr Val Leu Thr Met Thr Thr Gln Ser Ser Gly
            260                 265                 270

Ser Arg Ala Ser Leu Pro Arg Leu Pro Tyr Thr Thr Val Ile Asp Ile
        275                 280                 285

Trp Met Ala Val Cys Leu Leu Phe Val Phe Ser Ala Leu Leu Glu Tyr
    290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                325                 330                 335

Asn Met Phe Tyr Trp Ile Ile Tyr Lys Ile Val Arg Arg Glu Asp Val
            340                 345                 350

His Asn Gln
        355

<210> SEQ ID NO 12
<211> LENGTH: 347
<212> TYPE: PRT
<213> ORGANISM: Artificial Sequence
<220> FEATURE:
<223> OTHER INFORMATION: Engineered Chloride Channel Receptor

<400> SEQUENCE: 12

Met Gly Leu Arg Ala Leu Met Leu Trp Leu Leu Ala Ala Ala Gly Leu
  1               5                  10                  15

Val Arg Glu Ser Leu Gln Ala Pro Ala Asp Asn Ala Ala Asp Ala Arg
                 20                  25                  30

Pro Val Asp Val Ser Val Ser Ile Phe Ile Asn Lys Ile Tyr Gly Val
             35                  40                  45

Asn Thr Leu Glu Gln Thr Tyr Lys Val Asp Gly Tyr Ile Val Ala Gln
```

```
                 50                  55                  60
Trp Thr Gly Lys Pro Arg Lys Thr Pro Gly Asp Lys Pro Leu Ile Val
 65                  70                  75                  80

Glu Asn Thr Gln Ile Glu Arg Trp Ile Asn Asn Gly Leu Trp Val Pro
                 85                  90                  95

Ala Leu Glu Phe Ile Asn Val Val Gly Ser Pro Asp Thr Gly Asn Lys
                100                 105                 110

Arg Leu Met Leu Phe Pro Asp Gly Arg Val Ile Tyr Asn Ala Arg Phe
                115                 120                 125

Leu Gly Ser Phe Ser Asn Asp Met Asp Phe Arg Leu Phe Pro Phe Asp
            130                 135                 140

Arg Gln Gln Phe Val Leu Glu Leu Glu Pro Phe Ser Tyr Asn Asn Gln
145                 150                 155                 160

Gln Leu Arg Phe Ser Asp Ile Gln Val Tyr Thr Glu Asn Ile Asp Asn
                165                 170                 175

Glu Glu Ile Asp Glu Trp Trp Ile Arg Gly Lys Ala Ser Thr His Ile
                180                 185                 190

Ser Asp Ile Arg Tyr Asp His Leu Ser Ser Val Gln Pro Asn Gln Asn
            195                 200                 205

Glu Phe Ser Arg Ile Thr Val Arg Ile Asp Ala Val Arg Gln Met Gly
                210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                245                 250                 255

Gly Leu Gly Ile Thr Thr Val Leu Thr Met Thr Thr Gln Ser Ser Gly
            260                 265                 270

Ser Arg Ala Ser Leu Pro Lys Val Ser Tyr Val Lys Ala Ile Asp Ile
                275                 280                 285

Trp Met Ala Val Cys Leu Leu Phe Val Phe Ser Ala Leu Leu Glu Tyr
            290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                325                 330                 335

Asn Met Phe Tyr Trp Ile Arg Gly Ile Thr Leu
                340                 345

<210> SEQ ID NO 13
<211> LENGTH: 347
<212> TYPE: PRT
<213> ORGANISM: Artificial Sequence
<220> FEATURE:
<223> OTHER INFORMATION: Engineered Chloride Channel Receptor

<400> SEQUENCE: 13

Met Gly Leu Arg Ala Leu Met Leu Trp Leu Ala Ala Ala Gly Leu
  1               5                  10                  15

Val Arg Glu Ser Leu Gln Ala Pro Ala Asp Asn Ala Ala Asp Ala Arg
                 20                  25                  30

Pro Val Asp Val Ser Val Ser Ile Phe Ile Asn Lys Ile Tyr Gly Val
                 35                  40                  45

Asn Thr Leu Glu Gln Thr Tyr Lys Val Asp Gly Trp Ile Val Ala Gln
                 50                  55                  60

Trp Thr Gly Lys Pro Arg Lys Thr Pro Gly Asp Lys Pro Leu Ile Val
```

```
            65                  70                  75                  80
Glu Asn Thr Gln Ile Glu Arg Trp Ile Asn Asn Gly Leu Trp Val Pro
                85                  90                  95

Ala Leu Glu Phe Tyr Asn Val Val Gly Ser Pro Asp Thr Gly Asn Lys
            100                 105                 110

Arg Leu Met Leu Phe Pro Asp Gly Arg Val Ile Tyr Asn Ala Arg Phe
        115                 120                 125

Leu Gly Ser Phe Ser Asn Asp Met Asp Phe Arg Leu Phe Pro Phe Asp
    130                 135                 140

Arg Gln Gln Phe Val Leu Glu Leu Glu Pro Trp Ser Tyr Asn Asn Gln
145                 150                 155                 160

Gln Leu Arg Phe Ser Asp Ile Gln Val Tyr Thr Glu Asn Ile Asp Asn
                165                 170                 175

Glu Glu Ile Asp Glu Trp Trp Ile Arg Gly Lys Ala Ser Thr His Ile
            180                 185                 190

Ser Asp Ile Arg Tyr Asp His Leu Ser Ser Val Gln Pro Asn Gln Asn
        195                 200                 205

Glu Tyr Ser Arg Ile Thr Val Arg Ile Asp Ala Val Arg Gln Met Gly
    210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                245                 250                 255

Gly Leu Gly Ile Thr Thr Val Leu Thr Met Thr Thr Gln Ser Ser Gly
            260                 265                 270

Ser Arg Ala Ser Leu Pro Lys Val Ser Tyr Val Lys Ala Ile Asp Ile
        275                 280                 285

Trp Met Ala Val Cys Leu Leu Phe Val Phe Ser Ala Leu Leu Glu Tyr
    290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                325                 330                 335

Asn Met Phe Tyr Trp Ile Arg Gly Ile Thr Leu
            340                 345
```

<210> SEQ ID NO 14
<211> LENGTH: 355
<212> TYPE: PRT
<213> ORGANISM: Artificial Sequence
<220> FEATURE:
<223> OTHER INFORMATION: Engineered Chloride Channel Receptor

<400> SEQUENCE: 14

```
Met Gly Leu Arg Ala Leu Met Leu Trp Leu Leu Ala Ala Ala Gly Leu
1               5                   10                  15

Val Arg Glu Ser Leu Gln Ala Pro Ala Asp Asn Ala Ala Asp Ala Arg
            20                  25                  30

Pro Val Asp Val Ser Val Ser Ile Phe Ile Asn Lys Ile Tyr Gly Ile
        35                  40                  45

Ala Glu Thr Thr Met Thr Tyr Lys Val Asp Gly Tyr Ile Val Ala Gln
    50                  55                  60

Trp Thr Gly Lys Pro Arg Lys Thr Pro Gly Asp Lys Pro Leu Ile Val
65                  70                  75                  80

Glu Asn Thr Gln Ile Glu Arg Trp Ile Asn Asn Gly Leu Trp Val Pro
```

```
                    85                  90                  95
Ala Leu Glu Phe Ile Asn Val Val Gly Ser Pro Asp Thr Gly Asn Lys
            100                 105                 110

Arg Leu Met Leu Phe Pro Asp Gly Arg Val Ile Tyr Asn Ala Arg Phe
            115                 120                 125

Leu Gly Ser Phe Ser Asn Asp Met Asp Leu Lys Asn Phe Pro Met Asp
            130                 135                 140

Arg Gln Gln Phe Val Leu Glu Leu Pro Phe Ser Tyr Asn Asn Gln
145                 150                 155                 160

Gln Leu Arg Phe Ser Asp Ile Gln Val Tyr Thr Glu Asn Ile Asp Gly
                165                 170                 175

Leu Thr Leu Pro Gln Phe Trp Ile Arg Gly Lys Ala Ser Thr His Ile
            180                 185                 190

Ser Asp Ile Arg Tyr Asp His Leu Ser Ser Val Gln Pro Asn Gln Asn
            195                 200                 205

Glu Phe Ser Arg Ile Thr Val Arg Ile Asp Ala Val Arg Gln Met Gly
            210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                245                 250                 255

Gly Leu Gly Ile Thr Thr Val Leu Thr Met Thr Thr Gln Ser Ser Gly
            260                 265                 270

Ser Arg Ala Ser Leu Pro Lys Val Ser Tyr Val Lys Ala Ile Asp Ile
            275                 280                 285

Trp Met Ala Val Cys Leu Leu Phe Val Phe Ser Ala Leu Leu Glu Tyr
            290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                325                 330                 335

Asn Met Phe Tyr Trp Ile Ile Tyr Lys Ile Val Arg Arg Glu Asp Val
            340                 345                 350

His Asn Gln
        355

<210> SEQ ID NO 15
<211> LENGTH: 347
<212> TYPE: PRT
<213> ORGANISM: Artificial Sequence
<220> FEATURE:
<223> OTHER INFORMATION: Engineered Chloride Channel Receptor

<400> SEQUENCE: 15

Met Gly Leu Arg Ala Leu Met Leu Trp Leu Leu Ala Ala Ala Gly Leu
1               5                   10                  15

Val Arg Glu Ser Leu Gln Ala Pro Ala Asp Asn Ala Ala Asp Ala Arg
            20                  25                  30

Pro Val Asp Val Ser Val Ser Ile Phe Ile Asn Lys Ile Tyr Gly Val
        35                  40                  45

Asn Thr Leu Glu Gln Thr Tyr Lys Val Asp Gly Tyr Ile Val Ala Gln
        50                  55                  60

Trp Thr Gly Lys Pro Arg Lys Thr Pro Gly Asp Lys Pro Leu Ile Val
65              70                  75                  80

Glu Asn Thr Gln Ile Glu Arg Trp Ile Asn Asn Gly Leu Trp Val Pro
```

```
            85                  90                  95
Ala Leu Glu Phe Ile Asn Val Val Gly Ser Pro Asp Thr Gly Asn Lys
            100                 105                 110

Ala Leu Met Leu Phe Pro Asp Gly Arg Val Ile Tyr Asn Ala Arg Phe
            115                 120                 125

Leu Gly Ser Phe Ser Asn Asp Met Asp Phe Arg Leu Phe Pro Phe Asp
            130                 135                 140

Arg Gln Gln Phe Val Leu Glu Leu Glu Pro Phe Ser Tyr Asn Asn Gln
145                 150                 155                 160

Gln Leu Arg Phe Ser Asp Ile Gln Val Tyr Thr Glu Asn Ile Asp Asn
                    165                 170                 175

Glu Glu Ile Asp Glu Trp Trp Ile Arg Gly Lys Ala Ser Thr His Ile
                    180                 185                 190

Ser Asp Ile Arg Tyr Asp His Leu Ser Ser Val Gln Pro Asn Gln Asn
                    195                 200                 205

Glu Tyr Ser Arg Ile Thr Val Arg Ile Asp Ala Val Arg Gln Met Gly
                    210                 215                 220

Tyr Tyr Leu Ile Gln Met Tyr Ile Pro Ser Leu Leu Ile Val Ile Leu
225                 230                 235                 240

Ser Trp Ile Ser Phe Trp Ile Asn Met Asp Ala Ala Pro Ala Arg Val
                    245                 250                 255

Gly Leu Gly Ile Thr Thr Val Leu Thr Met Thr Thr Gln Ser Ser Gly
                    260                 265                 270

Ser Arg Ala Ser Leu Pro Lys Val Ser Tyr Val Lys Ala Ile Asp Ile
                    275                 280                 285

Trp Met Ala Val Cys Leu Leu Phe Val Phe Ser Ala Leu Leu Glu Tyr
                    290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
                    325                 330                 335

Asn Met Phe Tyr Trp Ile Arg Gly Ile Thr Leu
                    340                 345

<210> SEQ ID NO 16
<211> LENGTH: 76
<212> TYPE: PRT
<213> ORGANISM: Homo sapiens

<400> SEQUENCE: 16

Gln His Lys Glu Leu Leu Arg Phe Arg Arg Lys Arg Arg His His Lys
1               5                   10                  15

Glu Asp Glu Ala Gly Glu Gly Arg Phe Asn Phe Ser Ala Tyr Gly Met
                20                  25                  30

Gly Pro Ala Cys Leu Gln Ala Lys Asp Gly Ile Ser Val Lys Gly Ala
            35                  40                  45

Asn Asn Ser Asn Thr Thr Asn Pro Pro Pro Ala Pro Ser Lys Ser Pro
        50                  55                  60

Glu Glu Met Arg Lys Leu Phe Ile Gln Arg Ala Lys
65                  70                  75

<210> SEQ ID NO 17
<211> LENGTH: 7
<212> TYPE: PRT
<213> ORGANISM: Gloeobacter violaceus
```

```
<400> SEQUENCE: 17

Ser Gln Pro Ala Arg Ala Ala
1               5

<210> SEQ ID NO 18
<211> LENGTH: 11
<212> TYPE: PRT
<213> ORGANISM: Homo sapiens

<400> SEQUENCE: 18

Lys Ile Val Arg Arg Glu Asp Val His Asn Gln
1               5                   10

<210> SEQ ID NO 19
<211> LENGTH: 13
<212> TYPE: PRT
<213> ORGANISM: Homo sapiens

<400> SEQUENCE: 19

Ile Tyr Lys Ile Val Arg Arg Glu Asp Val His Asn Gln
1               5                   10

<210> SEQ ID NO 20
<211> LENGTH: 5
<212> TYPE: PRT
<213> ORGANISM: Artificial Sequence
<220> FEATURE:
<223> OTHER INFORMATION: C terminal sequence

<400> SEQUENCE: 20

Arg Gly Ile Thr Leu
1               5

<210> SEQ ID NO 21
<211> LENGTH: 4
<212> TYPE: PRT
<213> ORGANISM: Gloeobacter violaceus

<400> SEQUENCE: 21

Arg Ile Ser Arg
1

<210> SEQ ID NO 22
<211> LENGTH: 4
<212> TYPE: PRT
<213> ORGANISM: Homo sapiens

<400> SEQUENCE: 22

Gln Met Gly Tyr
1

<210> SEQ ID NO 23
<211> LENGTH: 4
<212> TYPE: PRT
<213> ORGANISM: Erwinia chrysanthemi

<400> SEQUENCE: 23

Val Arg Ile Asp
1

<210> SEQ ID NO 24
<211> LENGTH: 4
<212> TYPE: PRT
<213> ORGANISM: Homo sapiens
```

```
<400> SEQUENCE: 24

Tyr Leu Ile Gln
1

<210> SEQ ID NO 25
<211> LENGTH: 7
<212> TYPE: PRT
<213> ORGANISM: Homo sapiens

<400> SEQUENCE: 25

Thr Gln Ser Ser Gly Ser Arg
1               5

<210> SEQ ID NO 26
<211> LENGTH: 88
<212> TYPE: PRT
<213> ORGANISM: Homo sapiens

<400> SEQUENCE: 26

Tyr Tyr Leu Ile Gln Met Tyr Ile Pro Ser Leu Leu Ile Val Ile Leu
1               5                   10                  15

Ser Trp Ile Ser Phe Trp Ile Asn Met Asp Ala Ala Pro Ala Arg Val
            20                  25                  30

Gly Leu Gly Ile Thr Thr Val Leu Thr Met Thr Thr Gln Ser Ser Gly
        35                  40                  45

Ser Arg Ala Ser Leu Pro Lys Val Ser Tyr Val Lys Ala Ile Asp Ile
    50                  55                  60

Trp Met Ala Val Cys Leu Leu Phe Val Phe Ser Ala Leu Leu Glu Tyr
65                  70                  75                  80

Ala Ala Val Asn Phe Val Ser Arg
                85

<210> SEQ ID NO 27
<211> LENGTH: 36
<212> TYPE: PRT
<213> ORGANISM: Homo sapiens

<400> SEQUENCE: 27

Lys Ile Asp Lys Ile Ser Arg Ile Gly Phe Pro Met Ala Phe Leu Ile
1               5                   10                  15

Phe Asn Met Phe Tyr Trp Ile Ile Tyr Lys Ile Val Arg Arg Glu Asp
            20                  25                  30

Val His Asn Gln
        35

<210> SEQ ID NO 28
<211> LENGTH: 192
<212> TYPE: PRT
<213> ORGANISM: Gloeobacter violaceus

<400> SEQUENCE: 28

Gly Gln Asp Met Val Ser Pro Pro Pro Ile Ala Asp Glu Pro Leu
1               5                   10                  15

Thr Val Asn Thr Gly Ile Tyr Leu Ile Glu Cys Tyr Ser Leu Asp Asp
            20                  25                  30

Lys Ala Glu Thr Phe Lys Val Asn Ala Phe Leu Ser Leu Ser Trp Lys
        35                  40                  45

Asp Arg Arg Leu Ala Phe Asp Pro Val Arg Ser Gly Val Arg Val Lys
    50                  55                  60
```

-continued

```
Thr Tyr Glu Pro Glu Ala Ile Trp Ile Pro Glu Ile Arg Phe Val Asn
 65                  70                  75                  80

Val Glu Asn Ala Arg Asp Ala Asp Val Val Asp Ile Ser Val Ser Pro
                 85                  90                  95

Asp Gly Thr Val Gln Tyr Leu Glu Arg Phe Ser Ala Arg Val Leu Ser
            100                 105                 110

Pro Leu Asp Phe Arg Arg Tyr Pro Phe Asp Ser Gln Thr Leu His Ile
        115                 120                 125

Tyr Leu Ile Val Arg Ser Val Asp Thr Arg Asn Ile Val Leu Ala Val
    130                 135                 140

Asp Leu Glu Lys Val Gly Lys Asn Asp Asp Val Phe Leu Thr Gly Trp
145                 150                 155                 160

Asp Ile Glu Ser Phe Thr Ala Val Val Lys Pro Ala Asn Phe Ala Leu
                165                 170                 175

Glu Asp Arg Leu Glu Ser Lys Leu Asp Tyr Gln Leu Arg Ile Ser Arg
            180                 185                 190

<210> SEQ ID NO 29
<211> LENGTH: 199
<212> TYPE: PRT
<213> ORGANISM: Erwinia chrysanthemi

<400> SEQUENCE: 29

Ala Pro Ala Asp Asn Ala Ala Asp Ala Arg Pro Val Asp Val Ser Val
  1               5                  10                  15

Ser Ile Phe Ile Asn Lys Ile Tyr Gly Val Asn Thr Leu Glu Gln Thr
                 20                  25                  30

Tyr Lys Val Asp Gly Tyr Ile Val Ala Gln Trp Thr Gly Lys Pro Arg
             35                  40                  45

Lys Thr Pro Gly Asp Lys Pro Leu Ile Val Glu Asn Thr Gln Ile Glu
 50                  55                  60

Arg Trp Ile Asn Asn Gly Leu Trp Val Pro Ala Leu Glu Phe Ile Asn
 65                  70                  75                  80

Val Val Gly Ser Pro Asp Thr Gly Asn Lys Arg Leu Met Leu Phe Pro
                 85                  90                  95

Asp Gly Arg Val Ile Tyr Asn Ala Arg Phe Leu Gly Ser Phe Ser Asn
            100                 105                 110

Asp Met Asp Phe Arg Leu Phe Pro Phe Asp Arg Gln Gln Phe Val Leu
        115                 120                 125

Glu Leu Glu Pro Phe Ser Tyr Asn Asn Gln Gln Leu Arg Phe Ser Asp
    130                 135                 140

Ile Gln Val Tyr Thr Glu Asn Ile Asp Asn Glu Glu Ile Asp Glu Trp
145                 150                 155                 160

Trp Ile Arg Gly Lys Ala Ser Thr His Ile Ser Asp Ile Arg Tyr Asp
                165                 170                 175

His Leu Ser Ser Val Gln Pro Asn Gln Asn Glu Phe Ser Arg Ile Thr
            180                 185                 190

Val Arg Ile Asp Ala Val Arg
    195

<210> SEQ ID NO 30
<211> LENGTH: 6
<212> TYPE: PRT
<213> ORGANISM: Gloeobacter violaceus

<400> SEQUENCE: 30
```

Leu Asp Asp Lys Ala Glu
1               5

<210> SEQ ID NO 31
<211> LENGTH: 6
<212> TYPE: PRT
<213> ORGANISM: Erwinia chrysanthemi

<400> SEQUENCE: 31

Val Asn Thr Leu Glu Gln
1               5

<210> SEQ ID NO 32
<211> LENGTH: 6
<212> TYPE: PRT
<213> ORGANISM: Homo sapiens

<400> SEQUENCE: 32

Ile Ala Glu Thr Thr Met
1               5

<210> SEQ ID NO 33
<211> LENGTH: 15
<212> TYPE: PRT
<213> ORGANISM: Gloeobacter violaceus

<400> SEQUENCE: 33

Ser Pro Leu Asp Phe Arg Arg Tyr Pro Phe Asp Ser Gln Thr Leu
1               5                   10                  15

<210> SEQ ID NO 34
<211> LENGTH: 15
<212> TYPE: PRT
<213> ORGANISM: Erwinia chrysanthemi

<400> SEQUENCE: 34

Asn Asp Met Asp Phe Arg Leu Phe Pro Phe Asp Arg Gln Gln Phe
1               5                   10                  15

<210> SEQ ID NO 35
<211> LENGTH: 15
<212> TYPE: PRT
<213> ORGANISM: Homo sapiens

<400> SEQUENCE: 35

Cys Pro Met Asp Leu Lys Asn Phe Pro Met Asp Val Gln Thr Cys
1               5                   10                  15

<210> SEQ ID NO 36
<211> LENGTH: 9
<212> TYPE: PRT
<213> ORGANISM: Gloeobacter violaceus

<400> SEQUENCE: 36

Gly Lys Asn Asp Asp Val Phe Leu Thr
1               5

<210> SEQ ID NO 37
<211> LENGTH: 11
<212> TYPE: PRT
<213> ORGANISM: Erwinia chrysanthemi

<400> SEQUENCE: 37

Asp Asn Glu Glu Ile Asp Glu Trp Trp Ile Arg
1               5                   10

```
<210> SEQ ID NO 38
<211> LENGTH: 11
<212> TYPE: PRT
<213> ORGANISM: Homo sapiens

<400> SEQUENCE: 38

Ala Val Gln Val Ala Asp Gly Leu Thr Leu Pro
1               5                   10

<210> SEQ ID NO 39
<211> LENGTH: 9
<212> TYPE: PRT
<213> ORGANISM: Gloeobacter violaceus

<400> SEQUENCE: 39

Gln Leu Arg Ile Ser Arg Gln Tyr Phe
1               5

<210> SEQ ID NO 40
<211> LENGTH: 9
<212> TYPE: PRT
<213> ORGANISM: Erwinia chrysanthemi

<400> SEQUENCE: 40

Arg Ile Asp Ala Val Arg Asn Pro Ser
1               5

<210> SEQ ID NO 41
<211> LENGTH: 9
<212> TYPE: PRT
<213> ORGANISM: Homo sapiens

<400> SEQUENCE: 41

Arg Phe His Leu Glu Arg Gln Met Gly
1               5

<210> SEQ ID NO 42
<211> LENGTH: 8
<212> TYPE: PRT
<213> ORGANISM: Gloeobacter violaceus

<400> SEQUENCE: 42

Leu Pro Lys Thr Pro Tyr Met Thr
1               5

<210> SEQ ID NO 43
<211> LENGTH: 8
<212> TYPE: PRT
<213> ORGANISM: Erwinia chrysanthemi

<400> SEQUENCE: 43

Leu Pro Arg Leu Pro Tyr Thr Thr
1               5

<210> SEQ ID NO 44
<211> LENGTH: 8
<212> TYPE: PRT
<213> ORGANISM: Homo sapiens

<400> SEQUENCE: 44

Leu Pro Lys Val Ser Tyr Val Lys
1               5
```

```
<210> SEQ ID NO 45
<211> LENGTH: 5
<212> TYPE: PRT
<213> ORGANISM: Gloeobacter violaceus

<400> SEQUENCE: 45

Ile Tyr Phe Gly Phe
1               5

<210> SEQ ID NO 46
<211> LENGTH: 5
<212> TYPE: PRT
<213> ORGANISM: Erwinia chrysanthemi

<400> SEQUENCE: 46

Arg Gly Ile Thr Leu
1               5

<210> SEQ ID NO 47
<211> LENGTH: 13
<212> TYPE: PRT
<213> ORGANISM: Homo sapiens

<400> SEQUENCE: 47

Ile Tyr Lys Ile Val Arg Arg Glu Asp Val His Asn Gln
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Linker

<400> SEQUENCE: 48

His His Arg Gln Ala Asn Gly Val Glu Asp Asp
1               5                   10

<210> SEQ ID NO 49
<211> LENGTH: 5
<212> TYPE: PRT
<213> ORGANISM: Erwinia chrysanthemi

<400> SEQUENCE: 49

Gly Gly Gly Gly Gly
1               5

<210> SEQ ID NO 50
<211> LENGTH: 20
<212> TYPE: PRT
<213> ORGANISM: Homo sapiens

<400> SEQUENCE: 50

Arg Val Gly Leu Gly Ile Thr Thr Val Leu Thr Met Thr Thr Gln Ser
1               5                   10                  15

Ser Gly Ser Arg
            20

<210> SEQ ID NO 51
<211> LENGTH: 20
<212> TYPE: PRT
<213> ORGANISM: Homo sapiens

<400> SEQUENCE: 51

Pro Ala Arg Val Gly Leu Gly Ile Thr Thr Val Leu Thr Met Thr Thr
```

1               5                   10                  15

Gln Ser Ser Gly
            20

<210> SEQ ID NO 52
<211> LENGTH: 347
<212> TYPE: PRT
<213> ORGANISM: Artificial Sequence
<220> FEATURE:
<223> OTHER INFORMATION: Engineered Chloride Channel Receptor
<220> FEATURE:
<221> NAME/KEY: misc_feature
<222> LOCATION: (60)..(60)
<223> OTHER INFORMATION: Xaa can be W or Y
<220> FEATURE:
<221> NAME/KEY: misc_feature
<222> LOCATION: (101)..(101)
<223> OTHER INFORMATION: Xaa can be W or Y
<220> FEATURE:
<221> NAME/KEY: misc_feature
<222> LOCATION: (113)..(113)
<223> OTHER INFORMATION: Xaa can be D, E, S, T, N, Q, C, U, G, P, A, V,
      I, L, M, F, Y, W, H
<220> FEATURE:
<221> NAME/KEY: misc_feature
<222> LOCATION: (155)..(155)
<223> OTHER INFORMATION: Xaa can be W or Y
<220> FEATURE:
<221> NAME/KEY: misc_feature
<222> LOCATION: (210)..(210)
<223> OTHER INFORMATION: Xaa can be W or Y
<220> FEATURE:
<221> NAME/KEY: misc_feature
<222> LOCATION: (268)..(268)
<223> OTHER INFORMATION: Xaa can be N, Q, S, T, Y, D, E, R, H, K
<220> FEATURE:
<221> NAME/KEY: misc_feature
<222> LOCATION: (271)..(271)
<223> OTHER INFORMATION: Xaa can be any naturally occurring amino acid

<400> SEQUENCE: 52

Met Gly Leu Arg Ala Leu Met Leu Trp Leu Leu Ala Ala Ala Gly Leu
1               5                   10                  15

Val Arg Glu Ser Leu Gln Ala Pro Ala Asp Asn Ala Ala Asp Ala Arg
            20                  25                  30

Pro Val Asp Val Ser Val Ser Ile Phe Ile Asn Lys Ile Tyr Gly Val
        35                  40                  45

Asn Thr Leu Glu Gln Thr Tyr Lys Val Asp Gly Xaa Ile Val Ala Gln
    50                  55                  60

Trp Thr Gly Lys Pro Arg Lys Thr Pro Gly Asp Lys Pro Leu Ile Val
65                  70                  75                  80

Glu Asn Thr Gln Ile Glu Arg Trp Ile Asn Asn Gly Leu Trp Val Pro
                85                  90                  95

Ala Leu Glu Phe Xaa Asn Val Val Gly Ser Pro Asp Thr Gly Asn Lys
            100                 105                 110

Xaa Leu Met Leu Phe Pro Asp Gly Arg Val Ile Tyr Asn Ala Arg Phe
        115                 120                 125

Leu Gly Ser Phe Ser Asn Asp Met Asp Phe Arg Leu Phe Pro Phe Asp
    130                 135                 140

Arg Gln Gln Phe Val Leu Glu Leu Glu Pro Xaa Ser Tyr Asn Asn Gln
145                 150                 155                 160

Gln Leu Arg Phe Ser Asp Ile Gln Val Tyr Thr Glu Asn Ile Asp Asn
                165                 170                 175

Glu Glu Ile Asp Glu Trp Trp Ile Arg Gly Lys Ala Ser Thr His Ile
            180                 185                 190

Ser Asp Ile Arg Tyr Asp His Leu Ser Ser Val Gln Pro Asn Gln Asn
            195                 200                 205

Glu Xaa Ser Arg Ile Thr Val Arg Ile Asp Ala Val Arg Gln Met Gly
    210                 215                 220

Tyr Tyr Leu Ile Gln Met Tyr Ile Pro Ser Leu Leu Val Ile Leu
225                 230                 235                 240

Ser Trp Ile Ser Phe Trp Ile Asn Met Asp Ala Ala Pro Ala Arg Val
            245                 250                 255

Gly Leu Gly Ile Thr Thr Val Leu Thr Met Thr Xaa Gln Ser Xaa Gly
            260                 265                 270

Ser Arg Ala Ser Leu Pro Lys Val Ser Tyr Val Lys Ala Ile Asp Ile
            275                 280                 285

Trp Met Ala Val Cys Leu Leu Phe Val Phe Ser Ala Leu Leu Glu Tyr
            290                 295                 300

Ala Ala Val Asn Phe Val Ser Arg Ser Gln Pro Ala Arg Ala Ala Lys
305                 310                 315                 320

Ile Asp Lys Ile Ser Arg Ile Gly Phe Pro Met Ala Phe Leu Ile Phe
            325                 330                 335

Asn Met Phe Tyr Trp Ile Arg Gly Ile Thr Leu
            340                 345

<210> SEQ ID NO 53
<211> LENGTH: 12
<212> TYPE: PRT
<213> ORGANISM: Artificial Sequence
<220> FEATURE:
<223> OTHER INFORMATION: Synthetic Homing Peptide

<400> SEQUENCE: 53

Asn Thr Gln Thr Leu Ala Lys Ala Pro Glu His Thr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Homing Peptide

<400> SEQUENCE: 54

His Leu Asn Ile Leu Ser Thr Leu Trp Lys Tyr Arg
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic Homing Peptide

<400> SEQUENCE: 55

Arg Pro Pro Gly Phe Ser Pro Phe
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Homing Peptide

<400> SEQUENCE: 56

```
Lys Pro Pro Gly Phe Ser Pro Phe
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Homing Peptide

<400> SEQUENCE: 57

Lys Arg Pro Pro Gly Phe Ser Pro Phe
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Homing Peptide

<400> SEQUENCE: 58

Lys Lys Pro Pro Gly Phe Ser Pro Phe
1               5

<210> SEQ ID NO 59
<211> LENGTH: 4
<212> TYPE: PRT
<213> ORGANISM: Erwinia chrysanthemi

<400> SEQUENCE: 59

Arg Asn Pro Ser
1

<210> SEQ ID NO 60
<211> LENGTH: 4
<212> TYPE: PRT
<213> ORGANISM: Homo sapiens

<400> SEQUENCE: 60

Arg Gln Met Gly
1

<210> SEQ ID NO 61
<211> LENGTH: 12
<212> TYPE: PRT
<213> ORGANISM: Erwinia chrysanthemi

<400> SEQUENCE: 61

Asn Gly Leu Trp Val Pro Ala Leu Glu Phe Ile Asn
1               5                   10

<210> SEQ ID NO 62
<211> LENGTH: 12
<212> TYPE: PRT
<213> ORGANISM: Gloeobacter violaceus

<400> SEQUENCE: 62

Glu Ala Ile Trp Ile Pro Glu Ile Arg Phe Val Asn
1               5                   10

<210> SEQ ID NO 63
<211> LENGTH: 5
<212> TYPE: PRT
<213> ORGANISM: Erwinia chrysanthemi
```

<400> SEQUENCE: 63

Phe Ser Tyr Asn Asn
1               5

<210> SEQ ID NO 64
<211> LENGTH: 5
<212> TYPE: PRT
<213> ORGANISM: Gloeobacter violaceus

<400> SEQUENCE: 64

Arg Ser Val Asp Thr
1               5

<210> SEQ ID NO 65
<211> LENGTH: 12
<212> TYPE: PRT
<213> ORGANISM: Erwinia chrysanthemi

<400> SEQUENCE: 65

Tyr Asp His Leu Ser Ser Val Gln Pro Asn Gln Asn
1               5                   10

<210> SEQ ID NO 66
<211> LENGTH: 8
<212> TYPE: PRT
<213> ORGANISM: Gloeobacter violaceus

<400> SEQUENCE: 66

Phe Ala Leu Glu Asp Arg Leu Glu
1               5

<210> SEQ ID NO 67
<211> LENGTH: 23
<212> TYPE: PRT
<213> ORGANISM: Homo sapiens

<400> SEQUENCE: 67

Tyr Leu Ile Gln Met Tyr Ile Pro Ser Leu Leu Ile Val Ile Leu Ser
1               5                   10                  15

Trp Ile Ser Phe Trp Ile Asn
            20

<210> SEQ ID NO 68
<211> LENGTH: 25
<212> TYPE: PRT
<213> ORGANISM: Homo sapiens

<400> SEQUENCE: 68

Ala Ile Asp Ile Trp Met Ala Val Cys Leu Leu Phe Val Phe Ser Ala
1               5                   10                  15

Leu Leu Glu Tyr Ala Ala Val Asn Phe
            20                  25

<210> SEQ ID NO 69
<211> LENGTH: 24
<212> TYPE: PRT
<213> ORGANISM: Homo sapiens

<400> SEQUENCE: 69

Lys Ile Ser Arg Ile Gly Phe Pro Met Ala Phe Leu Ile Phe Asn Met
1               5                   10                  15

Phe Tyr Trp Ile Ile Tyr Lys Ile

<210> SEQ ID NO 70
<211> LENGTH: 457
<212> TYPE: PRT
<213> ORGANISM: Homo sapiens

<400> SEQUENCE: 70

```
Met Tyr Ser Phe Asn Thr Leu Arg Leu Tyr Leu Trp Glu Thr Ile Val
1               5                   10                  15

Phe Phe Ser Leu Ala Ala Ser Lys Glu Ala Glu Ala Ala Arg Ser Ala
            20                  25                  30

Pro Lys Pro Met Ser Pro Ser Asp Phe Leu Asp Lys Leu Met Gly Arg
        35                  40                  45

Thr Ser Gly Tyr Asp Ala Arg Ile Arg Pro Asn Phe Lys Gly Pro Pro
    50                  55                  60

Val Asn Val Ser Cys Asn Ile Phe Ile Asn Ser Phe Gly Ser Ile Ala
65                  70                  75                  80

Glu Thr Thr Met Asp Tyr Arg Val Asn Ile Phe Leu Arg Gln Gln Trp
                85                  90                  95

Asn Asp Pro Arg Leu Ala Tyr Asn Glu Tyr Pro Asp Asp Ser Leu Asp
            100                 105                 110

Leu Asp Pro Ser Met Leu Asp Ser Ile Trp Lys Pro Asp Leu Phe Phe
        115                 120                 125

Ala Asn Glu Lys Gly Ala His Phe His Glu Ile Thr Thr Asp Asn Lys
    130                 135                 140

Leu Leu Arg Ile Ser Arg Asn Gly Asn Val Leu Tyr Ser Ile Arg Ile
145                 150                 155                 160

Thr Leu Thr Leu Ala Cys Pro Met Asp Leu Lys Asn Phe Pro Met Asp
                165                 170                 175

Val Gln Thr Cys Ile Met Gln Leu Glu Ser Phe Gly Tyr Thr Met Asn
            180                 185                 190

Asp Leu Ile Phe Glu Trp Gln Glu Gln Gly Ala Val Gln Val Ala Asp
        195                 200                 205

Gly Leu Thr Leu Pro Gln Phe Ile Leu Lys Glu Glu Lys Asp Leu Arg
    210                 215                 220

Tyr Cys Thr Lys His Tyr Asn Thr Gly Lys Phe Thr Cys Ile Glu Ala
225                 230                 235                 240

Arg Phe His Leu Glu Arg Gln Met Gly Tyr Tyr Leu Ile Gln Met Tyr
                245                 250                 255

Ile Pro Ser Leu Leu Ile Val Ile Leu Ser Trp Ile Ser Phe Trp Ile
            260                 265                 270

Asn Met Asp Ala Ala Pro Ala Arg Val Gly Leu Gly Ile Thr Thr Val
        275                 280                 285

Leu Thr Met Thr Thr Gln Ser Ser Gly Ser Arg Ala Ser Leu Pro Lys
    290                 295                 300

Val Ser Tyr Val Lys Ala Ile Asp Ile Trp Met Ala Val Cys Leu Leu
305                 310                 315                 320

Phe Val Phe Ser Ala Leu Leu Glu Tyr Ala Ala Val Asn Phe Val Ser
                325                 330                 335

Arg Gln His Lys Glu Leu Leu Arg Phe Arg Arg Lys Arg Arg His His
            340                 345                 350

Lys Ser Pro Met Leu Asn Leu Phe Gln Glu Asp Glu Ala Gly Glu Gly
        355                 360                 365
```

-continued

```
Arg Phe Asn Phe Ser Ala Tyr Gly Met Gly Pro Ala Cys Leu Gln Ala
    370             375             380

Lys Asp Gly Ile Ser Val Lys Gly Ala Asn Asn Ser Asn Thr Thr Asn
385             390             395             400

Pro Pro Pro Ala Pro Ser Lys Ser Pro Glu Glu Met Arg Lys Leu Phe
            405             410             415

Ile Gln Arg Ala Lys Lys Ile Asp Lys Ile Ser Arg Ile Gly Phe Pro
            420             425             430

Met Ala Phe Leu Ile Phe Asn Met Phe Tyr Trp Ile Ile Tyr Lys Ile
        435             440             445

Val Arg Arg Glu Asp Val His Asn Gln
    450             455
```

ENGINEERED RECEPTOR AND THEIR USE

CROSS REFERENCE TO RELATED APPLICATIONS

This is a continuation of U.S. patent application Ser. No. 14/650,859, filed on Jun. 9, 2015, which is the U.S. National Stage under § 371 of International Application No. PCT/US2013/073934, filed Dec. 9, 2013, which was published in English under PCT Article 21(2), which in turn claims the benefit of U.S. Provisional Application No. 61/735,503, filed Dec. 10, 2012. The prior applications are incorporated herein by reference in their entirety.

STATEMENT OF GOVERNMENT SUPPORT

This invention was made with government support under NIH R37GM049202 and R01GM056257 awarded by the National Institutes of Health. The government has certain rights in the invention.

FIELD

This disclosure relates to the field of engineered receptors, specifically to engineered receptors of use as therapeutics, such as for pain management and for the treatment of asthma or cystic fibrosis.

BACKGROUND

The treatment of pain conditions is of great importance in medicine. There is currently a worldwide need for additional pain therapy. "Pain" is defined by the International Association for the Study of Pain (IASP) as "an unpleasant sensory and emotional experience associated with actual or potential tissue damage, or described in terms of such damage" (IASP, Classification of chronic pain, 2.sup.nd Edition, IASP Press (2002), 210). Physiological and psychological factors affect the perception of pain. Some of the relevant pain subtypes are nociceptive pain, inflammatory pain, neuropathic pain, allodynia, hyperalgesia, and peripheral neuropathy.

Postsurgical pain (interchangeably termed, post-incisional pain), or pain that occurs after surgery or traumatic injury, is serious and often intractable. Pain is usually localized within the vicinity of the surgical site. Postsurgical pain can have two clinically important aspects, namely resting pain, or pain that occurs when the patient is not moving, and mechanical pain which is exacerbated by movement (coughing/sneezing, getting out of bed, physiotherapy, etc.). Drugs that are used to treat this pain often have a variety of side effects that delay recovery, prolong hospitalization and can have debilitating complications.

The major classes of pharmaceutical drugs used to treat various forms of pain are opioid analgesics, local anesthetics, non-steroidal anti-inflammatory drugs (NSAID), anti-depressants, and cannabinoids. Local anesthetics (e.g. channel blockers) are administered non-systemically during surgery while the other four classes of drugs, the opioid analgesics, NSAIDs, anti-depressants, and cannabinoids, are typically administered systemically. However, all the major classes of drugs for the treatment of pain are associated with risks of drug tolerance, dependence, or abuse. Analgesic tolerance often leads to hyperalgesia, requiring higher and higher doses of medication. Based on a 2011 report, prescription drugs for pain, or painkillers, kill twice as many people as cocaine and five times as many people as heroin (*Harvard Mental Health Letter*, 27:4-5, 2011). A need remains for other agents that can be used to treat pain.

SUMMARY

Chloride channel receptors are disclosed herein. In some embodiments, the chloride channel receptor includes a) a transmembrane domain of a glycine receptor in the absence of the extracellular and intracellular domains of the glycine receptor, wherein the transmembrane domain comprises domains TM1, TM2, TM3; and b) an extracellular domain of a pH-gated pentameric ligand-gated ion channel from *Gloeobacter violaceus* (GLIC) or an extracellular domain of an amine-activated pLGIC from *Erwinia chrysanthemi* (ELIC); and c) interfacial sequences between the extracellular domain and transmembrane domain, wherein the interfacial sequences comprise, in N-terminal to C-terminal order, loop 2, loop 7, loop 9, pre-TM1 linker, TM2-TM3 linker, and C-terminus, wherein loop 2, loop 7 loop 9, pre-TM1 linker, TM2-TM3 linker, and C-terminus are from *Gloeobacter violaceus, Erwinia chrysanthemi* or a human. The opening of the chloride channel receptor is induced by pH or by an activating molecule, such as, but not limited to, an amine.

In additional embodiments, a chloride channel receptor is provided, wherein the chloride channel receptor includes: a) a transmembrane domain of a glycine receptor in the absence of the extracellular and intracellular domains of the glycine receptor, wherein the transmembrane domain comprises domains TM1, TM2, TM3, and TM4; and b) the extracellular domain of a pH-gated pentameric ligand-gated ion channel (pLGIC) from *Gloeobacter violaceus* or the extracellular domain of an amine-activated pLGIC from *Erwinia chrysanthemi* (ELIC), wherein the receptor includes, in N terminal to C terminal order, loop 2, loop 5, loop 7, loop 8, loop 9, loop 10, pre-TM1 linker, TM1, TM2, TM2-TM3 linker, TM3, and TM4, and wherein opening of the chloride channel receptor is induced by pH or by an activating molecule.

In yet other embodiments, the chloride channel receptors can include activating mutations and/or a signal sequence.

In further embodiments, nucleic acids are disclosed encoding these chloride channel receptors; vectors including these nucleic acids are also provided. In yet other embodiments, disclosed are nanoparticles and pharmaceutical compositions including these engineered chloride channels, nucleic acids and/or vectors.

In some embodiments, the use of these chloride channel receptors, nucleic acids, vectors, pharmaceutical compositions and/or nanoparticles is disclosed. Suitable uses include, but are not limited to, the treatment of pain, asthma, and cystic fibrosis. In some methods, a therapeutically effective amount of the chloride channel receptors, nucleic acids, vectors, pharmaceutical compositions and/or nanoparticle is administered to a subject of interest, such as a subject with pain, asthma or cystic fibrosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C. Exemplary receptor engineering. Schematic diagrams representing the amino acid sequences of the engineered receptors, N-terminal to C-terminal, left to right. Two classes of Cl⁻ channels were designed, comprising a bacterial extracellular domain from either GLIC or ELIC controlling how the channel is activated, colored dark grey; a human glycine receptor transmembrane domain controlling Cl⁻ selectivity, colored light grey; and an artificial linker of any peptide lengths between TM3 and TM4, colored black. The transmembrane domain consists of four transmembrane helices marked with large boxes as TM1, TM2, TM3, and TM4. The sequences that interface between the extracellular and transmembrane domains in the three-dimensional space are indicated as small boxes identified with labels above the boxes. FIG. 1A. In this design, the domains are joined but the interfacial regions are not changed. FIG. 1B. In this design, the interface regions in the human glycine receptor transmembrane domain have been mutated to match those from the homologous region of the bacterial proteins. FIG. 1C. In this design, the interface regions in the bacterial extracellular domain have been mutated to match those from the homologous region of the human glycine receptor. Mutation strategies in the extracellular domain disclosed herein control the affinity and matching between the engineered channels and the activating molecules. Mutation strategies in the pore-lining TM2 domain disclosed herein allows fine-tuning of channel responses to different degrees of inflammatory pain.

FIG. 2. Ion selectivity of the engineered channels. Shown are I-V dependence measurements in the presence of Na gluconate, NaCl, and choline chloride. The 50 mV positive shift in the reversal potential upon replacement of chloride with gluconate indicates a Cl⁻ channel. The permeability is ~10 times greater for Cl⁻ than for Na⁺.

(FIG. 3A) Class I: Cl⁻ currents through four different engineered GLIC-GlyR channels were activated by changing the extracellular pH, mimicking varying degrees of inflammatory condition. The data were fit to the Hill equation with an $EC_{50}$ of 7.34±0.02, 7.04±0.03, 6.72±0.07, and 6.10±0.04 for the four designs S16' (●), S16'V (□), S16'V (▲), and S16'I (■), respectively. Hill slopes were ~2. (FIG. 3B) Class II: Cl⁻ currents through an EG channel were activated by a small amine in a concentration-dependent manner. The data were fit to the Hill equation with an $EC_{50}$ of 0.96±0.12 and a Hill slope of 1.1±0.1. All data points are displayed as mean±SEM from n≥3 oocytes. Some error bars are smaller than the symbol size.

FIGS. 5A-5D. rAAV8 transgene expression in the peripheral nerve. Transgene expression in the sensory and motor fibers (dorsal and ventral spinal roots, respectively) around L4 and L5 dorsal root ganglia was measured by the reporter protein ZsGreen after intrathecal rAAV8 injection. Only sensory nerve (dorsal spinal root) expressed ZsGreen fluorescence. FIGS. 5A and 5C are bright field images, and 5B and 5D are fluorescence images. Stars indicate motor fibers and triangles indicate sensory fibers.

(FIG. 6A) By reducing electrostatic repulsion, R91A mutation increased the affinity of primary amines at the agonist-binding site. Docking study suggested that adding F188Y mutation to increase the cation-π interaction can further increase the potency of an amine to open the Cl⁻ channels. (FIG. 6B) Dose-dependence measurements in oocytes showed nearly 3 orders of magnitude increase in propylamine potency in the $EG_{RAFY}$ mutant (red, $EC_{50}$=0.0019±0.0002 mM, Hill coeff.=0.98±0.07, n=6) as compared to the EG channel (black, EC50=0.74±0.11 mM, Hill coeff.=0.5±0.04, n=6).

FIGS. 8A-8D. Engineered ELIC-GLYR (EG) Cl⁻ channels for pain control. (FIG. 8A) A schematic representation of nociceptive and inflammatory pain. Terminals of sensory neurons, particularly those of the unmyelinated C-fibers and thinly myelinated Aδ-fibers, detect pain-evoking conditions in the periphery and initiate the propagation of depolarizing action potentials along the nerve fibers to the dorsal horn of the spinal cord, where the pain signal is projected to the brain as pain perception. (FIG. 8B) Amino acid sequence (SEQ ID NO: 12) of one of the designed ELIC-GLYR (EG) Cl⁻ channels to serve as peripheral antihyperalgesic responders. The ELIC ligand-binding domain and the GlyR transmembrane domain are underlined in green and blue, respectively. The engineered interfacial residuals to improve communications between the two domains are highlighted (Pre-TM1; TM23 loop; and C-terminal). (FIG. 8C) High-resolution structural model derived from crystal structure of ELIC (top (light grey), pdb code: 3RQW) and NMR structure of GlyR TM domain (bottom (dark grey), pdb: 2M6I). The agonist cysteamine is depicted. (FIG. 8D) Dose responses of EG channel current in *Xenopus* oocytes as a function of cysteamine concentrations. The data were fit to the Hill equation with an $EC_{50}$ of 0.96±0.12 mM and a Hill slope of 1.1±0.1. (e) Ion selectivity of the EG channel. Asymmetric IV curves were measured with 130 mM NaCl (Δ), choline chloride (■), or sodium gluconate (●) in the external solution. A 50-mV shift in reversal potential upon replacing Cl⁻ with gluconate and no significant shift upon replacing Na⁺ with choline indicate a Cl⁻ selective channel with negligible Na⁺ contribution to the current. All data points are displayed as mean±SD (n=6). Some error bars are smaller than the symbol size.

(FIG. 10A) Timeline of behavioral tests. Sprague-Dawley rats received an injection (orange dot) of either designed EG-channel plasmid or control plasmid into the left hind paw after the baseline behavior test. One week after the plasmid injection, inflammation was induced by CFA injection (red dot) Behavioral tests for both mechanical withdrawal threshold and thermal withdrawal latency were performed on the post-inflammation days as indicated by light and dark violet dots. On each behavioral testing day, rats were tested twice: pre- (light violet dot) and post-cysteamine (dark violet dot) injection. Cysteamine (500 μl of 100 mM solution in PBS), injected subcutaneously elsewhere on the body, activated the designed channel and produced antihyperalgesia. (FIG. 10B) Alleviation of inflammation-induced mechanical allodynia. Mechanical pain threshold after CFA-induced inflammation is measured before (light open symbols) and after (dark filled symbols) cysteamine injection. In the animals with EG expression (dark and light blue, n=9), significant attenuation of allodynia occurred only after cysteamine injection (dark blue). EG alone (light blue) had no measurable effects on mechanical hypersensitivity as compared to the control group with empty-vector injection (green, n=11). Cysteamine produced no analgesia in the absence of EG (compare light and dark green groups). Asterisks indicate significant differences between post-cysteamine EG group and all other groups. (FIG. 10C) Attenuation of inflammation-induced thermal hyperalgesia. Latency to paw withdrawal is measured as a function of time after CFA injection. Color code is the same as in (FIG. 10B). Latencies showed significant attenuation of thermal hypersensitivity in rats with EG injection (n=4), when compared to the control (n=5). Asterisks indicate significant differences between post-cysteamine EG group and the control groups with and without cysteamine. *P<0.05, P<0.01, *P<0.001.

FIGS. 11A-11C. ELIC-GlyR chimeras (FIG. 11A) ELIC-GlyR sequence (SEQ ID NO: 12) with the tested interface elements indicated in gold. ELIC sequences and GlyR α1 (GLRA1) sequences are indicated (FIG. 11B) Sequence for the indicated interface elements of ELIC, GLRA1, and each of the chimeric constructs. ELIC sequences are in light grey; GLRA1 sequences are in dark grey. In FIG. 11B, the TM2-TM3 linker, LPRLPYTT is SEQ ID NO: 43, and LPKVSYVK is SEQ ID NO: 44, The C-terminus RGITL is SEQ ID NO: 46 and IYKIVRREDVHNQ is SEQ ID NO: 47, and the pre-TM1 sequences RNPS is SEQ ID NO: 59 and RQMG is SEQ ID NO: 60. Cysteamine responsiveness is reported as the measured $EC_{50}$ for cysteamine. (FIG. 11C) Cysteamine dose response curves for each of the chimeric constructs: ● EG, ○ EGd, ◇ EGc, ■, EGa, □ EGb. Data are fit to Hill equations with n≥3. Error bars are SD.

FIG. 12. Alignment. An alignment of Class I engineered chloride channel receptors (SEQ ID NOs: 1-7) is shown. These sequences include the following elements: loop 2 (residues 52-57); loop 7 (residues 134-148); loop 9 (residues 172-180); pre-TM1 (residues 215-218); TM1 (residues 219-241); TM2 (residues 246-267); TM3 (residues 278-302); TM3-4 linker (residues 306-312); TM4 (residues 316-337); and C-terminus (residues 338-340, except for SEQ NO ID: 4, which is 338-348). These sequences also include loop 5 (residues 91-102); loop 8 (residues 155-159); and loop 10 (residues 197-209).

Figure 13:
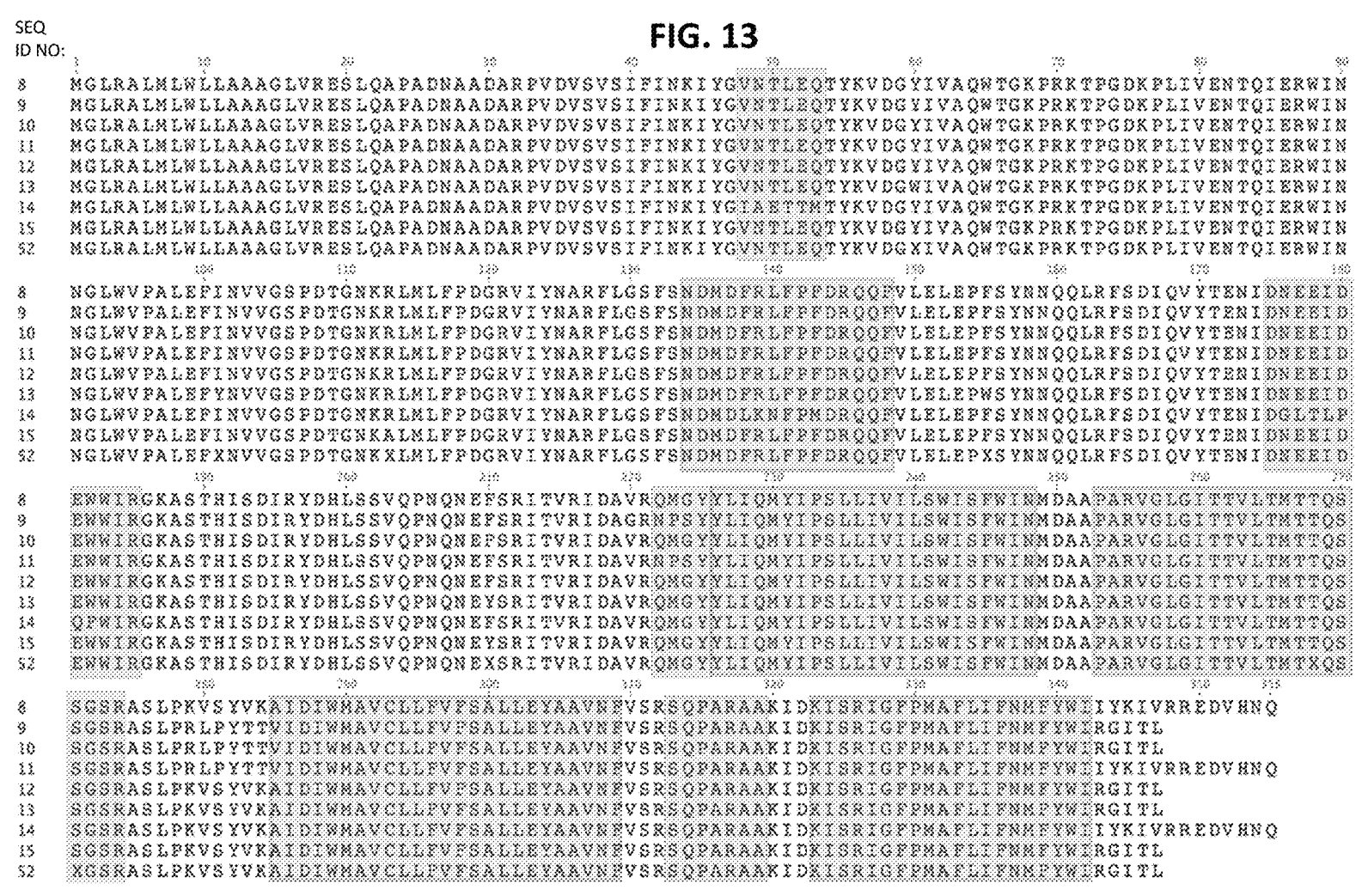

FIG. 13. Alignment. An alignment of Class II engineered chloride channel receptors (SEQ ID NOs: 8-15) is shown. These sequences include the following elements: loop 2 (residues 48-53); loop 7 (residues 134-148); loop 9 (residues 175-185); pre-TM1 (residues 222-225); TM1 (residues 226-248); TM2 (residues 253-274); TM3 (residues 285-309); TM3-4 linker (residues 313-319); TM4 (residues 323-342); and C-terminus (residues 343-347 for SEQ NO's ID: 9, 10, 12, 13, 15, 52, or residues 343-355 for SEQ NO's ID: 8, 11, 14). These sequences also include loop 5 (residues 91-102); loop 8 (residues 155-159); and loop 10 (residues 196-203).

SEQUENCE LISTING

Figure 3A:
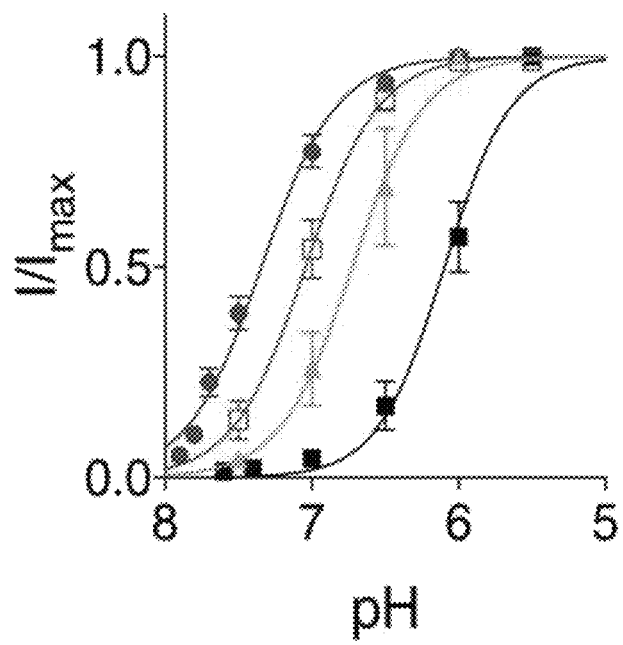
FIGS. 3A-3B. Engineered Cl⁻ channels for pain control.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file "8123-9031404_Sequence_Listing.txt", created on Mar. 9, 2017, and having a size of approximately 66.1 kilobytes which is incorporated by reference herein. In the accompanying sequence listing:

SEQ ID NOs: 1-7 are the amino acid sequences of exemplary pH gated (class I) engineered chloride channel receptors.

SEQ ID NOs: 8-15 are the amino acid sequence of exemplary small molecule gated (class II) engineered chloride channel receptors.

SEQ ID NO: 16 is an amino acid sequence of an intracellular loop of the human glycine receptor (GLRA1)

SEQ ID NO: 17 is an amino acid sequence of an intracellular loop from GLIC.

SEQ ID NOs: 18-19 are C-terminal amino acid sequences of GLRA1 which could be replaced in an engineered chloride channel receptor.

SEQ ID NO: 20 is an amino acid sequence that can replace the C-terminal sequences of an engineered chloride channel receptor.

SEQ ID NO: 21 is a portion of a C-terminal amino acid sequence of the extracellular domain of GLIC.

SEQ ID NO: 22 is an amino acid sequence of a portion of N-terminus of the glycine receptor transmembrane domain.

SEQ ID NO: 23 is an amino acid sequence of the C-terminal residues of an ELIC extracellular domain.

SEQ ID NO: 24 is an amino acid sequence of the N-terminal residues of a glycine receptor TMD.

SEQ ID NO: 25 is an amino acid sequence of a portion of TM2 of the human glycine receptor.

SEQ ID NO: 26 is an amino acid sequence of the transmembrane domains TM1, TM2, TM3 of the human glycine receptor.

SEQ ID NO: 27 is an amino acid sequence of the transmembrane domain TM4 and the C-terminus of the human glycine receptor.

SEQ ID NO: 28 is an amino acid sequence of the ECD of a pH-gated pentameric ion channel (GLIC)

SEQ ID NO: 29 is an amino acid sequence of the ECD of an amine-gated pentameric ion channel (ELIC).

SEQ ID NOs: 30-32 are loop 2 amino acid sequences from GLIC (SEQ ID NO: 30), ELIC (SEQ ID NO: 31), or GLRA1 (SEQ ID NO: 32).

SEQ ID NOs: 33-35 are loop 7 amino acid sequences from GLIC (SEQ ID NO: 33), ELIC (SEQ ID NO: 34), or GLRA1 (SEQ ID NO: 35).

SEQ ID NOs: 36-38 are loop 9 amino acid sequences from GLIC (SEQ ID NO: 36), ELIC (SEQ ID NO: 37), or GLRA1 (SEQ ID NO: 38).

SEQ ID NOs: 39-41 are pre-TM1 linker amino acid sequences from GLIC (SEQ ID NO: 39), ELIC (SEQ ID NO: 40), and GLRA1 (SEQ ID NO: 41).

SEQ ID NOs: 42-44 are TM2-TM3 linker amino acid sequences from GLIC (SEQ ID NO: 42), ELIC (SEQ ID NO: 43), and GLRA1 (SEQ ID NO 44).

SEQ ID NOs: 45-47 are C-terminal amino acid sequences from GLIC (SEQ ID NO: 45), (ELIC SEQ ID NO: 46), and GLRA1 (ELIC SEQ ID NO: 47).

SEQ ID NOs: 48-49 are linker amino acid sequences. SEQ ID NO: 48 is a synthetic sequence. SEQ ID NO: 49 is an amino acid sequence of a linker from ELIC.

SEQ ID NOs: 50-51 are TM2 amino acid sequences from GLRA1.

SEQ ID NO: 52 is an exemplary amino acid sequence of an amine gated chloride channel receptor SEQ ID NOs: 53-58 are the amino acid sequence of short peptides with selective homing properties that can be used in nanoparticles.

SEQ ID NOs: 59-60 are pre-TM1 amino acid sequences from ELIC (SEQ ID NO: 59), or GLRA1 (SEQ ID NO: 60).

SEQ ID NOs: 61-62 are loop 5 amino acid sequences from ELIC (SEQ ID NO: 61), or GLIC (SEQ ID NO: 62).

SEQ ID NOs: 63-64 are loop 8 amino acid sequences from ELIC (SEQ ID NO: 63), or GLIC (SEQ ID NO: 64). SEQ ID NO: 65-66 are loop 10 amino acid sequences from ELIC (SEQ ID NO: 65), or GLIC (SEQ ID NO: 66).

SEQ ID NO: 67 is the sequence of TM1 from GLRA1.

SEQ ID NO: 68 is the sequence of TM3 from GLRA1.

SEQ ID NO: 69 is the sequence of TM4 from GLRA1.

SEQ ID NO: 70 is the sequence of GLRA1.

DETAILED DESCRIPTION

Disclosed herein are proteins that form receptors or ion channels that are normally inactive and closed, and thus produce no measurable effect under normal physiological conditions. These receptors can respond to certain pathological conditions to provide therapeutic effects, and The expressed proteins are designed to either spontaneously respond to changes in physiological conditions, such as lowering of tissue pH during inflammation and tissue ischemia, or respond to agents that specifically bind to the designed proteins for activation (for example, to activate ion channels or to modulate the amount of currents passing through the ion channels).

In some embodiments, the receptors are pentameric chloride (anion) channels that are normally closed and can be opened by lowering pH. In non-limiting examples, the chloride channels are closed at normal physiological pH (pH=7.4), and spontaneously open by varying degrees in response to tissue acidosis (lowering of pH). The receptors can open, for example, at a pH of about 6.8 to about 7.2, such as at about 7.0. In some non-limiting examples, the pH $EC_{20}$ (20% of maximum currents) range from about pH 6.8 to about 5.5, such as about 6.5 to about 6.0.

In other embodiments, the chloride channels can be triggered to open, or be positively modulated, by either molecules that are not normally present in the physiological fluids. Thus, receptors and the ligands can be designed in pairs with desired binding affinity and specificity. When expressed in, or provided to, intended regions or organs, the receptors are silent until the ligand is administered, thereby achieving targeted therapy.

In additional embodiments, a chloride channel is provided that can be activated by an activating molecule, and thus can supplement inward chloride current to moderately hyperpolarize peripheral nerve cells. This chloride channel can be potentiated by a change in pH or application of an agent, such as, but not limited to, a primary or secondary amine. In other embodiments, the receptor can be activated by specific ligands or small molecules. In some non-limiting examples, the agent is an amine, such as cysteamine or propylamine.

In further embodiments, the engineered channel includes the *Erwinia chrysanthemi* ELIC agonist-binding domain and the transmembrane domain of the a1 glycine receptor. The engineered channels can include one or more mutation at the agonist binding site, including, but not limited to R91A, F188Y and F133Y numbered after the signal sequence of 22 amino acids in SEQ ID NO: 15. The positions of these residues are shaded in SEQ ID NO: 15 below.

In some embodiments, these receptors can be used in the treatment of inflammation and/or pain. Without being bound by theory, expression of any of the disclosed engineered receptors in the peripheral nerve endings, in the dorsal root ganglion, and/or in the dorsal horn of the spinal cord works to (a) hyperpolarize sensory nerves, (b) inhibit the propagation of depolarizing action potential by shunting the voltage-gated $Na^+$ channel currents, or (c) suppress excitatory neurotransmitter release as presynaptic inhibition by the primary afferent depolarization in the dorsal horn of the spinal cord, thereby elevating the pain threshold and alleviating both acute and chronic pain. In other embodiments, these receptors can be used (a) to treat cystic fibrosis by conditionally supplementing chloride channels and (b) to treat asthma through pH-dependent, inflammation-triggered bronchial dilation.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Activating Molecule: A molecule that can open a chloride channel, and thus can supplement inward chloride current to moderately hyperpolarize peripheral nerve cells when the channel is in these cells. Activating molecules include hydrogen ions or an amine, such as a primary or secondary amine, for example cysteamine or propylamine. Activating molecules also include ligands or small molecules. Additional exemplary activating molecules are disclosed below.

Adeno-associated Virus: Adeno-associated virus (AAV) is a small virus that infects humans and some other primate species. AAV is not currently known to cause disease and consequently the virus causes a very mild immune response. AAV can infect both dividing and non-dividing cells and may incorporate its genome into that of the host cell. The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. Rep is composed of four overlapping genes encoding Rep proteins required for the AAV life cycle, and Cap contains overlapping nucleotide sequences of capsid proteins: VP1, VP2 and VP3, which interact together to form a capsid of an icosahedral symmetry. For gene therapy, ITRs seem to be the only sequences required in cis next to the therapeutic gene: structural (cap) and packaging (rep) genes can be delivered in trans.

Animal: A living multicellular vertebrate organism, a category that includes, for example, mammals and birds. A "mammal" includes both human and non-human mammals. Similarly, the term "subject" includes both human and veterinary subjects.

Binding affinity: Affinity of a specific binding agent for its target, such as an antibody for an antigen, or a ligand for a target receptor. In one embodiment, affinity is calculated by a modification of the Scatchard method described by Frankel et al., *Mol. Immunol.*, 16:101-106, 1979. In another embodiment, binding affinity is measured by a specific binding agent receptor dissociation rate. In yet another embodiment, a high binding affinity is measured by a competition radioimmunoassay.

Central Nervous System (CNS): The part of the nervous system of an animal that contains a high concentration of cell bodies and synapses and is the main site of integration of nervous activity. In higher animals, the CNS generally refers to the brain and spinal cord.

Chloride Channel: Channels conduct Cl⁻ through a biological membrane. An engineered chloride channel is not naturally occurring. The pentameric ligand gated ion channel family of chloride channels contain 20 transmembrane helices, 4 from each subunit. Each protein of five subunits forms a single pore. A chloride channel receptor from this family of pentameric ligand gated ion channels is a chloride channel that must be specifically triggered by another biological molecule to open, such as by the binding of a ligand, or by pH.

Contacting: Placement in direct physical association, including both in solid or liquid form. Contacting can occur in vivo, for example by administering an agent to a subject, in vitro. "Administration" is the introduction of a composition, such as a composition containing an engineered receptor, into a subject by a chosen route. For example, if the chosen route is intravenous, the composition is administered by introducing the composition into a vein of the subject. "Administrating" to a subject includes intrathecal, perineural, topical, parenteral, oral, intravenous, intra-muscular, sub-cutaneous, inhalational, nasal, intravesical, or intra-articular administration, among others.

Covalent bond: An interatomic bond between two atoms, characterized by the sharing of one or more pairs of electrons by the atoms. The terms "covalently bound" or "covalently linked" refer to making two separate molecules into one contiguous molecule, for example a binding agent specific for a target receptor can be covalently linked (such as directly or indirectly through a linker) to an internalizing receptor-binding agent.

Figure 7A:
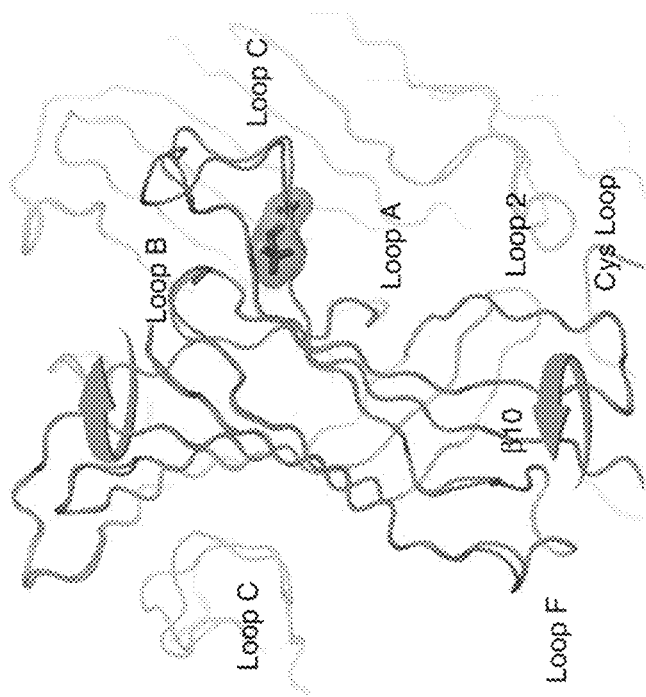
FIGS. 7A-7B. Schematic diagrams showing the positions of binding loops and other loops from the amino terminus to the carboxy terminus that adjoins the pre-M1 domain in Cys-loop receptors and the related acetylcholine binding proteins (labeling according to Brejc et al. Nature 411: 269-276, 2001). This is a side view of two adjacent subunits of ELIC crystal structure from FIG. 6 in Pan et al., *Nature Communications* doi:10.1038/ncomms1703 published online Mar. 6, 2012, incorporated herein by reference.
Figure 7B:
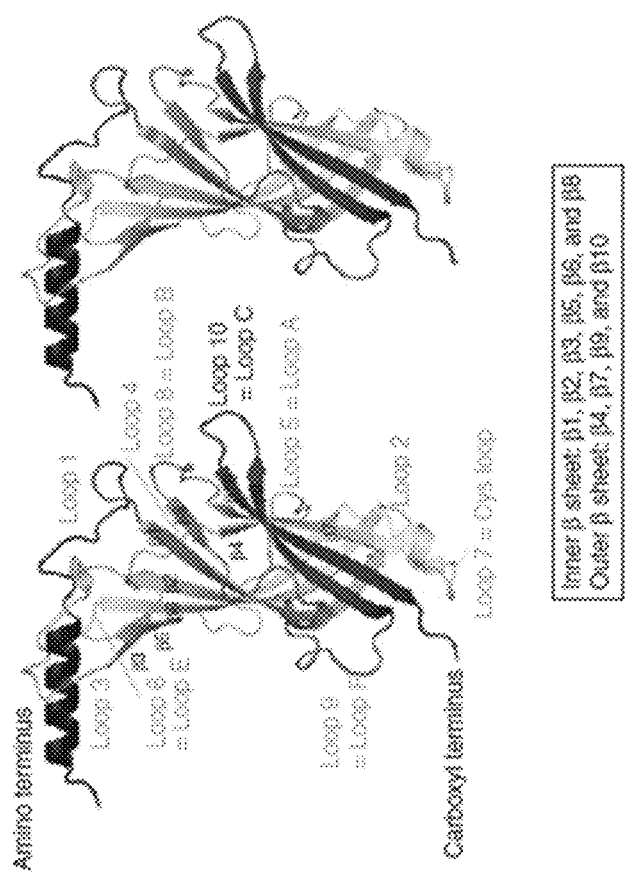
Figure 9A:
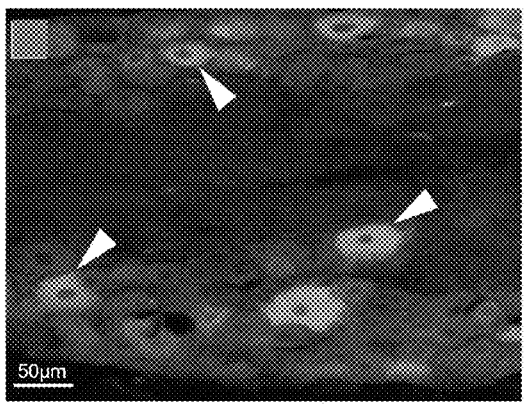
FIGS. 9A-9D. In vivo expression of the engineered ELIC-GLYR (EG) channels in the peripheral nerves. The amount of channel expression is assessed by the intensity of eGFP co-expressed with EG from the same expression vector two weeks after intradermal vector injection in the rat hind paws. The fluorescent intensity in the dorsal root ganglia (FIGS. 9A and 9B) and in the dermis and epidermal layer of the hind paw (FIGS. 9C and 9D) of the vector-injected animals (FIGS. 9A and 9C) is significantly higher than the autofluorescence in the vehicle-injected animals (FIGS. 9B and 9D), indicating a robust EG channel expression in both the cell bodies and terminals of peripheral nerves (arrowheads). Scale bars=100 μm.
Figure 9B:
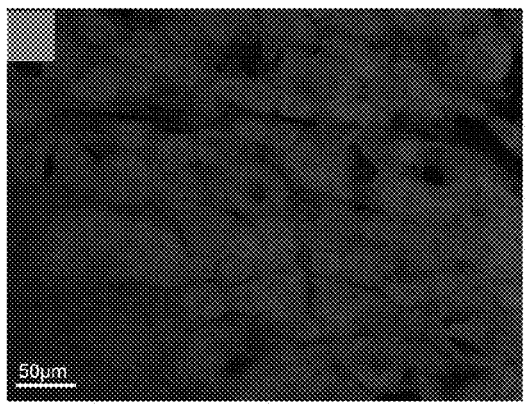
Figure 9C:
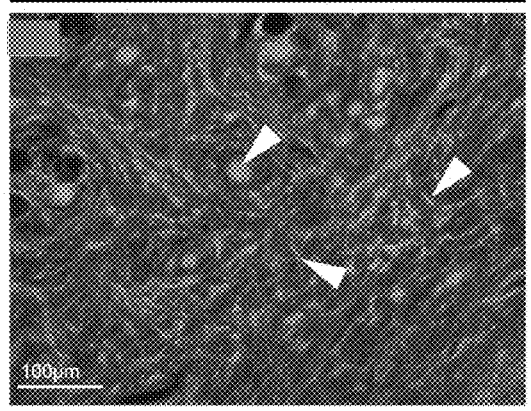
Figure 9D:
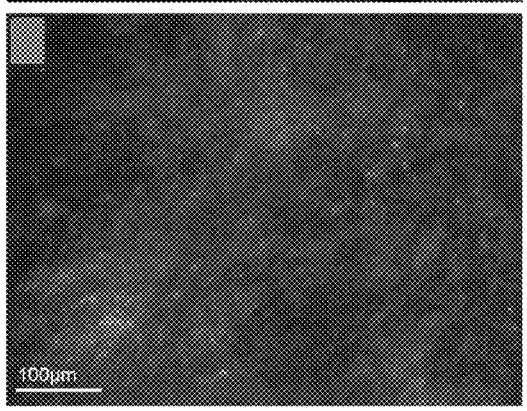

Cys-loop receptors: Receptors that generally contain a highly conserved structural feature of a loop formed by a disulfide bridge in the extracellular domain. These receptors include the nicotinic acetylcholine receptors, 5-hydroxytryptamine receptors (type 3), γ aminobutyric acid receptors (type A and C, $GABA_{A/C}R$), glycine receptors, the Zn activated cation channel, and invertebrate receptors activated by glutamate or serotonin or GABA. The wild-type pentameric ligand-gated ion channels (pLGIC) from *Gloeobacter violaceus* (GLIC) and from *Erwinia chrysanthemi* (ELIC) are bacterial homologues of Cys-loop receptors with structural similarity. The structure of these receptors is shown in FIG. 7. These receptors form pseudosymmetrical rings of five subunits, each contributing an extracellular domain (ECD) of anti-parallel sets of inner and outer β-sheets, a four-α-helical transmembrane domain (TMD), and an intracellular domain (ICD). Generally, in a wild-type receptor, the ECDs are positioned over the TMDs, providing a central aqueous pathway that stretches from the external vestibule formed by the ECDs, on through the TMDs and channel gate, before dissipating via the ICDs. The signature Cys-loop structure is formed by a disulfide bond and contains 13 amino acids situated at the base of the ECDs, see FIG. 7.

Without being bound by theory, several structures are believed to be important for transferring the conformational wave from the extracellular domain (ECD) to the transmembrane domain (TMD), specifically loop 2 (β1-β2, inner β-sheet), loop 7 (Cys loop, connects inner and outer β-sheets) and loop 9 (loop F) at the base of the ECD, together with the pre-M1 domain (linked to β10 and thus loop C) and the M2-M3 linker, see also Pan et al., Nature Comm. 3: 714, DOI: 10.1038/ncomms1703, 2012, incorporated herein by reference. Loops 2 and 7 arch over the M2-M3 linker. Loop 9 and the pre-M1 domain in the ECD may also interact with the TMD.

An "engineered receptor" is a receptor that is not naturally occurring, such as a chimeric receptor formed from two molecules, such as, but not limited to, a Cys-loop receptor and a glycine receptor.

Expression: Translation of a nucleic acid into a protein. Proteins may be expressed and remain intracellular, become a component of the cell surface membrane or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translate the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA and stop codons. The term "control sequences" is intended to include, at a minimum, components whose presence can influence expression and can also include additional components whose presence is advantageous, for example, leader sequences and fusion partner sequences. Expression control sequences can include a promoter.

A promoter is a minimal sequence sufficient to direct transcription. Also included are those promoter elements that are sufficient to render promoter-dependent gene expression controllable for cell-type specific, tissue-specific expression, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence, which facilitates the efficient transcription of the inserted genetic sequence of the host. The expression vector typically contains an origin of replication, a promoter, as well as specific nucleic acid sequences that allow phenotypic selection of the transformed cells.

Glycine receptor (GlyR): The receptor for the amino acid neurotransmitter glycine. GlyR is an ionotropic receptor that produces its effects through a chloride current. It is an inhibitory receptor that is found throughout the central nervous system. This receptor has important roles in a variety of physiological processes, such as for mediating inhibitory neurotransmission in the spinal cord and brain stem. GlyR can be activated by glycine, β-alanine and taurine, and can be selectively blocked by the high-affinity competitive antagonist strychnine. Caffeine is an antagonist of this receptor.

Heterologous: With reference to a molecule, such as a receptor or channel (for example chloride channel receptor) or a linker, "heterologous" refers to molecules that are not normally associated with this molecule, for example as a single molecule. Thus, a "heterologous" protein is a protein attached to another molecule that the protein is usually not found in association with in nature, such as in a wild-type molecule.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Inhibiting or treating a disease: Inhibiting the full development of a disease or condition, or decreasing intensity for example, in a subject who has cystic fibrosis, asthma, acute pain or chronic pain. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, reports of reduced intensity of pain, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. Similarly, an "isolated" protein can be been substantially separated, produced apart from, or purified away from other proteins of the organism in which the cell naturally occurs. Isolated proteins or nucleic acids can be, for example, at least 99%, at least 98%, at least 95%, at least 90%, at least 85%, or at least 80% pure.

Linker: A compound or moiety that acts as a molecular bridge to operably link two different molecules, wherein one portion of the linker is operably linked to a first molecule and wherein another portion of the linker is operably linked to a second molecule. In some examples a linker is a polypeptide. The two different molecules can be linked to the linker in a step-wise manner. There are no particular size or content limitations for the linker so long as it can fulfill its purpose as a molecular bridge. Linkers are known to those skilled in the art to include, but are not limited to, chemical chains, chemical compounds, carbohydrate chains, peptides, haptens and the like.

Nanoparticles: A molecular cluster of physical dimension from 1 to 10,000 nanometers. A nanometer is 1/1,000,000,000 of a meter. In non-limiting examples, nanoparticles can be spherical, cylindrical, or disc-shaped vesicles having one or multiple compartments enclosed or enveloped by molecules that are composed of a hydrophobic or water-avoiding moiety and a hydrophilic or water-liking moiety as in natural or synthetic lipids or polymers.

Neural Cell: A cell of the nervous system, specifically the peripheral or the central nervous system. A neural cell can be a nerve cell (neuron), for example a sensory neuron or a motoneuron, or a glial cell. Exemplary neurons include dorsal root ganglia of the spinal cord, spinal motor neurons, retinal bipolar cells, cortical and striatal cells of the brain, hippocampal pyramidal cells, and Purkinje cells of the cerebellum. Exemplary glial cells include oligodendrocytes and astrocytes of the central nervous system, and the Schwann cells of the peripheral nervous system.

Nociception: Neural process of encoding and processing a noxious stimulus.

Nucleic acid: A polymer composed of nucleotide units (ribonucleotides, deoxyribonucleotides, related naturally occurring structural variants and synthetic non-naturally occurring analogs thereof or combinations thereof) linked via phosphodiester bonds, related naturally occurring structural variants and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs) and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid, which can be used to transform a suitable host cell. A host cell that comprises the recombinant nucleic acid is referred to as a "recombinant host cell." The gene is then expressed in the recombinant host cell to produce, for example a "recombinant polypeptide." A recombinant nucleic acid may serve a non-coding function (for example a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA and TFASTA in the Wisconsin Genetics Software Package, Genetics Computer Group, 575 Science Dr., Madison, Wis.) or by manual alignment and visual inspection (see, for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10) and weighted end gaps. PILEUP can be obtained from the GCG sequence analysis software package, for example, version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (available on the internet, see ncbi.nlm.nih.gov). The BLASTN program (for nucleotide sequences) uses as defaults a word length (W) of 11, alignments (B) of 50, expectation (E) of 10, M=5, N=−4 and a comparison of both strands. The BLASTP program uses as defaults a word length (W) of 3 and expectation (E) of 10 and the BLOSUM62 scoring matrix (see Henikoff & Henikoff, *Proc. Natl. Acad. Sci. USA* 89:10915, 1989).

Nucleotide: The fundamental unit of nucleic acid molecules. A nucleotide includes a nitrogen-containing base attached to a pentose monosaccharide with one, two or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil and 2,6-diaminopurine 2'-deoxyguanosine amongst others.

Examples of modified sugar moieties, which may be used to modify nucleotides at any position on its structure, include, but are not limited to arabinose, 2-fluoroarabinose, xylose and hexose or a modified component of the phosphate backbone, such as phosphorothioate, a phosphorodithioate, a phosphoramidothioate, a phosphoramidate, a phosphordiamidate, a methylphosphonate or an alkyl phosphotriester or analog thereof.

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. In other examples, a molecule is "operably linked" to another molecule when the two molecules are connected by a linker, for example a linker connecting domain of a chloride channel receptor.

Pentameric ligand gated ion channels (pLGICs): A family of membrane proteins with a central role in biological signal transduction. These channels transmit an external signal—the binding of a ligand-through the opening of their ion-conducting pore. These channels play a role in nerve signaling; pLGICs are major pharmaceutical targets. At the structural level, <4-Å resolution X-ray chrystallography structures of two prokaryotic members of the family, ELIC and GLIC have been produced. The *Erwinia chrysanthemi* channel ELIC and the *Gloeobacter violaceus* channel GLIC are two homologous proteins with ~18% sequence identity. pLGICs are composed of five subunits that assemble into an extracellular domain (ECD) and a transmembrane domain (TMD) whose ion conductivity is gated by signals (typically ligand binding) from the ECD. Unlike most other pLGICs, GLIC is a pH-gated channel, a characteristic reflected in unique features of its ECD. The TMD of GLIC fully reflects the common features of the family (see Zhu and Hummer, Proc. Natl. Acad. Sci, 107: 19814-19819, 2010).

Pain: An unpleasant sensory and emotional experience associated with actual or potential tissue damage, or described in terms of such damage (IASP, Classification of chronic pain, second Edition, IASP Press (2002), 210). In particular examples of this disclosed methods the pain is medicated by nociceptors. Pain includes postsurgical pain, pain associates with tissue damage, pain from inflammation, pain from infection (shingles), pain from neuropathic conditions, and pain from skeletal muscular conditions.

Pharmaceutical agent: A chemical compound or composition capable of inducing a desired therapeutic or prophylactic effect when properly administered to a subject or a cell. In some embodiments, a pharmaceutical agent is receptor, such as a chloride channel receptor.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives and pH buffering agents and the like, for example sodium acetate or sorbitan monolaurate.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

A receptor peptide such as a target receptor peptide or a scavenger receptor peptide is a series of contiguous amino acid residues from a receptor peptide protein, such as a fragment of receptor peptide from about 10 to about 25 amino acids in length, such as about 11 to about 20 amino acid in length, such as about 12 consecutive amino acids of an receptor peptide protein. In some examples, an immunogenic composition for use in producing an antibody that specifically binds a receptor, such as a target receptor or an internalizing receptor, includes a receptor peptide.

Peripheral Nervous System (PNS): The part of an animal's nervous system other than the Central Nervous System. Generally, the PNS is located in the peripheral parts of the body and includes cranial nerves, spinal nerves and their branches, and the autonomic nervous system.

Pharmaceutical agent: A chemical compound, small molecule, or other composition capable of inducing a desired effect when properly administered to a subject or a cell. "Incubating" includes a sufficient amount of time for a drug to interact with a cell, such as a neuron. "Contacting" includes incubating a drug in solid or in liquid form with a cell, such as a neuron.

Polypeptide: Any chain of amino acids, regardless of length or post-translational modification (for example glycosylation or phosphorylation). In one embodiment, the polypeptide is receptor polypeptide. A "residue" refers to an amino acid or amino acid mimetic incorporated in a polypeptide by an amide bond or amide bond mimetic. A polypeptide has an amino terminal (N-terminal) end and a carboxy terminal end.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of polypeptide sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet (along with a description of how to determine sequence identity using this program).

Homologs and variants are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus, a receptor specific binding agent is an agent that binds substantially a specific receptor or fragment thereof. The term "specifically binds or specific binding" refers, with respect to a specific target, to the preferential association of a ligand, in whole or part, with a cell or tissue bearing that specific target and not to cells or tissues lacking a detectable amount of that specific target. It is recognized that a certain degree of non-specific interaction may occur between a molecule and a non-target cell or tissue. Specific binding may be distinguished as mediated through specific recognition of the specific receptor. Specific binding typically results in greater than 2-fold, such as greater than 5-fold, greater than 10-fold or greater than 100-fold increase in amount of bound antibody or other ligand (per unit time) to a cell or tissue bearing the specific target as compared to a cell or tissue lacking the specific target respectively.

Signal Sequence: A short (5-30 amino acids in length) peptide present at the N-terminus of newly synthesized proteins that are destined towards the secretory pathway, such as those that will be inserted into a membrane. At the end of the signal peptide there is typically a stretch of amino acids that is recognized and cleaved by signal peptidase. However this cleavage site is absent from transmembrane-domains that serve as signal peptides, which are sometimes referred to as signal anchor sequences. Signal peptidase can cleave a signal sequence from a protein either during or after completion of translocation to generate a free signal peptide and a mature protein. The free signal peptides are then digested by specific proteases.

Therapeutically effective amount: A quantity of a specific substance sufficient to achieve a desired effect in a subject being treated. For instance, this can be the amount necessary to reduce airway constriction in a subject with asthma, reduce symptoms of cystic fibrosis, reduce acute pain, reduce chronic pain, or treat inflammation. When administered to a subject, a dosage will generally be used that will achieve target tissue concentrations shown to achieve a desired in vitro effect.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors and introduction of DNA by electroporation, lipofection and particle gun acceleration.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: Microscopic infectious organism that reproduces inside living cells. A virus consists essentially of a core of a single nucleic acid surrounded by a protein coat and has the ability to replicate only inside a living cell. "Viral replication" is the production of additional virus by the occurrence of at least one viral life cycle. Viral vectors are known in the art, and include, for example, adenovirus, adeno-associated virus, lentivirus and herpes virus.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, a composition that includes "A or B" includes A, B or both A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Engineered Chloride Channel Receptors

Two classes of chloride ($Cl^-$) channel receptors have been designed and engineered that have the capability to counterbalance depolarization of peripheral nerves upon activation, thereby hyperpolarizing the nerve as needed to up-shift the pain threshold. These two classes of chloride channel receptors are triggered by different agents, namely small molecules or pH.

The glycine receptor (GlyR) transmembrane domain (TMD) alone, without the extracellular and intracellular domains, spontaneously forms $Cl^-$ conducting channels (*Structure,* 21:1897-904, 2013). Exemplary sequences for the GlyR are shown in GENBANK Accession Nos. NM_001146040.1 (NP_001139512.1), and NM_000171.3. (NP_000162.2), all incorporated by reference herein as available on Dec. 9, 2013. These two isoforms differ by an 8 residue deletion in the TM3-4 loop and a Q to K mutation immediately after, indicated in bold in the sequence shown below) The TMD of the GlyR α1 and α3 subunits harbors a novel cannabinoid-binding site that mediates marijuana's analgesic effects but not the psychoactive effects (*Nature Chemical Biology,* 7:296-303, 2011; *Journal of Experimental Medicine,* 209:1121-34, 2012). The human body has few or no glycine receptors in the peripheral nervous system. As disclosed herein, $Cl^-$ channel receptors have been designed using an engineered version of the GlyR TMD.

MYSFNTLRLYLWETIVFFSLAASKEAEAARSAP-
KPMSPSDFLDKLMGRTSGYDARI RPNFKGP-
PVNVSCNIFINSFGSIAETTMDYRVNIFL-
RQQWNDPRLAYNEYPDDSLD
LDPSMLDSIWKPDLFFANEKGAHF-

HEITTDNKLLRISRNGNVLYSIRITLTLACPMDL KNFPMDVQTCIMQLESFGYTMNDLIFEWQEQ-GAVQVADGLTLPQFILKEEKDLRY CTKHYNTG-KFTCIEARFHLERQMGYYLIQMYIPSLLIVILSW-ISFWINMDAAPARVG LGITTVLTMTTQSSGSR-ASLPKVSYVKAIDIWMAVCLLFVFSAL-LEYAAVNFVSRQH KELLRFRRKRRHHKSPMLN-LFQEDEAGEGRFNFSAYGMGPACLQAKDGIS-VKGA NNSNTTNPPPAPSKSPEEMRKLFIQR-AKKIDKISRIGFPMAFLIFNMFYWIIYKIVRR EDVHNQ (SEQ ID NO: 70)

The amino acid sequences of the engineered channel receptors, and nucleic acids encoding these engineered channel receptors, are not naturally occurring. The designing principles disclosed herein consist of several elements (see FIG. 1). An activator controls the opening of the engineered chloride channel receptor by pH or by a small nontoxic molecule. Thus, when the pH is lowered, or when a specific small molecule, such as an amine, is present the chloride channel opens, allowing a flux of chloride ions through the membrane of a cell.

In some embodiments, the channel is activated by an activating molecule such as a primary, secondary, tertiary or quaternary amine or a ligand. In particular embodiments, the activating molecules are primary amines such as cysteamine or propylamin. In other non-limiting examples, the activating molecules are N-3-pyridinyl-methanimidamide, 3-(2-aminoehtyl)pyridine, oxolan-3-yl carbamimidothioate, 2-(3, 4-dimethylcyclopent-3-en-1-yl)ethanamine, butyramidine, salicylamide, stavudine, chlorzoxazone, betazole, and pralidoxime. In yet other non-limiting examples, 2-(aminomethyl)phenol, 2-(aminomethyl)phenyl acetate, o-xylylamine, 1-[2-(aminomethyl)phenyl]ethanone, and o-anisylamine can be used as activating molecules. In other non-limiting examples, the activating amine is choline, or acetylcholine.

In further embodiments, the receptors are pentameric chloride (anion) channels that are normally closed and can be opened by lowering pH. In non-limiting examples, the chloride channels are closed at normal physiological pH (pH=7.4), and spontaneously open by varying degrees in response to tissue acidosis (lowering of pH). The receptors can open, for example, at a pH of about 6.8 to about 7.2, such as at about 7.0. In some non-limiting examples, the pH $EC_{20}$ (20% of maximum currents) range from about pH 6.8 to about 5.5, such as about 6.5 to about 6.0.

In these engineered chloride channel receptors, the interface can be optimized between (a) the TMD, which determines the Cl$^-$ ion selectivity, and (b) the extracellular domain (ECD), which controls the kinetics and efficacy of the activation (gating). The interface of ECD and TMD can be optimized using site-directed mutagenesis of the interface elements, which consist of amino acids that contact each other across the ECD and TMD. In some embodiments, the interface elements include loops 2, 7, 9, the pre-TM1 region, the TM2-3 linker and the C-terminus, as illustrated in FIG. 1. Loop 5, loop 8 and loop 10, are not interfacing loops.

In some embodiments, the interfacial sequences comprise loop 2 (LDDKAE (SEQ ID NO: 30), VNTLEQ (SEQ ID NO: 31), or IAETTM (SEQ ID NO: 32)), loop 7 (SPLD-FRRYPFDSQTL (SEQ ID NO: 33), NDMDFRLF-PFDRQQF (SEQ ID NO: 34), or CPMDLKNFPMDVQTC (SEQ ID NO: 35)), loop 9 (GKNDDVFLT (SEQ ID NO: 36), DNEEIDEWWIR (SEQ ID NO: 37) or AVQVADG-LTLP (SEQ ID NO: 38)), a pre-TM1 linker (QLRISRQYF (SEQ ID NO: 39), RIDAVRNPS (SEQ ID NO: 40), or RFHLERQMG (SEQ ID NO: 41)), TM2-TM3 linker (LPK-TPYMT (SEQ ID NO: 42), LPRLPYTT (SEQ ID NO: 43), or LPKVSYVK (SEQ ID NO: 44)), and C-terminus (IYFGF (SEQ ID NO: 45), RGITL (SEQ ID NO: 46), or IYKIVRREDVHNQ (SEQ ID NO: 47)). These sequences can be from the *Gloeobacter violaceus*, *Erwinia chrysanthemi*, or the human glycine receptors. In some embodiments, the ECD is from ELIC or GLIC. In further embodiments, the TMD is from a glycine receptor, such as the human glycine receptor.

In additional embodiments, the interface between the ECD of ELIC or GLIC and the TMD of the human glycine receptor, such as by using the crystal structures of ELIC and GLIC and the nuclear magnetic resonance structure available for the TMD of GlyR. In some embodiments, mutations are introduced in the interface between the ECD and the TMD, such as to produce maximum current, increase opening time, and/or alter the rate of desensitization. In specific non-limiting examples, one or more functions of the engineered chloride channels are tested using two electrode voltage clamp electrophysiology in *Xenopus* oocytes.

In further embodiments, the amount of pain control can be fine-tuned by allowing a different amount of Cl$^-$ current to pass through the engineered channels. Site-directed mutagenesis of the pore lining residues of the glycine receptor TMD modulates chloride conductance in response to activation. These effects of these mutations can be confirmed using electrophysiology to measure function. In some embodiments, a residue in the second TM domain of glycine receptor, S296 as defined by the human α1 sequence numbering (GENBANK NP_001139512.1, incorporated herein by reference as available on Dec. 9, 2013), is mutated to different amino acids to change the range of pH sensitivity. In yet other embodiments, modifications are made to increase half-life and remove antigenicity.

There are two types of engineered chloride channel receptors disclosed herein. These receptors can be pH gated (Class I) or gated by small molecules (Class II) such as amines. For pH-gated channels (Class I), the extracellular domain of a pH-gated pentameric ligand-gated ion channel (pLGIC) from *Gloeobacter violaceus* (GLIC) can be used as the activator. For small molecule-activated channels (Class II), the extracellular domain of an amine-activated pLGIC from *Erwinia chrysanthemi* (ELIC) was used. High-resolution crystal structures are available for GLIC (2.99 Å, pdb: 4F8H, GENBANK® Accession No. NP_927143.1 incorporated herein by reference, as available on Dec. 9, 2013) and ELIC (2.91 Å and 3.01 Å, pdb: 3RQW and 3RQU, GENBANK® Accession No.: YP_003884899.1, incorporated herein by reference as available on Dec. 9, 2013) and the high-resolution NMR structure for GlyR α1 TM domain (backbone RMSD 2.74 Å, pdb: 2M6B and 2M6I), the interface of the chimera channels that have the following sequences In the following sequences, the first 22 amino acids in gray lettering with dashed underlines indicates a mammalian signal sequence (which can be substituted for any other signal sequence, see amino acids 1-22 of each of SEQ ID NOs: 1-15 and 52); black lettering without underlining indicates sequences from either GLIC or ELIC; the underlined lettering indicates sequences from the human GlyR; and the bold shaded sequences or amino acids are sites where multiple mutations have been introduced:

Class I Engineered Channel Sequences

GG1
(SEQ ID NO: 1):
MGLRALMLWL LAAAGLVRES LQGQDMVSPP PPIADEPLTV NTGIYLIECY SLDDKAETFK

VNAFLSLSWK DRRLAFDPVR SGVRVKTYEP EAIWIPEIRF VNVENARDAD VVDISVSPDG

TVQYLERFSA RVLSPLDFRR YPFDSQTLHI YLIVRSVDTR NIVLAVDLEK VGKNDDVFLT

GWDIESFTAV VKPANFALED RLESKLDYQL RISRQMGYYL IQMYIPSLLI VILSWISFWI

NMDAAPARVG LGITTVLTMT TQSSGSRASL PKVSYVKAID IWMAVCLLFV FSALLEYAAV

NFVSRSQPAR AAKIDKISRI GFPMAFLIFN MFYWIIYFGF

GG2
(SEQ ID NO: 2):
MGLRALMLWL LAAAGLVRES LQGQDMVSPP PPIADEPLTV NTGIYLIECY SLDDKAETFK

VNAFLSLSWK DRRLAFDPVR SGVRVKTYEP EAIWIPEIRF VNVENARDAD VVDISVSPDG

TVQYLERFSA RVLSPLDFRR YPFDSQTLHI YLIVRSVDTR NIVLAVDLEK VGKNDDVFLT

GWDIESFTAV VKPANFALED RLESKLDYQL RISRQMGYYL IQMYIPSLLI VILSWISFWI

NMDAAPARVG LGITTVLTMT TQSIGSRASL PKVSYVKAID IWMAVCLLFV FSALLEYAAV

NFVSRSQPAR AAKIDKISRI GFPMAFLIFN MFYWIIYFGF

GG3
(SEQ ID NO: 3):
MGLRALMLWL LAAAGLVRES LQGQDMVSPP PPIADEPLTV NTGIYLIECY SLDDKAETFK

VNAFLSLSWK DRRLAFDPVR SGVRVKTYEP EAIWIPEIRF VNVENARDAD VVDISVSPDG

TVQYLERFSA RVLSPLDFRR YPFDSQTLHI YLIVRSVDTR NIVLAVDLEK VGKNDDVFLT

GWDIESFTAV VKPANFALED RLESKLDYQL RISRQMGYYL IQMYIPSLLI VILSWISFWI

NMDAAPARVG LGITTVLTMT TQSVGSRASL PKVSYVKAID IWMAVCLLFV FSALLEYAAV

NFVSRSQPAR AAKIDKISRI GFPMAFLIFN MFYWIIYFGF

GG4
(SEQ ID NO: 4):
MGLRALMLWL LAAAGLVRES LQGQDMVSPP PPIADEPLTV NTGIYLIECY SLDDKAETFK

VNAFLSLSWK DRRLAFDPVR SGVRVKTYEP EAIWIPEIRF VNVENARDAD VVDISVSPDG

TVQYLERFSA RVLSPLDFRR YPFDSQTLHI YLIVRSVDTR NIVLAVDLEK VGKNDDVFLT

GWDIESFTAV VKPANFALED RLESKLDYQL RISRQMGYYL IQMYIPSLLI VILSWISFWI

NMDAAPARVG LGITTVLTMT TQSAGSRASL PKVSYVKAID IWMAVCLLFV FSALLEYAAV

NFVSRSQPAR AAKIDKISRI GFPMAFLIFN MFYWIIYFGF

GG5
(SEQ ID NO: 5):
MGLRALMLWL LAAAGLVRES LQGQDMVSPP PPIADEPLTV NTGIYLIECY SIAETTMTFK

VNAFLSLSWK DRRLAFDPVR SGVRVKTYEP EAIWIPEIRF VNVENARDAD VVDISVSPDG

TVQYLERFSA RVLSPLDLKN FPMDSQTLHI YLIVRSVDTR NIVLAVDLEK VGKNDDVFLT

GWDIESFTDG LTLPQFALED RLESKLDYQL RISRQMGYYL IQMYIPSLLI VILSWISFWI

NMDAAPARVG LGITTVLTMT TQSVGSRASL PKVSYVKAID IWMAVCLLFV FSALLEYAAV

NFVSRSQPAR AAKIDKISRI GFPMAFLIFN MFYWIIYFGF

GG6
(SEQ ID NO: 6):
MGLRALMLWL LAAAGLVRES LQGQDMVSPP PPIADEPLTV NTGIYLIECY SIAETTMTFK

VNAFLSLSWK DRRLAFDPVR SGVRVKTYEP EAIWIPEIRF VNVENARDAD VVDISVSPDG

| Class I Engineered Channel Sequences |
| --- |
| TVQYLERFSA RVLSPLDLKN FPMDSQTLHI YLIVRSVDTR NIVLAVDLEK VGKNDDVFLT |
| GWDIESFTDG LTLPQFALED RLESKLDYQL RISRQMGYYL IQMYIPSLLI VILSWISFWI |
| NMDAAPARVG LGITTVLTMT TQSVGSRASL PKVSYVKAID IWMAVCLLFV FSALLEYAAV |
| NFVSRSQPAR AAKIDKISRI GFPMAFLIFN MFYWIIYKIV RREDVHNQ |

GG7
(SEQ ID NO: 7):
MGLRALMLWL LAAAGLVRES LQGQDMVSPP PPIADEPLTV NTGIYLIECY SLDDKAETFK
VNAFLSLSWK DRRLAFDPVR SGVRVKTYEP EAIWIPEIRF VNVENARDAD VVDISVSPDG
TVQYLERFSA RVLSPLDFRR YPFDSQTLHI YLIVRSVDTR NIVLAVDLEK VGKNDDVFLT
GWDIESFTAV VKPANFALED RLESKLDYQL RISRQMGYYL IQMYIPSLLI VILSWISFWI
NMDAAPARVG LGITTVLTMT TQSVGSRTNL PKTPYVKAID IWMAVCLLFV FSALLEYAAV
NFVSRSQPAR AAKIDKISRI GFPMAFLIFN MFYWIIYFGF

| Class II Engineered Channel Sequences |
| --- |

EG1
(SEQ ID NO: 8):
MGLRALMLWL LAAAGLVRES LQAPADNAAD ARPVDVSVSI FINKIYGVNT LEQTYKVDGY
IVAQWTGKPR KTPGDKPLIV ENTQIERWIN NGLWVPALEF INVVGSPDTG NKRLMLFPDG
RVIYNARFLG SFSNDMDFRL FPFDRQQFVL ELEPFSYNNQ QLRFSDIQVY TENIDNEEID
EWWIRGKAST HISDIRYDHL SSVQPNQNEF SRITVRIDAV RQMGYYLIQM YIPSLLIVIL
SWISFWINMD AAPARVGLGI TTVLTMTTQS SGSRASLPKV SYVKAIDIWM AVCLLFVFSA
LLEYAAVNFV SRSQPARAAK IDKISRIGFP MAFLIFNMFY WIIYKIVRRE DVHNQ

EG2
(SEQ ID NO: 9):
MGLRALMLWL LAAAGLVRES LQAPADNAAD ARPVDVSVSI FINKIYGVNT LEQTYKVDGY
IVAQWTGKPR KTPGDKPLIV ENTQIERWIN NGLWVPALEF INVVGSPDTG NKRLMLFPDG
RVIYNARFLG SFSNDMDFRL FPFDRQQFVL ELEPFSYNNQ QLRFSDIQVY TENIDNEEID
EWWIRGKAST HISDIRYDHL SSVQPNQNEF SRITVRIDAG RNPSYYLIQM YIPSLLIVIL
SWISFWINMD AAPARVGLGI TTVLTMTTQS SGSRASLPRL PYTTVIDIWM AVCLLFVFSA
LLEYAAVNFV SRSQPARAAK IDKISRIGFP MAFLIFNMFY WIRGITL

EG2a
(SEQ ID NO: 10):
MGLRALMLWL LAAAGLVRES LQAPADNAAD ARPVDVSVSI FINKIYGVNT LEQTYKVDGY
IVAQWTGKPR KTPGDKPLIV ENTQIERWIN NGLWVPALEF INVVGSPDTG NKRLMLFPDG
RVIYNARFLG SFSNDMDFRL FPFDRQQFVL ELEPFSYNNQ QLRFSDIQVY TENIDNEEID
EWWIRGKAST HISDIRYDHL SSVQPNQNEF SRITVRIDAV RQMGYYLIQM YIPSLLIVIL
SWISFWINMD AAPARVGLGI TTVLTMTTQS SGSRASLPRL PYTTVIDIWM AVCLLFVFSA
LLEYAAVNFV SRSQPARAAK IDKISRIGFP MAFLIFNMFY WIRGITL

EG2b
(SEQ ID NO: 11):
MGLRALMLWL LAAAGLVRES LQLQAPADND ARPVDVSVSI FINKIYGVNT LEQTYKVDGY
IVAQWTGKPR KTPGDKPLIV ENTQIERWIN NGLWVPALEF INVVGSPDTG NKRLMLFPDG
RVIYNARFLG SFSNDMDFRL FPFDRQQFVL ELEPFSYNNQ QLRFSDIQVY TENIDNEEID

Class II Engineered Channel Sequences

```
EWWIRGKAST HISDIRYDHL SSVQPNQNEF SRITVRIDAV RNPSYYLIQM YIPSLLIVIL

SWISFWINMD AAPARVGLGI TTVLTMTTQS SGSRASLPRL PYTTVIDIWM AVCLLFVFSA

LLEYAAVNFV SRSQPARAAK IDKISRIGFP MAFLIFNMFY WIIYKI limiting examples, for Class II channels, the fusion sequence can be varied between the ELIC ECD ending with the C-terminal residues VRID (SEQ ID NO: 23) and the glycine receptor TMD beginning with the N-terminal residues YYLI (SEQ ID NO: 24).

In further embodiments, one or more point mutation can be introduced, such as to shift the pH response. In specific non-limiting examples, for Class 1 channels, the pH response can be shifted by modifications of the native glycine receptor sequence TQSSGSR (SEQ ID NO: 25) by changing the bold underlined residue (S16') to I, V, A or any other amino acids). In further embodiments, point mutations can be introduced to control ligand binding affinity and efficacy. Ligand binding affinity can be modified by site directed mutagenesis of the ligand-binding site, as exemplified in SEQ ID NO: 15 presented above. This sequence includes R91A and F188Y. In additional embodiments, modifications can be made to the ECD-TMD interface. The ECD-TMD interface includes, or consists of, loops 2, 7, 9, pre-TM1, the TM2-3 linker and the C-terminus. These features can be used in combination. Exemplary sequences for loops 2, 7, 9, pre-TM1, the TM2-3 linker and the C-terminus.

In further embodiments, the TM2 domain comprises at least one amino acid substitution in a wild-type TM2 amino acid sequence. The TM2 domain was conventionally defined, on the basis of hydrophobicity scoring, to be a 20-residue sequence including RVGLGITTVLTMT-TQSSGSR (SEQ ID NO: 50). The N-terminal arginine is conventionally labeled as R0', and the C-terminal arginine is conventionally labeled as R19' (see Miller, C. (1989). "Genetic manipulation of ion channels: a new approach to structure and mechanism." *Neuron* 2(3): 1195-1205, incorporated herein by reference). The nuclear magnetic resonance (NMR) structure of the human glycine receptor TM domain shows a TM2 α-helix encompassing the sequence of PARVGLGITTVLTMT<u>T</u>QSSG (SEQ ID NO: 51), namely from P-2' to G17'. In further embodiments, the chloride channel receptor includes a mutation at T13' of TM2 of the transmembrane domain. In these embodiments, the extracellular domain is the pH-gated pentameric ligand-gated ion channel (pLGIC) from *Gloeobacter violaceus*. In one non-limiting example, the mutation is a T13'S mutation, see Miller, C. (1989), supra.

In some embodiment, the chloride channel also includes a C-terminal segment of GLIC or ELIC as disclosed above. In additional embodiments, the chloride channel includes the TM4 domain of the transmembrane domain. Optionally, the chloride channel also can include a linker between the TM3 domain and the TM4 domain. Suitable linkers include, but are not limited to, the amino acid sequence comprising, or consisting of, one of (a) residues 335 and 424 of GLRA1 (SEQ ID NO: 70), (b) GGGGG (SEQ ID NO: 49), or (c) SQPARAA (SEQ ID NO: 17), or (d) HHRQANGVEDD (SEQ ID NO: 48).

In some embodiments, a chloride channel receptor is provided that includes: (a) a transmembrane domain of a glycine receptor in the absence of the extracellular and intracellular domains of the glycine receptor, wherein the transmembrane domain comprises domains TM1, TM2, TM3 and optionally TM4 (see, Haeger et al., An intramembrane aromatic network determines pentameric assembly of Cys-loop receptors. *Nat. Struct. Mol. Biol.* 17, 90 (January, 2010); and (b) an extracellular domain of a pH-gated pentameric ligand-gated ion channel (pLGIC) from *Gloeobacter violaceus* or the extracellular domain of an amine-activated pLGIC from *Erwinia chrysanthemi* (ELIC). This chloride channel also includes interfacial sequences between the extracellular domain and transmembrane domain, wherein the interfacial sequences comprise loop 2, loop, loop 9, pre-TM1 linker, TM2-TM3 linker, and C-terminus, wherein loop 2, loop 7 and loop 9 domain from *Gloeobacter violaceus, Erwinia chrysanthemi* or a human.

In some examples, the transmembrane domains TM1, TM2, TM3, include the amino acids YYLIQMYIPSL-LIVILSWISFWINMDAAPARVGLG-ITTVLTMT-TQSSGSRASLPKVSYVKAIDIWMAVCLLFVFSAL-LEYAAVNFVSR (SEQ ID NO: 26). The receptor can optionally include a TM4 including the amino acids KID-KISRIGFPMAFLIFNMFYWIIYKIVRREDVHNQ (SEQ ID NO: 27). In some embodiments, the receptor includes TM4. An exemplary ECD of a pH-gated pentameric ligand-gated ion channel (GLIC) from *Gloeobacter violaceus* includes the amino acid sequence GQDMVSPPPPIADE-PLTVNTGIYLIECYSLDDKAETFKVNA-FLSLSWKDRRLA-FDPVRSGVRVKTYEPEAIWIPEIR-FVNVENARDADVVDISVSPDGTVQYLERFSARVLSPLD FRRYPFDSQTLHIYLIVRSVDTRNIVLAVDLEKVG-KNDDVFLTGWDIESFTAVVKPANFAL EDRLESKLDY-QLRISR (SEQ ID NO: 28). An exemplary ECD of an amine-activated pLGIC from *Erwinia chrysanthemi* (ELIC), includes the amino acids

```
                                                  (SEQ ID NO: 29)
APADNAADARPVDVSVSIFINKIYGVNTLEQTYKVDGYIVAQWTGKPRK

TPGDKPLIVENTQIERWINNGLWVPALEFINVVGSPDTGNKRLMLFPDG

RVIYNARFLGSFSNDMDFRLFPFDRQQFVLELEPFSYNNQQLRFSDIQV

YTENIDNEEIDEWWIRGKASTHISDIRYDHLSSVQPNQNEFSRITVRID

AVR.
```

In some embodiments, the engineered chloride channel receptor also includes interfacial sequences between the extracellular domain and transmembrane domain, wherein the interfacial sequences comprise loop 2 (LDDKAE (SEQ ID NO: 30, glic), VNTLEQ (SEQ ID NO: 31, elic), or IAETTM (SEQ ID NO: 32, gly)), loop 7 (SPLDFRRYPFD-SQTL (SEQ ID NO: 33), NDMDFRLFPFDRQQF (SEQ ID NO: 34), or CPMDLKNFPMDVQTC (SEQ ID NO: 35)), loop 9 (GKNDDVFLT (SEQ ID NO 36, DNEEIDEWWIR (SEQ ID NO: 37) or AVQVADGLTLP (SEQ ID NO: 38)), a pre-TM1 linker (QLRISRQYF (SEQ ID NO: 39), RIDAVRNPS (SEQ ID NO: 40), or RFHLERQMG (SEQ ID NO: 41)), TM2-TM3 linker (LPKTPYMT (SEQ ID NO: 42), LPRLPYTT (SEQ ID NO: 43), or LPKVSYVK (SEQ ID NO: 44)), and C-terminus (IYFGF (SEQ ID NO: 45), RGITL (SEQ ID NO: 46), or IYKIVRREDVHNQ (SEQ ID NO: 47)), wherein the sequences are from the *Gloeobacter violaceus, Erwinia chrysanthemi*, or the human glycine receptors. Each interfacial sequence can be substituted in whole or in part by the corresponding sequence from the other, loop 2 (SEQ ID 30) can be substituted by loop 2 (SEQ ID NO:32), such as to alter the strength of the ECD-TMD interface, and thus the efficacy of the response.

In some embodiments, the chloride channel receptor is gated by certain primary amines and includes the amino acid sequence set forth as:

(SEQ ID NO: 52)

MGLRALMLWL LAAAGLVRES LQAPADNAAD ARPVDVSVSI FINKIYGVNT LEQTYKVDGX₁

IVAQWTGKPR KTPGDKPLIV ENTQIERWIN NGLWVPALEF X₁NVVGSPDTG NKX₂LMLFPDG

RVIYNARFLG SFSNDMDFRL FPFDRQQFVL ELEPX₁SYNNQ QLRFSDIQVY TENIDNEEID

EWWIRGKAST HISDIRYDHL SSVQPNQNEX₁ SRITVRIDAV RQMGYYLIQM YIPSLLIVIL

SWISFWINMD AAPARVGLGI TTVLTMTX₃QS X₄GSRASLPKV SYVKAIDIWM AVCLLFVFSA

LLEYAAVNFV SRSQPARAAK IDKISRIGFP MAFLIFNMFY WIRGITL wherein $X_1$ is W or Y; wherein $X_2$ is any uncharged or negatively charged amino acid, $X_3$ is any polar amino acid; and wherein $X_4$ is any amino acid. In specific non-limiting examples, $X_3$ is S or T. Thus, in specific examples, $X_1$ is W and $X_3$ is S, $X_1$ is Y and $X_3$ is S, $X_1$ is W and $X_3$ is T; and $X_1$ is Y and $X_3$ is T. Negatively charged amino acids include, but are not limited to, aspartic acid (D) and glutamic acid (E); polar amino acids include, but are not limited to, asparagine (N), glutamine (Q), serine (S), threonine (T) and tyrosine (Y), acidic polar resides (aspartic acid (D), glutamic acid (E)) and basic polar residues (arginine (R), histidine (H), and lysine (K)). In some embodiments, the signal sequence (shown with grey and dashed underlining) is omitted or replaced with another signal sequence.

Exemplary non-limiting amino acid sequences are set forth as one of SEQ ID NOs: 1-15 and 52. Derivatives or analogs of the receptors disclosed herein include, but are not limited to, molecules comprising regions that are substantially homologous in various embodiments, of at least 80%, 85%, 90%, 91%, 92%, 93%, 94%, 95%, 96%, 97%, 98%, 99% amino acid identity when: (i) compared to an amino acid sequence of identical size; (ii) compared to an aligned sequence in that the alignment is done by a computer homology program known within the art (e.g., Wisconsin GCG software or BLAST available on the internet) or (iii) the encoding nucleic acid is capable of hybridizing to a sequence encoding the aforementioned peptides under stringent or highly stringent conditions. See, e.g., Ausubel, et al., Current Protocols in Molecular Biology, John Wiley and Sons, New York, N.Y., 1993. These receptors retain their function.

Thus, in some embodiments, engineered chloride channel receptor are provided that are at least about 90%, at least about 91%, at least about 92%, at least about 93%, at least about 94%, at least about 95%, at least about 96%, at least about 97%, at least about 98%, or at least about 99% identical to the amino acid sequence set forth as one of SEQ ID NOs: 1-15 or SEQ ID NO: 52, wherein the engineered chloride channel receptor functions as a pH gated or amine gated chloride channel receptor. In yet another embodiment, engineered chloride channel receptors are provided that are at least about 90%, at least about 91%, at least about 92%, at least about 93%, at least about 94%, at least about 95%, at least about 96%, at least about 97%, at least about 98%, or at least about 99% identical to the amino acid sequence set forth as one of SEQ ID NOs: 1-15 or SEQ ID NO: 52, wherein the signal sequence (amino acids 1-22) is absent. Additional amino acid sequences include at most 1, at most 2, at most 3, at most 4, at most 5 conservative amino acid substitutions in one of SEQ ID NOs: 1-15 or SEQ ID NO: 52, wherein the engineered chloride channel receptor functions as a pH or amine gated chloride channel receptor. Yet other amino acid sequences include at most 1, at most 2, at most 3, at most 4, at most 5 conservative amino acid substitutions the amino acid sequence that begins at amino acid 23 of SEQ ID NOs: 1-15 or SEQ ID NO: 52, such that the signal sequence (amino acids 1-22) is absent.

In some embodiments, chloride channel receptors are provided wherein: a) the C-terminal amino acid sequence comprises one of SEQ ID NO: 18, SEQ ID NO: 19, SEQ ID NO: 20 or SEQ ID NO: 21; b) the TM1, TM2, and TM3 domains comprise the amino acid sequence set forth as SEQ ID NO: 26; SEQ ID NO: 50 or SEQ ID NO: 51, c) the TM4 domain comprises the amino acid sequence set forth as SEQ ID NO: 27; d) the extracellular domain comprises the amino acid sequence set forth as SEQ ID NO: 28 or SEQ ID NO: 29; e) the loop 2 comprises one of the amino acid sequence set forth as one of SEQ ID NO: 30-32; f) the loop 5 comprises the amino acid sequence set forth as SEQ ID NO: 61-62; g) the loop 7 comprises one of the amino acid sequences set forth as one of SEQ ID NO: 33-35; h) the loop 8 comprises the amino acid sequences set forth as SEQ ID NO: 63-64; i) the loop 9 comprises one of the amino acid sequences set forth as SEQ ID NO: 36-38; j) the loop 10 comprises the amino acid sequence set forth as 65-66; k) the pre-TM1 linker sequence comprises the amino acid sequence set forth as one of SEQ ID NOs: 39-41 or SEQ ID NOs: 59-60; and/or l) the TM2-TM3 linker comprises the amino acid sequence set forth as one of SEQ ID NOs: 42-44. In specific non-limiting examples, the extracellular domain comprises one of SEQ ID NOs: 28 or 29. These chloride channel receptors all function as pH-gated or amine gated chloride channel receptors. In some embodiments, the chloride channel receptor comprises one element from each of a)-l). Thus any of the elements listed in a) can be used with any of the elements listed in b)-l), any of the elements listed in b) can be used with any of the elements listed in a) and c)-l), etc. Optionally, the receptor includes TM4.

In some embodiments, the engineered chloride channel receptor is a pH gated (Class I) engineered chloride channel receptor that includes a loop 2, loop 7, loop 9, pre-TMl, TM1, TM2, TM3, TM3-4 liner, a C-terminus, and optionally TM4. Thus, in some embodiments the engineered chloride channel receptor includes the following elements: loop 2 (residues 52-57); loop 7 (residues 134-148); loop 9 (residues 172-180); pre-TM1 (residues 215-218); TM1 (residues 219-241); TM2 (residues 246-267); TM3 (residues 278-302); TM3-4 linker (residues 306-312); TM4 (residues 316-337); and C-terminus (residues 338-340, except for SEQ NO ID: 4, which is 338-348) of any one of SEQ ID NOs: 1-7.

The engineered chloride receptor can include the loop 2 domain from any one of SEQ ID NOs: 1-7, the loop 7 domain from any one of SEQ ID NOs: 1-7, the loop 9 domain from any one of SEQ ID NOs: 1-7, the pre-TMl domain from any one of SEQ ID NOs: 1-7, the TM1 domain from any one of SEQ ID NOs: 1-7, the TM2 domain from any one of SEQ ID NOs: 1-7, the TM2 domain from any one of SEQ ID NOs: 1-7, the TM3 domain from any one of SEQ ID NOs: 1-7, the TM3-4 linker from any one of SEQ ID NOs: 1-7, and the C-terminus from any one of SEQ ID NOs: 1-7. Optionally, the engineered chloride channel receptor includes the TM4 domain from any one of SEQ ID NOs: 1-7. In further embodiments, the loop 2, loop 7, loop 9, pre-TMI, TM1, TM2, TM3, TM3-4 liner, the optional TM4, and the C-terminus are all from one of SEQ ID NO: 1, SEQ ID NO: 3, SEQ ID NO: 4, SEQ ID NO: 5, SEQ ID NO: 6, or SEQ ID NO: 7. In some embodiments, the engineered chloride channel includes TM4.

In further embodiments, the engineered chloride channel receptor includes a loop 5, loop 8, and/or loop 10. Thus, in some embodiments the engineered chloride channel receptor also includes the following elements: loop 5 (residues 91-102); loop 8 (residues 155-159); and loop 10 (residues 197-209). Thus, the engineered chloride channel receptor includes the loop 5 domain from any one of SEQ ID NOs: 1-7, the loop 8 domain from any one of SEQ ID NOs: 1-7, and/or loop 10 from any one of SEQ ID NOs: 1-7. In more embodiments, the loop 5, loop 8 and loop 10 are all from one of SEQ ID NOs: 1-7. In yet other embodiments, the loop 2, loop 7, loop 9, pre-TMI, TM1, TM2, TM3, TM3-4 liner, the optional TM4, C-terminus, loop 5, loop 8 and loop 10 are all from one of SEQ ID NO: 1, SEQ ID NO: 3, SEQ ID NO: 4, SEQ ID NO: 5, SEQ ID NO: 6, or SEQ ID NO: 7. In some embodiments, the engineered chloride channel includes TM4.

In other embodiments, the engineered chloride channel receptor is an amine gated (Class II) engineered chloride channel receptor that includes a loop 2, loop 7, loop 9, pre-TMI, TM1, TM2, TM3, TM3-4 liner, TM4, and a C-terminus. These sequences include the following elements: loop 2 (residues 48-53); loop 7 (residues 134-148); loop 9 (residues 175-185); pre-TM1 (residues 222-225); TM1 (residues 226-248); TM2 (residues 253-274); TM3 (residues 285-309); TM3-4 linker (residues 313-319); TM4 (residues 323-342); and C-terminus (residues 343-347 for SEQ NO's ID: 9, 10, 12, 13, 15, 52, or residues 343-355 for SEQ NO's ID: 8, 11, 14) of one of SEQ ID NOs: 8-15 and 52.

Thus, the engineered chloride receptor can include the loop 2 domain from any one of SEQ ID NOs: 1-7, the loop 7 domain from any one of SEQ ID NOs: 8-15 and 52, the loop 9 domain from any one of SEQ ID NOs: 8-15 and 52, the pre-TMI domain from any one of SEQ ID NOs: 8-15 and 52, the TM1 domain from any one of SEQ ID NOs: 8-15 and 52, the TM2 domain from any one of SEQ ID NOs: 8-15 and 52, the TM2 domain from any one of SEQ ID NOs: 8-15 and 52, the TM3 domain from any one of SEQ ID NOs: 8-15 and 52, the TM3-4 linker from any one of SEQ ID NOs: 8-15 and 52, and the C-terminus from any one of SEQ ID NOs: 8-15 and 52. Optionally, the engineered chloride channel receptor includes the TM4 domain from any one of SEQ ID NOs: 8-15 and 52. In further embodiments, the loop 2, loop 7, loop 9, pre-TMI, TM1, TM2, TM3, TM3-4 liner, the optional TM4, and a C-terminus are all from one of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 52. In some embodiments, the engineered chloride channel includes TM4.

In further embodiments, the engineered chloride channel receptor includes a loop 5, loop 8, and/or loop 10. Thus, in some embodiments the engineered chloride channel receptor also includes the following elements: loop 5 (residues 91-102); loop 8 (residues 155-159); and loop 10 (residues 196-203). Thus, the engineered chloride channel receptor includes the loop 5 domain from any one of SEQ ID NOs: 8-15 and 52, the loop 8 domain from any one of SEQ ID NOs: 8-15 and 52, and/or loop 10 from any one of SEQ ID NOs: 8-15 and 52. In more embodiments, the loop 5, loop 8 and loop 10 are all from one of SEQ ID NOs: 8-15 and 52. In yet other embodiments, the loop 2, loop 7, loop 9, pre-TMI, TM1, TM2, TM3, TM3-4 liner, the optional TM4, C-terminus, loop 5, loop 8 and loop 10 are all from one of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 52. In some embodiments, the engineered chloride channel includes TM4.

Receptors, such as engineered chloride channel receptors as disclosed herein, and individual moieties or analogs and derivatives thereof, can be chemically synthesized. A variety of protein synthesis methods are common in the art, including synthesis using a peptide synthesizer. See, e.g., Peptide Chemistry, A Practical Textbook, Bodasnsky, Ed. Springer-Verlag, 1988; Merrifield, Science 232: 241-247 (1986); Barany, et al, Intl. Peptide Protein Res. 30: 705-739 (1987); Kent, Ann. Rev. Biochem. 57:957-989 (1988), and Kaiser, et al, Science 243: 187-198 (1989). The peptides are purified so that they are substantially free of chemicals or other proteins using standard peptide purification techniques.

Chemical synthesis of peptides facilitates the incorporation of modified or unnatural amino acids, including D-amino acids and other small organic molecules. Replacement of one or more L-amino acids in a peptide with the corresponding D-amino acid isoforms can be used to increase the resistance of the engineered receptors to enzymatic hydrolysis and immunogenicity, and to enhance one or more properties of biologically active peptides, e.g., receptor binding, functional potency or duration of action. See, e.g., Doherty, et al., 1993. J Med. Chem. 36: 2585-2594; Kirby, et al., 1993. J. Med. Chem. 36:3802-3808; Morita, et al., 1994. FEBS Lett. 353: 84-88; Wang, et al., 1993. Int. J. Pept. Protein Res. 42:392-399; Fauchere and Thiunieau, 1992. Adv. Drug Res. 23:127-159.

Introduction of covalent cross-links into a peptide sequence can conformationally and topographically constrain the peptide backbone. This strategy can be used to develop peptide analogs of the chimeric peptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus (Samson et al., Endocrinology, 137: 5182-5185 (1996)), or between two amino acid side chains. See, e.g., DeGrado, Adv Protein Chem, 39: 51-124 (1988). Disulfide bridges are also introduced into linear sequences to reduce their flexibility. See, e.g., Rose, et al., Adv Protein Chem, 37:1-109 (1985); Mosberg et al., Biochem Biophys Res Commun, 106: 505-512 (1982). Furthermore, the replacement of cysteine residues with penicillamine (Pen, 3-mercapto-(D) valine) has been used to increase the selectivity of some opioid-receptor interactions. Lipkowski and Carr, Peptides: Synthesis, Structures, and Applications, Gutte, ed., Academic Press pp. 287-320 (1995).

A number of other methods have been used successfully to introduce conformational constraints into peptide and receptor sequences in order to improve their potency, receptor selectivity and biological half-life. These include the use of (i) $C_\alpha$ methylamino acids (see, e.g., Rose, et al., Adv Protein Chem, 37: 1-109 (1985); Prasad and Balaram, CRC Crit Rev Biochem, 16: 307-348 (1984)); (ii) Nα-methyl-amino acids (see, e.g., Aubry, et al., Int J Pept Protein Res, 18: 195-202 (1981); Manavalan and Momany, Biopolymers, 19: 1943-1973 (1980)); and (iii) αβ-unsaturated amino acids (see, e.g., Bach and Gierasch, Biopolymers, 25: 5175-S192 (1986); Singh, et al., Biopolymers, 26: 819-829 (1987)). These and many other amino acid analogs are commercially available, or can be easily prepared. Additionally, replacement of the C-terminal acid with an amide can be used to enhance the solubility and clearance of a peptide.

Nucleic Acids, Vectors, and Host Cells

Polypeptides may be obtained by methods well-known in the art for recombinant peptide expression and purification. A DNA molecule encoding a chimeric polypeptide can be generated. The DNA sequence is deduced from the protein sequence based on known codon usage. See, e.g., Old and Primrose, Principles of Gene Manipulation 3.sup.rd ed., Blackwell Scientific Publications, 1985; Wada et al., Nucleic Acids Res. 20: 2111-2118 (1992). In some embodiments, the DNA molecule includes additional sequence, for example recognition sites for restriction enzymes which facilitate its cloning into a suitable cloning vector, such as a plasmid. Nucleic acids are provided including the coding regions, non-coding regions, or both, either alone or cloned in a recombinant vector, as well as oligonucleotides and related primer and primer pairs corresponding thereto. Nucleic acids may be DNA, RNA, or a combination thereof. Vectors can be expression vectors. Nucleic acids encoding chimeric peptides may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like). Nucleic acids can also be generated by chemical synthesis.

Derivatives of the chimeric peptides may be produced by alteration of their sequences by substitutions, additions or deletions that result in functionally-equivalent molecules. Thus, the invention includes DNA sequences that encode substantially the same amino acid sequence. In another embodiment, one or more amino acid residues within the sequence of interest may be substituted by another amino acid of a similar polarity and net charge, thus resulting in a silent alteration. Substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid. Aromatic amino acids include phenylalanine, tryptophan, tyrosine, histidine, and the unnatural amino acid tyroxine.

Nucleic acids hybridizable—or complementary—to the nucleic acids encoding the receptors disclosed herein are also provided. In particular the inverse complement to nucleic acids hybridizable to the encoding nucleic acids (i.e., the inverse complement of a nucleic acid strand has the complementary sequence running in reverse orientation to the strand so that the inverse complement would hybridize with few or no mismatches to the nucleic acid strand).

Nucleic acid molecules encoding derivatives and analogs of a chimeric receptor, or antisense nucleic acids to the same are additionally provided.

Any of the methodologies known within the relevant art regarding the insertion of nucleic acid fragments into a vector may be used to construct expression vectors that contain a chimeric gene comprised of the appropriate transcriptional/translational control signals and peptide-coding sequences. Promoter/enhancer sequences within expression vectors can be plant, animal, insect, or fungus regulatory sequences. An inducible or constitutive promoter can be operably linked to a nucleic acid encoding an engineered chloride channel receptor. In some embodiments the expression of the polypeptides encoded by the vectors are controlled by an inducible promoter, such as a promoter that directs expression specifically in neuronal cells. Suitable promoters include, but are not limited to, the doubecourtin (DCX) promoter. In other embodiments the expression of the polypeptides encoded by the vectors are controlled by a repressible promoter.

Generally, it is advantageous to transfect neuronal cells, such as neurons, with the construct. Viral vectors can be utilized for the introduction of nucleic acids, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nat. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,217,879), alphaviruses (S. Schlesinger, 1993, Trends Biotechnol. 11:18-22; I. Frolov et al., 1996, Proc. Natl. Acad. Sci. USA 93:11371-11377), human herpesvirus vectors (HHV) such as HHV-6 and HHV-7, and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors can be used. Vectors can be obtained from commercial sources (such as PharMingen, San Diego, Calif.; Protein Sciences Corp., Meriden, Conn.; Stratagene, La Jolla, Calif.). Suitable vectors are disclosed, for example, in U.S. Published Patent Application No. 2010/0247486, which is incorporated herein by reference. In specific non-limiting examples, the vectors are retrovirus vectors (for example, lentivirus vectors), measles virus vectors, alphavirus vectors, baculovirus vectors, Sindbis virus vectors, adenovirus and poliovirus vectors. Suitable vectors for stable transfection include, but are not limited to retroviral vectors, lentiviral vectors, herpesviral vectors and Sendai virus.

HSV-based vectors and methods for their construction are described in, for example, U.S. Pat. Nos. 7,078,029, 6,261,552, 5,998,174, 5,879,934, 5,849,572, 5,849,571, 5,837,532, 5,804,413, and 5,658,724, and International Patent Applications WO 91/02788, WO 96/04394, WO 98/15637, and WO 99/06583. The sequence of HSV is published (McGoech et al., J. Gen. Virol, 69 (PT 7), 1531-1574, 1988). The HSV vector can be deficient in replication-essential gene functions of only the early regions of the HSV genome, only the immediate-early regions of the HSV genome, only the late regions of the HSV genome, or both the early and late regions of the HSV genome.

In another approach to using nucleic acids, a chloride channel receptor can also be expressed by attenuated viral hosts or vectors or bacterial vectors, which can be administered to a subject. Recombinant vaccinia virus, adeno-associated virus (AAV), herpes virus, retrovirus, cytomegalovirus, poxvirus or other viral vectors can be used to express the engineered chloride channel receptors. For example, vaccinia vectors are described in U.S. Pat. No. 4,722,848. BCG (*Bacillus* Calmette Guerin) provides another vector for expression of the disclosed chloride channel receptors (see Stover, Nature 351:456-460, 1991).

Adenovirus vectors are of use in the methods disclosed herein, including replication competent, replication deficient, gutless forms thereof, and adeno-associated virus (AAV) vectors Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone.

Adenoviral vectors are often constructed by insertion of a nucleic acid encoding an engineered chloride channel receptor in place of, or in the middle of, essential viral sequences such as those found at the E1 region of adenovirus (Berkner, BioTechniques, 6:616-629, 1988; Graham et al., Methods in Molecular Biology, 7:109-128, Ed: Murcy, The Human Press Inc., 1991). Inactivation of essential viral genes by, for example, deletion or insertion, disables the adenovirus' ability to replicate. To propagate such vectors in cell culture, the deleted genes must be provided in trans (for example, the E1A and E1B proteins in the case of an E1 delete vector). These replication-defective adenoviruses are produced in packaging cells engineered to complement the replication-incompetent virus by expressing the subset of genetic elements deleted from their viral genome. Potential sites for the insertion of a nucleic acid of interest, such as a nucleic acid encoding an engineered chloride channel receptor, in recombinant adenoviral vectors include, without limitation, the E1, E2, E3 and the E4 region. In some embodiments, a recombinant adenoviral vector is produced from a human adenovirus that has the E1 region deleted and replaced with a nucleic acid encoding an engineered chloride channel receptor. The resulting viral vector, with one or more of its essential genes inactivated, is replication defective (Statford-Perricaudet et al., Human Gene Therapy, 1:241-256, 1990).

The recombinant adenovirus vectors can include: (1) a packaging site enabling the vector to be incorporated into replication-defective Ad virions; and (2) the nucleic acid encoding the engineered chloride channel receptor. Other elements of use for incorporation into infectious virions, include the 5' and 3' Ad ITRs; the E2 and E3 genes can be included in the vector. In some embodiments, a nucleic acid encoding an engineered chloride channel receptor polypeptide is inserted into adenovirus in the deleted E1A, E1B or E3 region of the virus genome. In some embodiments, the adenovirus vectors do not express one or more wild-type adenovirus gene products, such as E1a, E1b, E2, E3, E4. In some non-limiting examples, virions are typically used together with packaging cell lines that complement the functions of E1, E2A, E4 and optionally the E3 gene regions (see, for example, U.S. Pat. Nos. 5,872,005, 5,994,106, 6,133,028 and 6,127,175, incorporated by reference herein in their entirety). Adenovirus vectors can be purified and formulated using techniques known in the art.

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

Recombinant AAV (rAAV) virions can be constructed such that they include, as operatively linked components in the direction of transcription, control sequences including transcriptional initiation and termination sequences, and the nucleic acid encoding the engineered chloride channel receptor. These components are bounded on the 5' and 3' end by functional AAV inverted terminal repeat (ITR) sequences. By "functional AAV ITR sequences" is meant that the ITR sequences function as intended for the rescue, replication and packaging of the AAV virion. Hence, AAV ITRs for use in the vectors need not have a wild-type nucleotide sequence, and can be altered by the insertion, deletion or substitution of nucleotides, or the AAV ITRs can be derived from any of several AAV serotypes, provided they are functional. An AAV vector is a vector derived from an adeno-associated virus serotype, including without limitation, AAV-1, AAV-2, AAV-3, AAV-4, AAV-5, AAV-6, AAV-7, AAV-8, etc. In some embodiments, the AAV vectors have the wild type REP and CAP genes deleted in whole or part, but retain functional flanking ITR sequences. These vectors can all be used, without limitation, for the expression of an engineered chloride channel receptor.

There are numerous plasmid vectors that are known in the art for inducing a nucleic acid encoding a protein, and can be utilized. These include, but are not limited to, the vectors disclosed in U.S. Pat. No. 6,103,470; U.S. Pat. No. 7,598,364; U.S. Pat. No. 7,989,425; and U.S. Pat. No. 6,416,998, which are incorporated herein by reference.

In some embodiments, the engineered chloride channel receptors can be introduced into a host cell in vitro. The host cell can be any prokaryotic or eukaryotic cell. For example, the peptide can be expressed in bacterial cells such as *E. coli*, insect cells, fungi or mammalian cells (such as Chinese hamster ovary cells (CHO) or COS cells). Other suitable host cells are known to those skilled in the art. In one embodiment, a nucleic acid encoding the polypeptide is expressed in mammalian cells using a mammalian expression vector. Examples of mammalian expression vectors include pCD1M8 (Seed (1987) Nature 329:840) and pMT2PC (Kaufman et al. (1987) EMBO J 6: 187-195).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manual.

The host cells can be used to produce (i.e., overexpress) the receptor in culture. Methods are provided for producing the peptide using these host cells. In one embodiment, the method comprises culturing the host cell (into which a recombinant expression vector encoding the receptor has been introduced) in a suitable medium such that peptide is produced. The receptor can be isolated from the medium or the host cell (Ausubel et al., (Eds). In: Current Protocols in Molecular Biology. J. Wiley and Sons, New York, N.Y. 1998).

Compositions and Therapeutic Methods

Both acute and chronic pain, particularly ischemia- and inflammation-evoked pain such as that in severe rheumatoid arthritis, interstitial cystitis, and end-stage cancer, musculoskeletal pain, and certain forms of neuropathic pain such as trigeminal neuralgia, diabetic neuropathy, and post-herpetic neuralgia (PHN), or pain induced by herpes virus such as shingles, can be effectively managed by controlled expression of the engineered chloride channel receptors disclosed herein. Thus, methods are provided for treating a mammal for pain, such as physical pain induced by nociceptors, by administering a pharmaceutical composition in order to produce analgesia in the subject. Treatment can be achieved with localized and targeted nucleic acid, vector or protein delivery around afferent nerve fibers or through widespread gene transfer in the terminals of peripheral sensory neurons. Treatment can include intrathecal or selective perineural administration. Methods are also provided for the treatment of cystic fibrosis or asthma.

The condition, such as pain, cystic fibrosis or asthma does not need to be completely eliminated for the composition to be effective. For example, a composition can decrease the condition by a desired amount, for example by at least 10%, at least 20%, at least 50%, at least 60%, at least 70%, at least 80%, at least 90%, at least 95%, at least 98%, or 100%, as compared to the condition in the absence of the composition.

Compositions are provided that include one or more of the chloride channel receptors, and nucleic acids encoding these chloride channel receptors that are disclosed herein in a carrier. The compositions can be administered systemically or locally. The compositions can be prepared in unit dosage forms for administration to a subject. The amount and timing of administration are at the discretion of the treating physician to achieve the desired purposes. The compositions can be formulated for systemic or local administration. In one example, chloride channel receptor is formulated for parenteral administration, such as intravenous administration. In another example, the expression sequences for the chloride channel receptor are inserted in a viral vector for intrathecal or perineural injection.

Administration into the airways can provide either systemic or local administration, for example to the trachea and/or the lungs. In some embodiments the receptors, nucleic acids or vectors are administered by inhalation or using a nebulizer, such as for the treatment of asthma or cystic fibrosis. Such administration can be made via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or noon-aerosol spray of a liquid. Pressurized packs can comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhalator or insufflator.

In some embodiments, administration can also be by transmucosal means. For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhaled aerosols, suppositories, mouthwashes, rapidly dissolving tablets, or lozenges.

In one non-limiting example, the method includes intraventricular infusion into the central nervous system. Infusion can also be introduced into the cerebral spinal fluid or by interstitial delivery to the central nervous system. For example, the chloride channel receptor, or a nucleic acid encoding the receptor, can be introduced using a cannula and an osmotic pump. The chloride channel receptor, or a nucleic acid encoding the receptor, can be infused intraventricularly using an Ommaya reservoir, a plastic reservoir implanted subcutaneously in the scalp and connected to the ventricles within the brain by an outlet catheter. Solutions can be subcutaneously injected into the implanted reservoir and delivered to the ventricles by manual compression of the reservoir through the scalp. Several implantable pumps have been developed that possess several advantages over the Ommaya reservoir. These can be implanted subcutaneously and refilled by subcutaneous injection and are capable of delivering drugs as a constant infusion over an extended period of time. Furthermore, the rate of drug delivery can be varied using external handheld computer control units.

In some embodiments, direct intraneural and perineural injection of the engineered chloride channel receptors or their expression vectors is efficacious therapy. For ilioinguinal nerve entrapment syndrome caused by never damages from trauma or from inguinal herniorrhaphy and pelvic surgery, ultrasound-guided injection into or around ilioinguinal nerve can be used. For occipital neuralgia and migraine headache, ultrasound-guided injection into the greater occipital nerve can be used. For swimmer's headache and supraorbital neuralgia, peri-supraorbital nerve injection can be used. For suprascapular nerve entrapment and chronic shoulder pain, ultrasound- or X-ray-guided suprascapular nerve injection can be used. For herpes zoster or shingles pain in the chest, for pain around a chest scar after a chest surgery, or chest pain caused by trauma or rib fracture, ultrasound- or X-ray-guided intercostal nerve injection can be used. For meralgia paresthetica, perineural injection around the lateral femoral cutaneous nerve can be used. For cervical or lumbar facet pain syndrome, direct cervical or lumbar medial branch injection under X-ray or ultrasound guidance can be used.

Methods are provided herein for treating chronic pain. For example, in one embodiment, the chloride channel, nucleic acids encoding the chloride channel, and vectors including these nucleic acids can be used for treating chronic nerve pain in a subject, such as a human. In some embodiments, in accordance with the method, the area of pain in the subject is identified, and the spinal level within the mammal that is associated with the chronic pain is determined. A delivery device is used to introduce the chloride channel, nucleic acids encoding the chloride channel, and vectors including these nucleic acids at the location of the DRG associated with the chronic pain.

A delivery device can be utilized the chloride channel, nucleic acids encoding the chloride channel, and vectors including these nucleic acids, see for example, Published U.S. Patent Application No. 2012/0310140. The spinal nerves include both dorsal and ventral roots that integrate near the intravertebral foramen to create a mixed nerve which is part of the peripheral nervous system. At least one dorsal root ganglion (DRG) is disposed along each dorsal root prior to the point of mixing. Thus, the neural tissue of the central nervous system is considered to include the dorsal root ganglions and exclude the portion of the nervous system beyond the dorsal root ganglions, such as the mixed nerves of the peripheral nervous system. Typically, the chloride channel, nucleic acids encoding the chloride channel, and vectors including these nucleic acids, as disclosed herein, are used to neuromodulate one or more spinal anatomy, for example, but not limited to one or more dorsal root ganglia. In some embodiments, the deliver minimizes or excludes undesired treatment of other tissues, such as surrounding or nearby tissues, ventral root and portions of the anatomy associated with body regions which are not targeted for treatment.

The compositions for administration can include a solution of the chloride channel receptor, or a nucleic acid encoding the chloride channel receptor, dissolved in a pharmaceutically acceptable carrier, such as an aqueous carrier. The compositions can include a nanoparticle comprising the ion channel, such as the chloride channels disclosed herein. A variety of aqueous carriers can be used, for example, buffered saline and the like. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, natural lipids and the like. The concentration of chloride channel receptor in these formulations can vary widely, and will be selected primarily based on fluid volumes, viscosities, body weight and the like in accordance with the particular mode of administration selected and the subject's needs.

A typical pharmaceutical composition for intravenous administration includes about 0.01 to 10 mg of protein per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

In some embodiments, the engineered chloride channel receptor can be directly delivered in the protein form by being wrapped in nano-scale lipid vesicles (nanoparticles), such as for the unmyelinated C-fibers. In some non-limiting examples, the nanoparticles are less than 300 nm in size, are less than 200 nm in size, or are less than 100 nm in size.

In some embodiments, a small peptide derived from rabies virus glycoprotein can be attached on the surface of the nanoparticles to increase the efficiency of specific neuronal incorporation of the nanoparticles. In some non-limiting examples, short peptides with selective homing properties for peripheral nerves, such as NP41 (NTQT-LAKAPEHT (SEQ ID NO: 53 see PCT Publication No. WO2010121023, corresponding to PCT Application No. PCT/US2010/031231) or Tet1 (HLNILSTLWKYR (SEQ ID NO: 54, see PCT Publication No. WO2011066285, corresponding to PCT Application No. PCT/US2010/057809) can be used to functionalize the surface of nanoparticles to selectively deliver the engineered channels or their expression vectors to the peripheral nerves. In other non-limiting examples, the octapeptides RPPGFSPF (SEQ ID NO: 55) and/or KPPGFSPF (SEQ ID NO: 56) or the nonapeptides KRPPGFSPF (SEQ ID NO: 57) and/or KKPPGFSPF (SEQ ID NO: 58) can be used to functionalize nanoparticles. These nanoparticles selectively target the bradykinin 1 receptor, which is expressed most abundantly in inflammation-injured afferents.

Chloride channel receptors pre-encapsulated in lipid vesicles may be provided in lyophilized form and rehydrated with sterile water before administration, although they are also provided in sterile solutions of known concentration. The solution is then added to an infusion bag containing 0.9% sodium chloride, USP, and typically administered at a dosage of from 0.5 to 15 mg/kg of body weight.

A therapeutically effective amount of a nucleic acid encoding the chloride channel receptor, or a vector including the nucleic acid, can be administered to a subject. One approach to administration of nucleic acids is direct immunization with plasmid DNA, such as with a mammalian expression plasmid. The nucleotide sequence encoding the chloride channel receptor can be placed under the control of a promoter to increase expression of the molecule. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids to an organism. The methods include liposomal delivery of the nucleic acids.

In one embodiment, a nucleic acid encoding the chloride channel receptor is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites, such as nerves damaged by shingles. Dosages for injection are usually around 0.01 to about 5 mg per injection, and typically are about 0.005 mg/kg to about 5 mg/kg (see, e.g., U.S. Pat. No. 5,589,466).

A therapeutically effective amount of a chloride channel receptor (or the nucleic acid encoding the chloride channel receptor) will depend upon the severity of the disease and/or infection and the general state of the patient's health. A therapeutically effective amount of the receptor is that which provides either subjective relief of a symptom(s) or an objectively identifiable improvement as noted by the clinician or other qualified observer. These compositions can be administered in conjunction with another therapeutic agent, either simultaneously or sequentially.

In non-limiting examples, the subject can also be administered an effective amount of an additional agent, such as an analgesic or a bronchodilator. The methods can include administration of one or more additional agents known in the art, including but not limited to systemic administration of NSAIDs, COX-2 inhibitors, opioids, cannabinoids, and antidepressants, or localized administration of long-acting local anesthetics or anti-inflammatory steroids through epidural injections, transforaminal epidural injections, sacrolliac joint injections, facet joint injections, lumbar sympathetic blockage, stellate ganglion blockage, and intrathecal pump implant. One of skill in the art can readily identify appropriate agents for administration to a subject, depending on the condition being treated.

In one embodiment, administration of the chloride channel receptor (or nucleic acid encoding the chloride channel receptor) results in a reduction a symptom of the condition in a subject. In some embodiments, methods are disclosed for treating a subject with asthma, cystic fibrosis or pain, such as pain from diabetic neuropathy, shingles, or musculoskeletal pain. These methods include administering to the subject a therapeutically effective amount of a chloride channel receptor, or a nucleic acid encoding the receptor, thereby preventing or treating the condition.

Single or multiple administrations of the compositions including the chloride channel receptor, or nucleic acid encoding the chloride channel receptor, that are disclosed herein, are administered depending on the dosage and frequency as required and tolerated by the patient. In any event, the composition should provide a sufficient quantity of at least one of the chloride channel receptors disclosed herein to effectively treat the subject. The dosage can be administered once but may be applied periodically until either a therapeutic result is achieved or until side effects warrant discontinuation of therapy. The subject can be treated at regular intervals, such as monthly, every two month, every six month, yearly, or every other year until a desired therapeutic result is achieved. Generally, the dose is sufficient to treat or ameliorate symptoms or signs of disease without producing unacceptable toxicity to the patient.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a chloride channel receptor, as a central core. In microspheres the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously, intramuscularly, or perineurally. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the chloride channel receptor compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

In some examples, a subject is administered the DNA encoding the chloride channel receptor thereof to provide in vivo production, for example using the cellular machinery of the subject. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding to an organism. The methods include liposomal delivery of the nucleic acids. Such methods can be applied to the production of a chloride channel receptor by one of ordinary skill in the art.

In some embodiments, the chloride channel receptor is activated by pH, and thus natural processes such as inflammation activate the chloride channel. In other embodiments, the chloride channel receptor is activated by another agent, such as, but not limited to, a small molecule or an amine. Once the chloride channel is administered to the subject, the activating agent, such as the small molecule or the amine, can be administered to the subject. The activating agent can be administered using any method known to one of skill in the art.

Activation of an Engineered Channel Receptor by an Exogenous Compound

As disclosed above, in some embodiments, the engineered channel receptor is activated by a exogenous molecule, such as a small molecule, for example an amine or a ligand. In some embodiments, the channel is activated by an activating molecule such as a primary, secondary, tertiary or quaternary amine or a ligand. In particular embodiments, the activating molecules are primary amines such as cysteamine or propylamine. In other non-limiting examples, the activating molecules are N-3-pyridinyl-methanimidamide, 3-(2-aminoehtyl)pyridine, oxolan-3-yl carbamimidothioate, 2-(3,4-dimethylcyclopent-3-en-1-yl)ethanamine, butyramidine, salicylamide, stavudine, chlorzoxazone, betazole, and pralidoxime. In yet other non-limiting examples, 2-(aminomethyl)phenol, 2-(aminomethyl)phenyl acetate, o-xylylamine, 1-[2-(aminomethyl)phenyl]ethanone, and o-anisylamine can be used as activating molecules. In other non-limiting examples, amine is choline, or acetylcholine.

An effective amount of the activating molecule is then administered to the subject for treatment. For example, the activating molecule can be sufficient to reduce pain, treat asthma, or treat cystic fibrosis.

For use in vivo, administration of the activating agent can be systemic or local. Any route of administration can be used.

In one specific, non-limiting example, the therapeutically effective amount the activating agent, such as the small molecule, is administered by injection into a ventricle of the central nervous system, administration into the spinal cord, or administration to a specific dorsal root ganglion. In several embodiments, any local administration can used, as discussed above.

In one non-limiting example, the method includes intraventricular infusion into the central nervous system. Infusion can also be infused into the cerebral spinal fluid or by interstitial delivery to the central nervous system. For example, the agents can be introduced using a cannula and an osmotic pump. The activating molecule can be infused intraventricularly using an Ommaya reservoir. Solutions including the activating molecule can be subcutaneously injected into the implanted reservoir and delivered to the ventricles by manual compression of the reservoir through the scalp. Several implantable pumps have been developed that possess several advantages over the Ommaya reservoir. These can be implanted subcutaneously and refilled by subcutaneous injection and are capable of delivering the activating molecule as a constant infusion over an extended period of time. Furthermore, the rate of delivery of the activating molecule can be varied using external handheld computer control units.

Compositions including an activating molecule can be delivered by way of other types of pumps (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as are deemed appropriate by the practitioner. Other controlled release systems are discussed in Langer (Science 249:1527-33, 1990).

In some embodiments, the subject can control release of the activating molecule, so as to control their own pain. In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the activating agent into the subject's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular other embodiments, the methods include administering the activating molecules by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

The disclosure is illustrated by the following non-limiting Examples.

EXAMPLES

Chronic pain affects more people than cancer, heart disease, and diabetes combined. Nearly all currently available pain medications are complicated by adverse action in the central nervous system with undesirable risks of drug toxicity, tolerance, dependence, and abuse. A fundamentally different approach to a yet unexplored mechanism of analgesia is achieved by directly modifying peripheral nociceptors with non-native, engineered Cl⁻ channels. These channels serve as antihyperalgesic responders to small nontoxic molecules that would otherwise have negligible or no analgesic action. In vivo expression of the engineered channels in peripheral nerve endings and dorsal root ganglia in rats resulted in little measurable interference with nociceptive and tactile function under normal physiological conditions. Alleviation of inflammation-induced pain became highly significant after a small non-psychoactive molecule activated the engineered channels. The results demonstrate the clinical potential of a new class of analgesics that are not only efficacious for treating acute and chronic pain, but also intrinsically devoid of any centrally acting side effects or abuse potential.

Example 1

Generation of Receptors

DNA encoding the engineered protein sequences detailed as SEQ ID NOs: 1-15, see above, were constructed by overlapping PCR from cDNAs for ELIC (Echr-26-pelB-H10), GLIC (pcDNA3.1-GLIC) and the human α1 glycine receptor (phgSK-), and modified as described above using QUIKCHANGE® Lightning Site-Directed Mutagenesis Kits (Agilent). For in vivo experiments, these constructs were subcloned into a plasmid vector comprising the IRES-eGFP cassette from Retro-CL-BMP2/4-IRES-eGFP and the mammalian expression vector pAAV-CMV-SV40polyA. The engineered proteins were inserted upstream of the IRES fragment such that eGFP is translated from the same RNA transcript, serving as an easily visualized marker of expression. All constructs were confirmed by sequencing in full.

Example 2

Electrophysiology

Channel function was measured by two-electrode voltage clamp experiments using *Xenopus laevis* oocytes (stages 5-6) injected with 20-50 ng of the desired construct in the pAAV vector as described above. Oocytes were maintained at 18° C. in modified Barth's solution containing 88 mM NaCl, 1 mM KCl, 2.4 mM NaHCO3, 15 mM HEPES, 0.3 mM Ca(N03)2, 0.41 mM CaCl2, 0.82 mM MgSO4, 10 μg/ml sodium penicillin, 10 μg/ml streptomycin sulphate, and 100 μg/ml gentamycin sulphate, pH 6.7. After 1-3 days expression, oocytes were clamped with an OC-725C Amplifier (Warner Instruments) to a holding potential of −60 mV in a 20-μl oocyte recording chamber (Automate Scientific) and currents elicited using pH, cysteamine or propylamine as agonists. The recording solutions contained 130 mM NaCl, 0.1 mM $CaCl_2$, 10 mM HEPES, pH 7.0 with the indicated concentrations of agonists. For pH measurements, 10 mM MES was added. For ion selectivity measurements, asymmetric IV curves were measured with 130 mM NaCl, choline chloride, or sodium gluconate in the external solution. Data were collected and processed using Clampex 10 software (Molecular Devices). Non-linear regressions were performed using Prism software (Graphpad). A 50-mV shift in reversal potential upon replacing Cl− with gluconate and no significant shift upon replacing Na+ with choline indicate a Cl− selective channel with negligible Na+ contribution to the current. (FIG. 2).

Figure 3B:
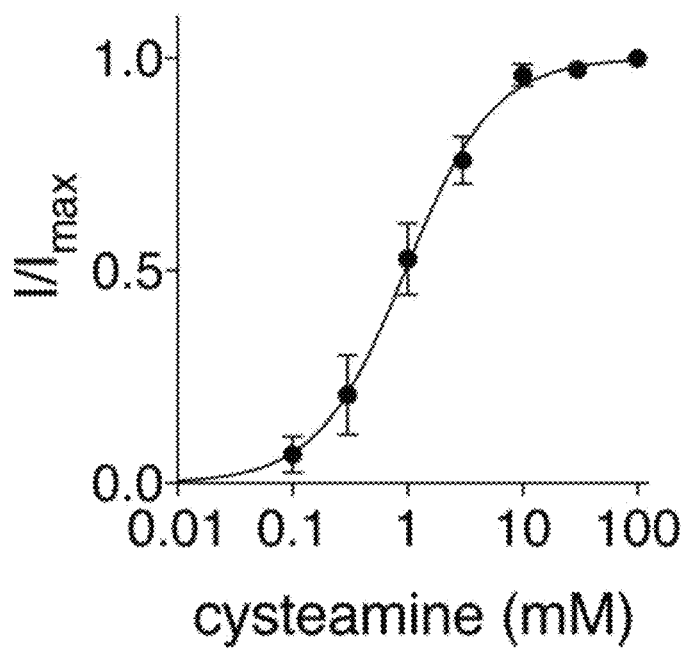
Figure 6A:
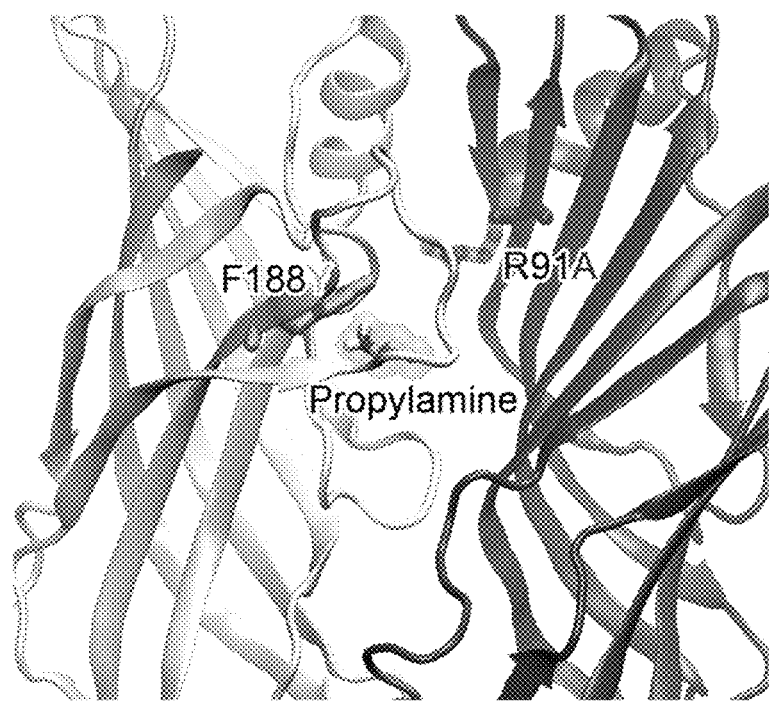
FIGS. 6A-6B. Structure Engineering for Targeted Drugs.
Figure 6B:
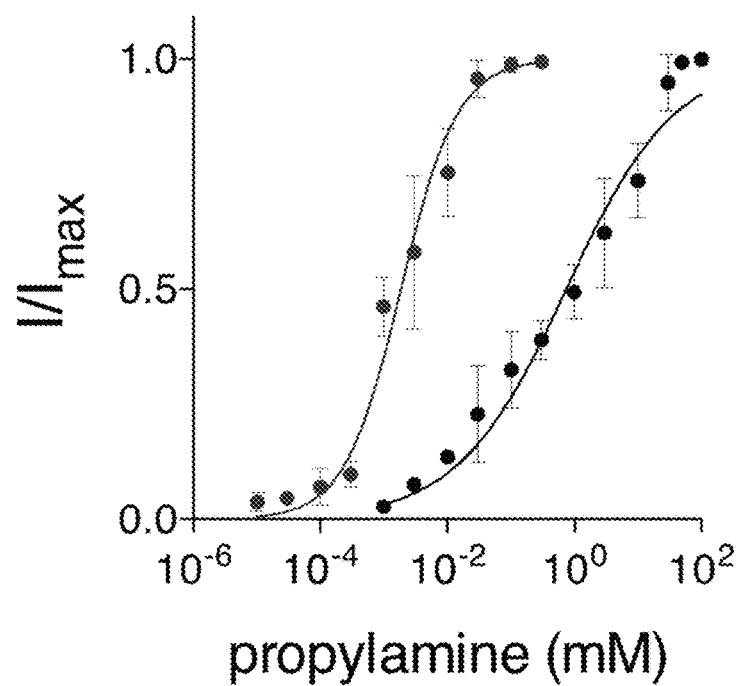

For the pH-gated GG channels (Class I), a single mutation site was identified in the TM2 domain (S16') where the $EC_{50}$ for pH can be shifted by varying the side chain size and hydrophobicity at this location, thereby fine-tuning the amount of hyperpolarization of the afferents in proportion to the degree of inflammation. As shown in FIG. 3A, Cl− currents through four different engineered GLIC-GlyR channels were activated by changing the extracellular pH, mimicking varying degrees of inflammatory condition. The data were fit to Hill equations with $pH_{50s}$ of 7.34±0.02, 7.04±0.03, 6.72±0.07, and 6.10±0.04 for the four designs S16', S16'A, S16'V, and S16'I, respectively. Hill slopes were ~2. For the EG channel (Class II), Cl− current could be activated by applying small amine molecules such as propylamine or cysteamine. As shown in FIG. 3B), Cl− currents through EG3 (SEQ ID NO: 12) were activated by a cysteamine in a concentration-dependent manner. The data were fit to a Hill equation with an $EC_{50}$ of 0.96±0.12 mM cysteamine and a Hill slope of 1.1±0.1. In another example, engineered channels as in SEQ ID NO: 15 are activated by propylamine and cysteamine with 5- to 1000-fold increase in efficacy, as shown in FIG. 6.

Example 3

Transgenic Studies

Figure 4:
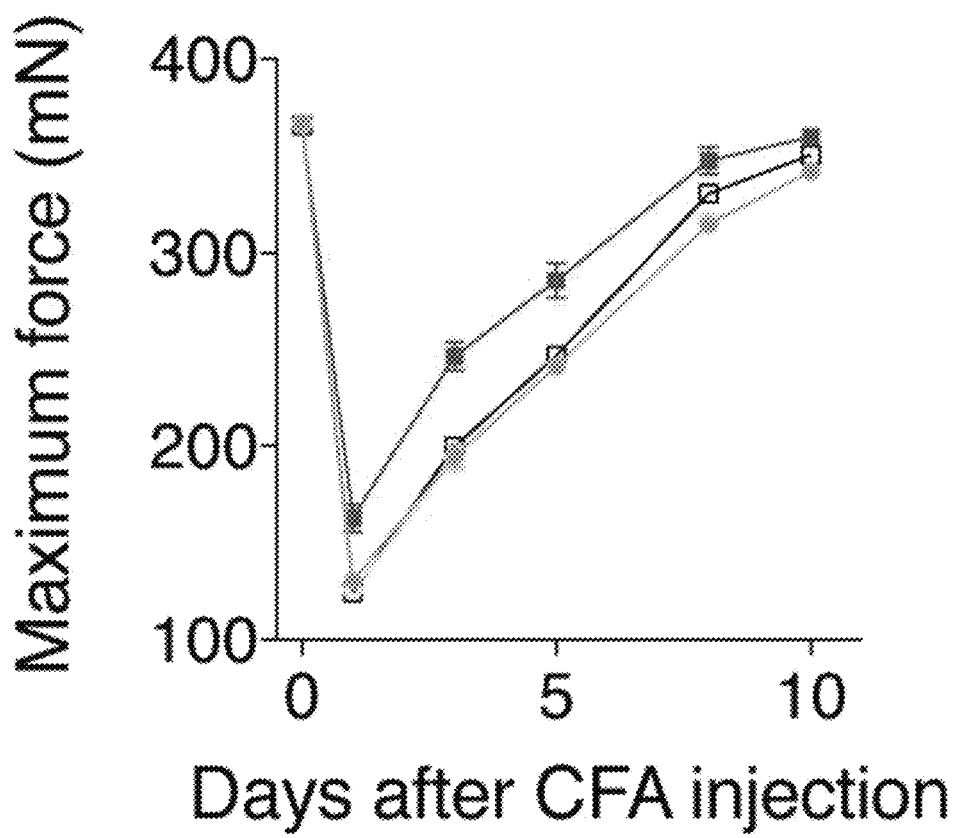
FIG. 4. Alleviation of pain by the engineered Cl⁻ channels. Behavioral Von Frey test of the maximum force tolerance after the injection of the inflammatory irritant CFA: engineered EG channel without cysteamine (□); EG channel+cysteamine (■); control vector (○), and control vector+cysteamine (●).

The receptors were tested in vivo in rats for treatment of inflammation pain (FIGS. 4 and 5). To test the efficacy of the designed channel to alleviate inflammatory pain, EG3 (SEQ ID NO: 12) was inserted into an expression vector in which the CMV promoter expresses a single transcript consisting of the EG sequence followed by an enhanced green fluorescence protein (eGFP) sequence, separated by an internal ribosome entry site (IRES) such that each protein is translated independently. Since the proteins are expressed on the same mRNA transcript but translated independently, expression of eGFP confirms expression of the mRNA transcript encoding EG. The plasmid was injected (500 μg in 100 μl subcutaneously) around the peripheral nerve of the hind paw of rats and expression of eGFP was confirmed by fluorescence microscopy. As shown in FIG. 5, expression was found not only in the peripheral nerve fibers, but also in the dorsal root ganglia (DRG) due to retrograde migration of the expression vector.

In one experiment, 8 rats were assigned to two groups to receive either EG expression plasmid or the control plasmid before the EG insertion. The proteins (EG channel and eGFP) were allowed to express for a week in vivo. Thereafter, inflammation was induced in the same hind paw by complete Freund's adjuvant (CFA) injection (50 μl). Hypersensitivity was measured using a Von Frey pain-testing device after CFA injection. This test measures the maximum force applied to the paw through a flexible thin wire before paw withdrawal. Note that this version of the channel design, EG3 (SEQ ID NO: 12), requires a small agonist molecule (propylamine or cysteamine) to open the Cl− channels. As shown in FIG. 4, over 10 days after CFA injection, the pain scores followed the same trend for rats in both groups before cysteamine injection, suggesting that the engineered EG channel, when not activated, did not produce measurable changes in the peripheral nerves. After cysteamine administration, the pain scores significantly improved in the EG group but not in the control group, suggesting that cysteamine is normally not an analgesic (as shown in the control group) but is turned into a potent analgesic in the presence of the engineered receptor.

In addition to the direct injection of plasmid DNA, which is known to be inefficient for gene transfer in vivo, various other delivery strategies were investigated. Replication-deficient genomic herpes simplex virus (HSV) naturally attacks peripheral nerves and will be considered as a candidate. Recombinant adeno-associated virus (rAAV) is considered a safer choice because it has an extremely rare chance of chromosomal insertion. No known human diseases are currently linked to rAAV. Intrathecal injection of rAAV serotype 8 in rats showed a widespread expression of the transgene in the peripheral sensory neurons and nerve fibers (FIG. 5). Interestingly, very little transgene expression was found in the peripheral motor nerves. This can be a desirable feature, as it will minimize the effects of engineered receptor on motor functions.

Example 4

Receptor Engineering to Lessen Inflammation-Evoked Pain & Hyperalgesia

An effective strategy is provided herein to create analgesic targets in the peripheral nervous system (FIG. 8A). The transmembrane (TM) domain of the human glycine receptor (GlyR) a1 subunit, without the extracellular glycine-binding domain and the intracellular domain, can spontaneously form Cl⁻ conducting channels. Despite being the major inhibitory receptors in the spinal cord and brainstem, GlyRs are absent in the primary afferents (Gross et al., *Mol Ther* 19, 500, 2011). Thus, a pharmacologically controllable inhibition of afferent propagation, in addition to shunting inhibition (Prescott and De Koninck, *Proc. Nat Acad. Sci.* 100, 2076, 2003) and presynaptic inhibition via primary afferent depolarization in the spinal dorsal horn (Willis et al., *Experimental brain research. Experimentelle Hirnforschung. Experimentation cerebrale* 124, 395, 1999), offers an attractive therapeutic modality. To achieve pharmacological control of the inhibitory channel activation without interference with the endogenous glycinergic and GABAergic activities in the CNS, the GlyR TM domain was fused downstream of the extracellular ligand-binding domain (FIG. 8B) of an amine-activated pentameric ligand-gated ion channel from *Erwinia chrysanthemi* (ELIC). The resulting ELIC-GlyR (EG) chimera channel (FIG. 8C) was further optimized to increase the agonist sensitivity (see Example 6 for details).

This approach is supported by an in vitro study showing effectiveness of the ivermectin-sensitive invertebrate GluCl channel to selectively reduce the excitability of mammalian neurons (14). The EG channel can be dose-dependently activated by cysteamine to open a Cl⁻-selective pore (FIG. 8D), with negligible permeability to cations (FIG. 8E). Cysteamine was chosen as an agonist for proof of concept because cysteamine is a prescription drug in clinical use for treating cystinosis, and it is safe with no psychoactive effects (see Kaiser-Kufer et al., *N Engl J Med* 316, 775, 1987; Kleta and Gahl, *Expert Opin Pharmacother* 5, 2255, 2004). To test the efficacy of the engineered channel to alleviate inflammatory pain, the EG sequence was inserted into an expression vector in which the CMV promoter expressed a single transcript comprising the EG sequence followed by an enhanced green fluorescence protein (eGFP) sequence, separated by an internal ribosome entry site (IRES) such that each protein is translated independently. The expression of the downstream reporter protein eGFP indicates the expression of EG.

Figure 10A:
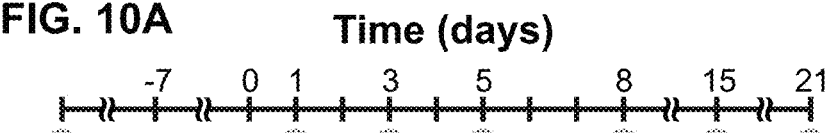
FIGS. 10A-10C. Alleviation of thermal hyperalgesia and mechanical allodynia by the engineered Cl⁻ channels.

Rats were randomly assigned to two groups to receive a subcutaneous injection of 1 mg (in 200 µl) purified EG expression vector into the left hind paw or the control plasmid vector without the EG insertion in an identical fashion. The EG expression was assessed using fluorescence microscopy by visualizing eGFP, which was readily detectable one week after the vector injection and lasted for over six weeks. The expression is abundant not only in the peripheral nerve fibers, but also in the dorsal root ganglion due to retrograde migration of the expression vector (FIG. 9). To induce chronic inflammation, 50 µg (in a 50-µl volume) of complete Freund's adjuvant (CFA, see Sandkuhler, *Physiol Rev* 89, 707 (April, 2009) was injected into the same left hind paw one week after the vector injection. Thermal and mechanical hypersensitivity and allodynia were assessed by behavioral tests using the Hargreaves (Hargreaves et al., *Pain* 32, 77, 1988) and the von Frey (Lariviere et al., *Pain* 97, 75 (May, 2002) methods, respectively. The timeline for the in vivo experiments is depicted in FIG. 10A. Before CFA-induced inflammation, neither EG nor the control plasmids caused measurable changes in basal mechanical and thermal thresholds. After CFA injections, the rats were tested both before and after cysteamine administration to assess the specific analgesic effects from the expressed EG channels.

Figure 10B:
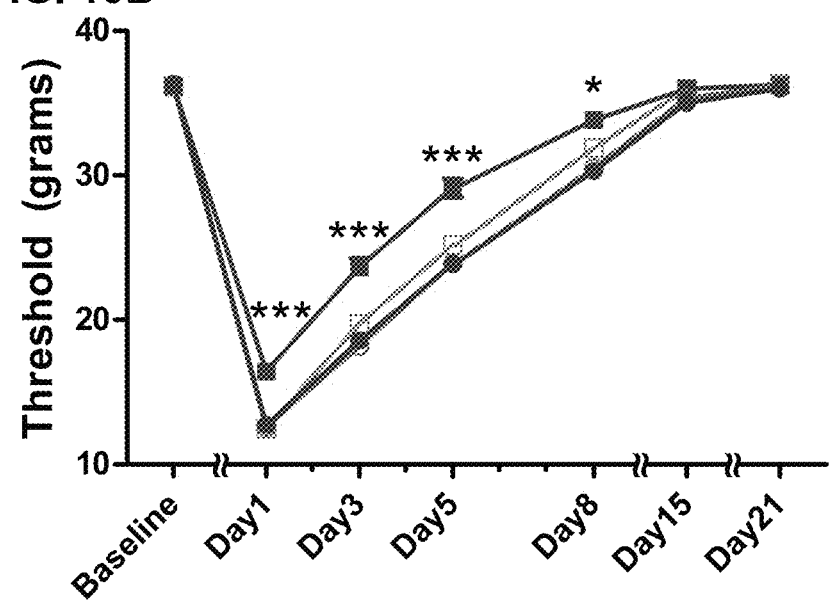
Figure 10C:
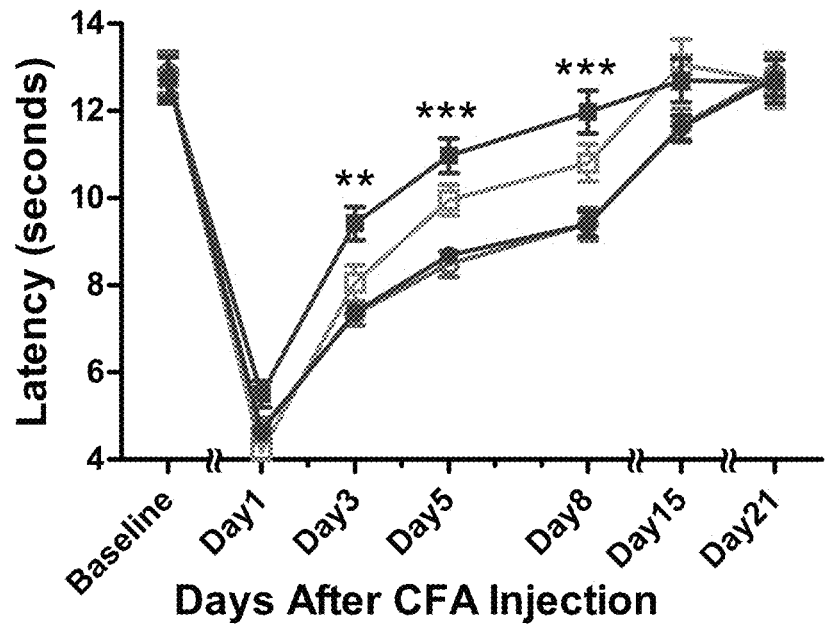

The time course of inflammation-induced allodynia followed the same trend in both animal groups before cysteamine administration (FIG. 10B), indicating that the engineered EG channels, when not activated, produced little measurable changes in mechanical nociception. Hypersensitivity to heat-induced pain was partially alleviated in the EG group compared to the control group even before channel activation by cysteamine (FIG. 10C). This is likely due to residual leak currents through the engineered channels and their differential association with the mechanical and thermal nociceptors. After cysteamine administration, both thermal and mechanical hypersensitivities to inflammation-induced pain are significantly attenuated in the EG group but not in the control group, indicating that cysteamine is not inherently an analgesic (as shown in the control group) but is turned into a potent analgesic in the presence of the engineered receptor. The cysteamine's ability to alleviate pain can be attributed to the inhibitory action mediated by the activation of the engineered channel.

The results demonstrated a new strategy, in which small drug-like molecules with negligible or no intrinsic analgesic effects can now be selected and used as potent painkillers. This represents a fundamentally different approach to a yet unexplored mechanism of analgesia by directly modifying peripheral nociceptors with the engineered ion channels disclosed herein. Through the design of activators and channel receptors in pairs, it is now feasible to remove any unwanted psychoactive potential altogether. Without being bound by theory, three possible mechanisms can explain the observed analgesic effects from the installed Cl⁻ selective EG channels. First, in neurons with functional KCC2 channels, the anion reversal potential follows that of $E_{K+}$, which is significantly more negative than the resting potential (Staley, *Epilepsy currents/American Epilepsy Society* 8, 107, 2008). In these neurons, as most peripheral afferents are, opening Cl⁻ channels is accompanied by a hyperpolarization shift of the axonal membrane potential, resulting in an increase of pain threshold. Second, although several ex vivo studies suggested a depolarization shift of anion reversal potential in spinal lamina I neurons (Couli et al., *Nature* 424, 938 (Aug. 21, 2003) and in CNS after neuronal injuries (van den Pol et al., *The Journal of neuroscience: the official journal of the Society for Neuroscience* 16, 4283, 1996) very few accurate in vivo electrophysiology measurements of intracellular Cl⁻ concentration in peripheral nerves have been reported because such in vivo measurements are considerably more difficult than ex vivo measurements without carefully controlling both systemic and regional $pCO_2$ and $HCO_3^-$ as well as cation gradients. If the ex vivo results are mirrored under certain in vivo conditions, opening Cl⁻ channels would be expected to lead to further membrane depolarization. Indeed, down-regulation of KCC2 and a depolarization shift of anion gradients after nerve injuries have been considered as a possible mechanism of neuropathic pain. However, the fact that the data showed robust analgesia against inflammatory pain suggested a net inhibitory effect, or an antihyperalgesic effect, from the installed Cl⁻ channels. It should be noted that even with the degree of the depolarization shift as observed in the in vitro and ex vivo preparations, the anion reversal potential is still significantly more negative than the spike initiation potential, which always drives a Cl⁻ influx. Thus, the action of the expressed EG Cl⁻ channels can still be inhibitory as a result of shunting (Precott and De Koninck, supra; Price et al., *Brain research reviews* 60, 149, 2009). In addition, the expression of EG channels in the primary afferent terminals in the spinal dorsal horn could suppress excitatory neurotransmitter release through the same mechanism as presynaptic inhibition by the primary afferent depolarization (Rudomin and Schmidt, *Experimentelle Hirnforschung Experimentation cerebrale* 129, 1999). A variety of small molecules without psychoactive action can be chosen to activate the engineered channels.

Example 5

Additional Materials and Methods

ELIC-GlyR (EG) Chimera Design and Analysis:

The EG chimera was constructed by fusing the extracellular domain of ELIC with the transmembrane domain of the al subunit of human GlyR. Five constructs were made to test the importance of interface elements at the fusion junction (pre-TM1), the loop between transmembrane helices 2 and 3 (TM23), and C-terminus (Figure S1a). In addition, the long cytoplasmic loop was removed to facilitate homogeneous expression (i.e., "VSR . . . KID" was replaced with "VSRSQPARAAKID"). All designed constructs expressed functional channels in *Xenopus* oocytes and were responsive to the agonist cysteamine. The constructs mostresponsive to cysteamine, EG and EGd (Figure S1b), included a native GlyR TM23 loop and an ELIC C-terminus (Figure S1). The fusion junction had less effect on cysteamine response (compare EG and EGd). Replacing the GlyR TM23 loop with the ELIC TM23 loop interfered with the cysteamine response (compare EGc and EGd), perhaps due to disruption of normal interactions between the TM23 loop and the rest of the transmembrane domain.

EG was subcloned into the mammalian expression vector pAAV-CMV-SV40polyA expressing an RNA transcript containing EG, followed by an internal ribosome entry site (IRES) and an enhanced green fluorescence protein (eGFP) as a marker for EG expression.

Electrophysiology:

The ion selectivity and function of the EG channels were measured by two-electrode voltage clamp experiments {Dascal, 2001 #2410} with *Xenopus laevis* oocytes injected with DNA encoding the indicated constructs. After 1-2 days of channel expression, the oocytes were clamped to a holding potential of −60 mV. The recording solutions for EG contained 130 mM NaCl, 0.1 mM CaCl2, 10 mM HEPES, pH 7.0 with the indicated concentrations of cysteamine. Nonlinear regressions of the data were performed using Prism (Graphpad) software.

Animals, Plasmid DNA Injection, and Inflammatory Pain Model:

The Institutional Animal Care and Use Committee at the University of Pittsburgh approved all animal procedures used in the studies. Male Sprague-Dawley rats, weighing 220-250 g, were obtained from Harlan Laboratories, allowed to acclimate to the housing and experimental facilities, evaluated for baseline behavioral response to thermal and mechanical pain, and then subjected to inflammatory pain model and behavioral testing. The expression vectors, 1000 µg in a volume of 200 µl phosphate-buffered saline (PBS), were injected directly into the plantar of the left hind paw with a 27-gauge needle under brief 2.5% isoflurane anesthesia. One week after the vector injection, 50 µl of CFA (Sigma, St. Louis, Mo., USA) were injected into the same hind paw subcutaneously with a 27-gauge needle under brief isoflurane anesthesia, as described previously {Fraser, 2000 #180}.

Behavioral Tests:

Von Frey Test:

Animals were placed above a grid floor inside a plastic divider. Thresholds to the mechanical pressures applied directly onto the plantar by a blunt metal filament of 100 mm in length and 0.38 mm in diameter were assessed using a custom-made von Frey apparatus. The apparatus uses a high precision load cell (100 g capacity and 0.01 g accuracy) interfaced with a PASPORT load cell amplifier (Model PS-2205, PASCO Scientific, Roseville, Calif.) for continuously measuring the forces applied to the plantar through the metal filament. The DataStudio software from PASCO Scientific was used to record the entire time course of the applied forces and the maximum force immediately before the paw withdrawal. The threshold values were determined as a mean of at least three separate measurements under each testing condition.

Plantar Test:

The plantar sensitivity to heat-induced pain was examined using a plantar algesia meter (Model 390G; IITC Life Science, Woodland Hills, Calif.; active intensity, 23%). Rats were placed inside a plastic divider on a constant-temperature glass plate and acclimated to the environment for at least 20 minutes before testing. A heat source was focused directly onto the plantar surface of the hind paw. Once activated, the apparatus applied a continuous heat stimulus to the plantar surface to evoke a distinctive reflex of paw withdrawal. The rats were examined with at least a five-minute interval between consecutive tests. Paw withdrawal latencies were recorded and averaged for each hind paw. A 22-second automatic cut-off time was set to prevent tissue damage from heating.

Both von Frey and plantar tests were conducted using the schedule as depicted in FIG. 3a. On each testing day after CFA injection, behavioral evaluations were repeated before and at least 15 min after cysteamine administration. Cysteamine (500 µl of 100 mM solution in PBS) was injected subcutaneously elsewhere on the body to prevent tissue damage from repeated injections.

Histology Examination:

To assess the level of exogenous transgene expression, rats were deeply anesthetized with isoflurane and perfused transcardially with a 0.9% phosphate buffered saline. The spinal cord (Th1-L1 level), DRG (L4-L5 level), sciatic nerve, and hind paws were promptly removed, fixed in 4% paraformaldehyde overnight, and cryoprotected in 30% sucrose at 4° C. 16 µm thick frozen sections were prepared using a Leica SM2000R sliding microtome. Micrographic images of the tissue sections were acquired using an OLYMPUS IX81 fluorescent microscope equipped with a monochrome ORCA-ER CCD camera (Hamamatsu, Bridgewater, N.J.). Fluorescent intensity of the eGFP reporter gene was used to measure the relative level of transgene expression.

Statistical Analysis:

All data were analyzed using GraphPad Prism version 4.03 (electrophysiology) and SPSS (in vivo behavioral data). Statistical significance ($P<0.05$) was determined using a repeated-measurement ANOVA, followed by Bonferroni multiple comparisons.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims. We claim:

```

We claim:

1. A chloride channel receptor, comprising:
   a) a transmembrane domain of a mammalian glycine receptor in the absence of the extracellular and intracellular domains of the mammalian glycine receptor, wherein the transmembrane domain comprises domains transmembrane (TM) 1, TM2, and TM3, wherein the transmembrane domain comprises a mutation at S16' of the TM2; and
   b) an extracellular domain of a pH-gated pentameric ligand-gated ion channel from *Gloeobacter violaceus* (GLIC); and
   c) interfacial sequences between the extracellular domain and transmembrane domain, wherein the interfacial sequences comprise, in N-terminal to C-terminal order, loop 2, loop 7, loop 9, pre-TM1 linker, TM2-TM3 linker, and C-terminus, wherein the interfacial sequences and C-terminus are from *Gloeobacter violaceus* or a human;
   and wherein opening of the chloride channel receptor is induced by pH.

2. The chloride channel receptor of claim 1, further comprising domain TM4 of the transmembrane domain of the glycine receptor.

3. The chloride channel receptor of claim 1, further comprising a C-terminal segment of GLIC.

4. The chloride channel receptor of claim 2, further comprising a linker between the TM3 domain and the TM4 domain.

5. The chloride channel of claim 4, wherein the linker comprises the amino acid sequence GGGGG (SEQ ID NO: 49), SQPARAA (SEQ ID NO: 17), or HHRQANGVEDD (SEQ ID NO: 48).

6. The chloride channel receptor of claim 1, wherein the TM2 domain comprises at least one additional amino acid substitution in wherein the wild-type TM2 amino acid sequence is SEQ ID NO: 50 or SEQ ID NO: 51.

7. The chloride channel receptor of claim 1, comprising a mutation at T13' of TM2 of the transmembrane domain.

8. The chloride channel receptor of claim 7, comprising a T13'S mutation.

9. The chloride channel receptor of claim 1, wherein the channel is not permeable to chloride ions at a pH of 7.4.

10. The chloride channel receptor of claim 9, wherein the channel is permeable to chloride ions at a pH of about 6.8 to about 7.2.

11. The chloride channel receptor of claim 1, wherein the channel is permeable to chloride ions at a pH of about 7.0.

12. The chloride channel receptor of claim 2, comprising the amino acid sequence at least 90% identical to the amino acid sequence set forth as one of SEQ ID NOs: 1-7.

13. The chloride channel receptor of claim 12, comprising the amino acid sequence set forth as one of SEQ ID NOs: 1-7.

14. The chloride channel receptor of claim 2, comprising the amino acid sequence of SEQ ID NO: 3.

15. The chloride channel receptor of claim 2, comprising the amino acid sequence of SEQ ID NO: 2.

16. A pharmaceutical composition comprising the chloride channel receptor of claim 1 and a pharmaceutically acceptable carrier.

17. A nanoparticle comprising the chloride channel receptor of claim 1.

18. A pharmaceutical composition comprising the nanoparticle of claim 17 and a pharmaceutically acceptable carrier.

19. A method of reducing inflammatory pain in a subject, comprising administering to the subject a therapeutically effective amount of the pharmaceutical composition of claim 1, thereby reducing inflammatory pain in the subject.

* * * * *